(12) United States Patent
Mauro et al.

(10) Patent No.: US 7,468,275 B2
(45) Date of Patent: *Dec. 23, 2008

(54) SYNTHETIC INTERNAL RIBOSOME ENTRY SITES AND METHODS OF IDENTIFYING SAME

(75) Inventors: Vincent P. Mauro, San Diego, CA (US); Gerald M. Edelman, La Jolla, CA (US); Stephen A. Chappell, Del Mar, CA (US); Geoffrey Owens, San Diego, CA (US); Jason K. Pinkstaff, Cardiff, CA (US); Leslie Krushel, Denver, CO (US); Wei Zhou, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 339 days.

This patent is subject to a terminal disclaimer.

(21) Appl. No.: 10/182,327

(22) PCT Filed: Jan. 26, 2001

(86) PCT No.: PCT/US01/02586

§ 371 (c)(1),
(2), (4) Date: Nov. 27, 2002

(87) PCT Pub. No.: WO01/55369

PCT Pub. Date: Aug. 2, 2001

(65) Prior Publication Data

US 2004/0043468 A1    Mar. 4, 2004

Related U.S. Application Data

(60) Provisional application No. 60/230,956, filed on Sep. 7, 2000, provisional application No. 60/230,852, filed on Sep. 7, 2000, provisional application No. 60/207,804, filed on May 30, 2000, provisional application No. 60/186,496, filed on Mar. 2, 2000, provisional application No. 60/178,816, filed on Jan. 28, 2000, provisional application No. 60/261,312, filed on Jan. 12, 2001.

(51) Int. Cl.
| | |
|---|---|
| C12N 15/63 | (2006.01) |
| C12N 15/85 | (2006.01) |
| C12N 5/10 | (2006.01) |
| C07H 21/02 | (2006.01) |
| C07H 21/04 | (2006.01) |
| A61K 48/00 | (2006.01) |

(52) U.S. Cl. .................. 435/325; 435/320.1; 536/23.1; 536/24.1

(58) Field of Classification Search ................. None
See application file for complete search history.

(56) References Cited

U.S. PATENT DOCUMENTS 6,087,152 A * 7/2000 Hohmann et al. ...... 435/252.31

FOREIGN PATENT DOCUMENTS

WO    WO 94/24870    * 11/1994

OTHER PUBLICATIONS

Stein et al. Mol. Cel. Bio. 1998; 18:3112-119.*
Chappell et al. Proc. Natl. Acad. Sci. 2000; 97:1536-41.*
Chappell et al. J. Biol. Chem. 2003; 278:33793-800.*
Hennecke et al. Nuc. Acids Res. 2001; 29:3327-34.*
Mauro et al. RNA, 2004; 10:895-7.*
Rees et al. Biotechniques. 1996; 20:102-110.*
Shiroki et al. Nuc. Acids Res. 2002; 30:2851-61.*
Wang et al. Nuc. Acids Res. 2005; 33:2248-58.*

* cited by examiner

*Primary Examiner*—David Guzo
(74) *Attorney, Agent, or Firm*—DLA Piper LLP (US)

(57) ABSTRACT

Synthetic and isolated translational regulatory elements, including oligonucleotides that have translational enhancing activity, internal ribosome entry site (IRES) activity, or translational inhibitory activity, and multimers of such translational regulatory elements are provided. In addition, compositions that include such translational regulatory elements are provided, as are methods of using the translational regulatory elements.

31 Claims, 5 Drawing Sheets

YAP1 (87-96)      ACGAGCCAUU (30)
                  | ||||||||
18S (101-92)      UACUCGGUAA (31)

YAP1 (142-127)    CCCAAAACGUUUAAAG (32)
                  |||| |||||||| |||
18S (1453-1438)   GGGUCUUGCAAGAUUC (33)

--- p150 (110-122)    CAGACUUCCAUCG (34)
                  ||o|| ||||||
18S (1413-1401)   GUUUGAAGGUAGC (35)

p150 (145-163)    GCGCUAUCCUCAUCGCGAC (36)
                  || |||||||| |o||||
18S (1547-1529)   CGAGAUAGGGGUCGUGCUG (37)

p150 (403-417)    UUAUGAUUCUUCCUC (38)
                  | |||||||||||| |
18S (1798-1784)   AUUACUAGGAAGGCG (39)

p150 (417-441)    CUUCCCUUCAAUUUCUUAAAGCUUC (40)
                  |o| || ||||||||| ||| |||
18S (1151-1127)   GGAAGGCAGUUAAGGAAAUUCAAAG (41)

FIG. 3

SEQUENCE LISTING

<160> NUMBER OF SEQ ID NOS: 197

<210> SEQ ID NO 1
<211> LENGTH: 196
<212> TYPE: DNA
<213> ORGANISM: Mus musculus

<400> SEQUENCE: 1
ccgccgccca ttcagcgcaa cagccgtcgg tcctctcgct ttcccgtagg ggccgtcggc    60
gttcgtttga aacgcggtcc acccgtccca gcgtagccgc cgctcttcgg cgccgcgcgc   120
aaacttcccg agccggcggg tgcggcggt ggcagcgggg cccggatggg cgcccgggtc   180
ggaggcggcg gcgccc                                                   196

<210> SEQ ID NO 2
<211> LENGTH: 9
<212> TYPE: DNA
<213> ORGANISM: Mus musculus

<400> SEQUENCE: 2 ccggcgggt                                                             9

<210> SEQ ID NO 3
<211> LENGTH: 51
<212> TYPE: DNA
<213> ORGANISM: Mus musculus

<400> SEQUENCE: 3
acatttgctt ctgacatagt tgtgttgact cacaacccca gaaacagaca t              51

<210> SEQ ID NO 4
<211> LENGTH: 51
<212> TYPE: DNA
<213> ORGANISM: Artificial sequence
<220> FEATURE:
<223> OTHER INFORMATION: Gtx IRES inbedded in beta-globin 5' UTR

<400> SEQUENCE: 4
acatttgctt ctgacatccg gcgggtgact cacaacccca gaaacagaca t              51

<210> SEQ ID NO 5
<211> LENGTH: 34
<212> TYPE: DNA
<213> ORGANISM: Artificial sequence
<220> FEATURE:
<223> OTHER INFORMATION: Gtx IRES followed by 25 nt beta-globin

<400> SEQUENCE: 5
ccggcgggtg actcacaacc ccagaaacag acat                                34

<210> SEQ ID NO 6
<211> LENGTH: 115
<212> TYPE: DNA
<213> ORGANISM: Artificial sequence
<220> FEATURE:
<223> OTHER INFORMATION: five repeats of the 9 nt Gtx IRES-element
      interspersed with 9 nt spacers followed by 25 nt of the beta
      globin 5' UT

<400> SEQUENCE: 6
ttctgacatc cggcgggttt ctgacatccg gcgggtttct gacatccggc gggtttctga    60
catccggcgg gtttctgaca tccggcgggt gactcacaac cccagaaaca gacat         115

<210> SEQ ID NO 7
<211> LENGTH: 202
<212> TYPE: DNA
<213> ORGANISM: Artificial sequence
<220> FEATURE:
<223> OTHER INFORMATION: ten repeats of the 9 nt Gtx IRES-element
      interspersed with 9 nt spacers followed by 25 nt of the beta
      globin 5' UT

<400> SEQUENCE: 7
ccggcgggtt tctgacatcc ggcgggtttc tgacatccgg cgggtttctg acatccggcg    60
ggtttctgac atccggcggg tgaattcttc tgacatccgg cgggtttctg acatccggcg    120
ggtttctgac atccggcggg tttctgacat ccggcgggtt tctgacatcc ggcgggtgac    180
tcacaacccc agaaacagac at                                             202

<210> SEQ ID NO 8
<211> LENGTH: 115
<212> TYPE: DNA
<213> ORGANISM: Artificial sequence
<220> FEATURE:
<223> OTHER INFORMATION: five repeats of the 9 nt Gtx IRES-element
      interspersed with 9 nt spacers followed by 25 nt of the beta
      globin 5' UT

<400> SEQUENCE: 8
agttgtgttc cggcgggtag ttgtgttccg gcgggtagtt gtgttccggc gggtagttgt    60
gttccggcgg gtagttgtgt tccggcgggt gactcacaac cccagaaaca gacat         115

<210> SEQ ID NO 9
<211> LENGTH: 202
<212> TYPE: DNA
<213> ORGANISM: Artificial sequence
<220> FEATURE:
<223> OTHER INFORMATION: ten repeats of the 9 nt Gtx IRES-element
      interspersed with 9 nt spacers followed by 25 nt of the beta
      globin 5' UT

<400> SEQUENCE: 9
ccggcgggta gttgtgttcc ggcgggtagt tgtgttccgg cgggtagttg tgttccggcg    60
ggtagttgtg ttccggcggg tgaattcagt tgtgttccgg cgggtagttg tgttccggcg    120
ggtagttgtg ttccggcggg tagttgtgtt ccggcgggta gttgtgttcc ggcgggtgac    180
tcacaacccc agaaacagac at                                             202

<210> SEQ ID NO 10
<211> LENGTH: 115
<212> TYPE: DNA
<213> ORGANISM: Artificial sequence

```
<220> FEATURE:
<223> OTHER INFORMATION: five repeats of the 9 nt Gtx IRES-element
      interspersed with 9 nt spacers followed by 25 nt of the beta
      globin 5' UT

<400> SEQUENCE: 10
aaaaaaaaac cggcgggtaa aaaaaaaccg gcgggtaaaa aaaaaccggc gggtaaaaaa        60
aaaccggcgg gtaaaaaaaa accggcgggt gactcacaac cccagaaaca gacat           115

<210> SEQ ID NO 11
<211> LENGTH: 202
<212> TYPE: DNA
<213> ORGANISM: Artificial sequence
<220> FEATURE:
<223> OTHER INFORMATION: ten repeats of the 9 nt Gtx IRES-element
      interspersed with 9 nt spacers followed by 25 nt of the beta
      globin 5' UT

<400> SEQUENCE: 11
ccggcgggta aaaaaaaacc ggcgggtaaa aaaaaccggc gggtaaaaa aaaaccggcg         60 ggtaaaaaaa aaccggcggg tgaattcaaa aaaaaccgg cgggtaaaaa aaaaccggcg        120
ggtaaaaaaa aaccggcggg taaaaaaaaa ccggcgggta aaaaaaaacc ggcgggtgac      180
tcacaacccc agaaacagac at                                               202

<210> SEQ ID NO 12
<211> LENGTH: 106
<212> TYPE: DNA
<213> ORGANISM: Artificial sequence
<220> FEATURE:
<223> OTHER INFORMATION: eight repeats of the 9 nt spacer, upstream of
      the 9 nt Gtx IRES-e lement, followed by 25 nt of the b-globin
      5' UT

<400> SEQUENCE: 12
ttctgacatt tctgacattt ctgacatttc tgacatttct gacatttctg acatttctga       60
catttctgac atccggcggg tgactcacaa ccccagaaac agacat                     106

<210> SEQ ID NO 13
<211> LENGTH: 106
<212> TYPE: DNA
<213> ORGANISM: Artificial sequence
<220> FEATURE:
<223> OTHER INFORMATION: six repeats of the 9 nt spacer, upstream of two
      repeats of the 9 nt Gtx IRES-element, spaced by the 9 nt spacer,
      followed by the 2 5 nt of the beta-globin 5' UTR

<400> SEQUENCE: 13
ttctgacatt tctgacattt ctgacatttc tgacatttct gacatttctg acatccggcg       60
ggtttctgac atccggcggg tgactcacaa ccccagaaac agacat                     106

<210> SEQ ID NO 14
<211> LENGTH: 106
<212> TYPE: DNA
<213> ORGANISM: Artificial sequence
<220> FEATURE:
<223> OTHER INFORMATION: four repeats of the 9 nt spacer, upstream of
      two repeats of the 9 nt Gtx IRES-element spaced 27 nt apart with
      the 9 nt spacer foll owed by the 25 nt beta-globin 5' UT

<400> SEQUENCE: 14
ttctgacatt tctgacattt ctgacatttc tgacatccgg cgggtttctg acatttctga       60
catttctgac atccggcggg tgactcacaa ccccagaaac agacat                     106
```

<210> SEQ ID NO 15
<211> LENGTH: 106
<212> TYPE: DNA
<213> ORGANISM: Artificial sequence
<220> FEATURE:
<223> OTHER INFORMATION: one repeat of the 9 nt spacer, upstream of two
repeats of the 9 nt Gtx IRES-element spaced 54 nt apart with the
9 nt spacer followed by the 25 nt beta-globin 5' UT

<400> SEQUENCE: 15

```
ttctgacatc cggcgggttt ctgacatttc tgacatttct gacatttctg acatttctga      60
catttctgac atccggcggg tgactcacaa ccccagaaac agacat                    106
```

<210> SEQ ID NO 16
<211> LENGTH: 6250
<212> TYPE: DNA
<213> ORGANISM: Artificial sequence
<220> FEATURE:
<223> OTHER INFORMATION: VECTOR

<400> SEQUENCE: 16

```
gaattctcat gtttgacagc ttatcatcga ttagtccaat tgttaaaga caggatatca       60
gtggtccagg ctcagttttg actcaacaat atcaccagct gaagcctata gagtacgagc     120
catagataga ataaaagatt ttatttagtc tccagaaaaa ggggggaatg aaagacccca     180
cctgtaggtt tggcaagcta gaaatgtagt cttatgcaat acacttgtag tcttgcaaca     240
tggtaacgat gagttagcaa catgccttac aaggagagaa aaagcaccgt gcatgccgat     300
tggtggaagt aaggtggtac gatcgtgcct tattaggaag gcaacagaca ggtctgacat     360
ggattggacg aaccactcta gagaaccatc agatgtttcc agggtgcccc aaggacctga     420
aaatgaccct gtgccttatt tgaactaacc aatcagttcg cttctcgctt ctgttcgcgc     480
gcttctgctc cccgagctca ataaaagagc ccacaacccc tcactcggcg cgccagtcct     540
ccgattgact gcgtcgcccg gtacccgta ttcccaataa agcctcttgc tgtttgcatc     600
cgaatcgtgg actcgctgat ccttgggagg gtctcctcag attgattgac tgcccacctc     660
ggggtctttc atttggaggt tccaccgaga tttggagacc ccagcccagg gaccaccgac     720
ccccccgccg ggaggtaagc tggccagcgg tcgtttcgtg tctgtctctg tctttgtgcg     780
tgtttgtgcc ggcatctaat gtttgcgcct gcgtctgtac tagttagcta actagctctg     840
tatctggcgg acccgtggtg gaactgacga gttctgaaca cccggccgca accctgggag     900
acgtcccagg gactttgggg gccgttttg tggcccgacc tgaggaaggg agtcgatgtg     960
gaatccgacc ccgtcaggat atgtggttct ggtaggagac gagaacctaa aacagttccc    1020
gcctccgtct gaatttttgc tttcggtttg gaaccgaagc cgcgcgtctt gtctgctgca    1080
gcatcgttct gtgttgtctc tgtctgactg tgtttctgta tttgtctgaa aattagggcc    1140
agactgttac cactccctta agtttgacct taggtcactg gaaagatgtc gagcggatcg    1200
ctcacaacca gtcggtagat gtcaagaaga gacgttgggt taccttctgc tctgcagaat    1260
ggccaacctt taacgtcgga tggccgcgag acggcacctt taaccgagac ctcatcaccc    1320
aggttaagat caaggtcttt cacctggccc gcatggacac ccagaccagg tcccctacat    1380
cgtgacctgg gaagccttgg cttttgaccc ccctccctgg gtcaagccct tgtacaccc     1440
taagcctccg cctcctcttc ctccatccgc cccgtctctc cccttgaac ctcctcgttc    1500
gaccccgcct cgatcctccc tttatccagc cctcactcct tctctaggcg ccggaattcg    1560
ttcatggtga gcaagggcga ggagctgttc accggggtgg tgcccatcct ggtcgagctg    1620
```

```
gacggcgacg taaacggcca caagttcagc gtgtccggcg agggcgaggg cgatgccacc    1680
tacggcaagc tgaccctgaa gttcatctgc accaccggca agctgcccgt gccctggccc    1740
accctcgtga ccaccctgac ctacggcgtg cagtgcttca gccgctaccc cgaccacatg    1800
aagcagcacg acttcttcaa gtccgccatg cccgaaggct acgtccagga gcgcaccatc    1860
ttcttcaagg acgacggcaa ctacaagacc cgcgccgagg tgaagttcga gggcgacacc    1920
ctggtgaacc gcatcgagct gaagggcatc gacttcaagg aggacggcaa catcctgggg    1980
cacaagctgg agtacaacta caacagccac aacgtctata tcatggccga caagcagaag    2040
aacggcatca aggccaactt caagacccgc cacaacatcg aggacggcgg cgtgcagctc    2100
gccgaccact accagcagaa cacccccatc ggcgacggcc ccgtgctgct gcccgacaac    2160
cactacctga gcacccagtc cgccctgagc aagaccccca acgagaagcg cgatcacatg    2220
gtcctgctgg agttcgtgac cgccgccggg atcactctcg gcatggacga gctgtacaag    2280
taaagcggcc gcgactctag agtcgaggat ccgctagcta gttaattaat cgcgacgacg    2340
cgtcgccatg gtgagcaagg gcgaggagct gttcaccggg gtggtgccca tcctggtcga    2400
gctggacggc gacgtaaacg ccacaagtt cagcgtgtcc ggcgagggcg agggcgatgc    2460
cacctacggc aagctgaccc tgaagttcat ctgcaccacc ggcaagctgc ccgtgccctg    2520
gcccaccctc gtgaccaccc tgacctgggg cgtgcagtgc ttcagccgct accccgacca    2580
catgaagcag cacgacttct tcaagtccgc catgcccgaa ggctacgtcc aggagcgcac    2640
catcttcttc aaggacgacg gcaactacaa gacccgcgcc gaggtgaagt tcgagggcga    2700
caccctggtg aaccgcatcg agctgaaggg catcgacttc aaggaggacg gcaacatcct    2760
ggggcacaag ctggagtaca actacatcag ccacaacgtc tatatcaccg ccgacaagca    2820
gaagaacggc atcaaggcca acttcaagat ccgccacaac atcgaggacg gcagcgtgca    2880
gctcgccgac cactaccagc agaacacccc catcggcgac ggccccgtgc tgctgcccga    2940
caaccactac ctgagcaccc agtccgccct gagcaaagac cccaacgaga gcgcgatca    3000 catggtcctg ctggagttcg tgaccgccgc cgggatcact ctcggcatgg acgagctgta    3060
caagtaagtc gacggtatcg ataaaataaa agattttatt tagtctccag aaaaaggggg    3120
gaatgaaaga ccccacctgt aggtttggca agctagaatg cataaatgta gtcttatgca    3180
atacacttgt agtcttgcaa catggtaacg atgagttagc aacatgcctt acaaggagag    3240
aaaaagcacc gtgcatgccg attggtggaa gtaaggtggt acgatcgtgc cttattagga    3300
aggcaacaga caggtctgac atggattgga cgaaccacta gatctgaagg ggggctataa    3360
aagcgatgga tccgagctcg gccctcattc tggagactct agaggccttg aattcgcggc    3420
cgcgccagtc ctccgattga ctgcgtcgcc cgggtaccgt gtatccaata aaccctcttg    3480
cagttgcatc cgacttgtgg tctcgctgtt ccttgggagg gtctcctctg agtgattgac    3540
tacccgtcag cggggtctt tcatttgggg gctcgtccgg gatcgggaga ccctgccca    3600 gggaccaccg acccaccacc gggaggtaag ctggctgcct cgcgcgtttc ggtgatgacg    3660
gtgaaaacct ctgacacatg cagctcccgg agacggtcac agcttgtctg taagcggatg    3720
ccgggagcag acaagcccgt cagggcgcgt cagcgggtgt tggcgggtgt cggggcgcag    3780
ccatgaccca gtcacgtagc gatagcggag tgtatactgg cttaactatg cggcatcaga    3840
gcagattgta ctgagagtgc accatatgtc cgcccatccc gcccctaact ccgcccagtt    3900
ccgcccattc tccgccccat ggctgactaa ttttttttat ttatgcagag gccgaggccg    3960
cctcggcctc tgagctattc cagaagtagt gaggaggctt ttttggaggc ctaggctttt    4020
```

-continued

```
gcaacatatg tccgcccatc ccgcccctaa ctccgcccag ttccgcccat tctccgcccc    4080
atggctgact aatttttttt atttatgcag aggccgaggc cgcctcggcc tctgagctat    4140
tccagaagta gtgaggaggc ttttttggag gcctaggctt ttgcaacata tgcggtgtga    4200
aataccgcac agatgcgtaa ggagaaaata ccgcatcagg cgctcttccg cttcctcgct    4260
cactgactcg ctgcgctcgg tcgttcggct gcggcgagcg gtatcagctc actcaaaggc    4320
ggtaatacgg ttatccacag aatcagggga taacgcagga agaacatgt gagcaaaagg    4380 ccagcaaaag gccaggaacc gtaaaaaggc cgcgttgctg gcgttttttcc ataggctccg    4440 cccccctgac gagcatcaca aaaatcgacg ctcaagtcag aggtggcgaa acccgacagg    4500
actataaaga taccaggcgt ttccccctgg aagctccctc gtgcgctctc ctgttccgac    4560
cctgccgctt accggatacc tgtccgcctt tctcccttcg ggaagcgtgg cgctttctca    4620
tagctcacgc tgtaggtatc tcagttcggt gtaggtcgtt cgctccaagc tgggctgtgt    4680
gcacgaaccc cccgttcagc ccgaccgctg cgccttatcc ggtaactatc gtcttgagtc    4740
caacccggta agacacgact tatcgccact ggcagcagcc actggtaaca ggattagcag    4800
agcgaggtat gtaggcggtg ctacagagtt cttgaagtgg tggcctaact acggctacac    4860
tagaaggaca gtatttggta tctgcgctct gctgaagcca gttaccttcg gaaaaagagt    4920
tggtagctct tgatccggca aacaaaccac cgctggtagc ggtggttttt ttgtttgcaa    4980
gcagcagatt acgcgcagaa aaaaggatc tcaagaagat cctttgatct tttctacggg    5040
gtctgacgct cagtggaacg aaaactcacg ttaagggatt ttggtcatga gattatcaaa    5100
aaggatcttc acctagatcc ttttaaatta aaaatgaagt tttaaatcaa tctaaagtat    5160
atatgagtaa acttggtctg acagttacca atgcttaatc agtgaggcac ctatctcagc    5220
gatctgtcta tttcgttcat ccatagttgc ctgactcccc gtcgtgtaga taactacgat    5280
acgggagggc ttaccatctg gccccagtgc tgcaatgata ccgcgagacc cacgctcacc    5340
ggctccagat ttatcagcaa taaaccagcc agccggaagg gccgagcgca gaagtggtcc    5400
tgcaacttta tccgcctcca tccagtctat taattgttgc cgggaagcta gagtaagtag    5460
ttcgccagtt aatagtttgc gcaacgttgt tgccattgct gcaggcatcg tggtgtcacg    5520
ctcgtcgttt ggtatggctt cattcagctc cggttcccaa cgatcaaggc gagttacatg    5580
atcccccatg ttgtgcaaaa aagcggttag ctccttcggt cctccgatcg ttgtcagaag    5640
taagttggcc gcagtgttat cactcatggt tatggcagca ctgcataatt ctcttactgt    5700
catgccatcc gtaagatgct tttctgtgac tggtgagtac tcaaccaagt cattctgaga    5760
atagtgtatg cggcgaccga gttgctcttg cccggcgtca acacgggata ataccgcgcc    5820
acatagcaga actttaaaag tgctcatcat tggaaaacgt tcttcgggc gaaaactctc    5880 aaggatctta ccgctgttga tccagttc gatgtaaccc actcgtgcac ccaactgatc    5940
ttcagcatct tttactttca ccagcgtttc tgggtgagca aaaacaggaa ggcaaaatgc    6000
cgcaaaaaag ggaataaggg cgacacggaa atgttgaata ctcatactct tcctttttca    6060
atattattga agcatttatc agggttattg tctcatgagc ggatacatat ttgaatgtat    6120
ttagaaaaat aaacaaatag gggttccgcg cacatttccc cgaaaagtgc cacctgacgt    6180
ctaagaaacc attattatca tgacattaac ctataaaaat aggcgtatca cgaggccctt    6240
tcgtcttcaa                                                          6250
```

<210> SEQ ID NO 17
<211> LENGTH: 117
<212> TYPE: DNA
<213> ORGANISM: Artificial sequence
<220> FEATURE:
<223> OTHER INFORMATION: (SI/Gtx133-141) 5beta/RPh

<400> SEQUENCE: 17
ttctgacatc cggcgggatt ctgacatccg gcgggattct gacatccggc gggattctga      60
catccggcgg gattctgaca tccggcggga gactcacaac cccagaaaca gacatcc       117

<210> SEQ ID NO 18
<211> LENGTH: 117
<212> TYPE: DNA
<213> ORGANISM: Artificial sequence
<220> FEATURE:
<223> OTHER INFORMATION: (SI/Gtx133-141) 5beta/RPh

<400> SEQUENCE: 18
ttctgacatc cggcggaatt ctgacatccg gcggaattct gacatccggc ggaattctga      60
catccggcgg aattctgaca tccggcggaa gactcacaac cccagaaaca gacatcc       117

<210> SEQ ID NO 19
<211> LENGTH: 117
<212> TYPE: DNA
<213> ORGANISM: Saccharomyces cerevisiae

<400> SEQUENCE: 19
ttctgacatc cggcgaaatt ctgacatccg gcgaaattct gacatccggc gaaattctga      60
catccggcga aattctgaca tccggcgaaa gactcacaac cccagaaaca gacatcc       117

<210> SEQ ID NO 20
<211> LENGTH: 117
<212> TYPE: DNA
<213> ORGANISM: Artificial sequence
<220> FEATURE:
<223> OTHER INFORMATION: (SI/Gtx133-141) 5beta/RPh

<400> SEQUENCE: 20
ttctgacatc cggcgggtct ctgacatccg gcgggtctct gacatccggc gggtctctga      60
catccggcgg gtctctgaca tccggcgggt cactcacaac cccagaaaca gacatcc       117

<210> SEQ ID NO 21
<211> LENGTH: 117
<212> TYPE: DNA
<213> ORGANISM: Artificial sequence
<220> FEATURE:
<223> OTHER INFORMATION: (SI/Gtx133-141) 5beta/RPh

<400> SEQUENCE: 21
ttctgacatc cggcgggtca ctgacatccg gcgggtcact gacatccggc gggtcactga      60
catccggcgg gtcactgaca tccggcgggt cactcacaac cccagaaaca gacatcc       117

<210> SEQ ID NO 22
<211> LENGTH: 117
<212> TYPE: DNA
<213> ORGANISM: Artificial sequence
<220> FEATURE:
<223> OTHER INFORMATION: (SI/Gtx133-141) 5beta/RPh

```
<400> SEQUENCE: 22
ttctgacatc cggcgggtca ttgacatccg gcgggtcatt gacatccggc gggtcattga    60
catccggcgg gtcattgaca tccggcgggt cattcacaac cccagaaaca gacatcc     117

<210> SEQ ID NO 23
<211> LENGTH: 151
<212> TYPE: DNA
<213> ORGANISM: Rattus norvegicus

<400> SEQUENCE: 23
cagaagcccc aagctcgtca atcaagctgg ttctccattt gcactcagga gcacgggcag    60
gcgagtggcc cctagttctg ggagcagagt atcagcatcc cagtcctagt cccgagccta   120
aagcctcgcc tgcctgccca gtgccaggat g                                 151

<210> SEQ ID NO 24
<211> LENGTH: 148
<212> TYPE: DNA
<213> ORGANISM: Rattus norvegicus

<400> SEQUENCE: 24
gttattctcc gagggggccccg acagcccccg ggagctccag gatgaggagt ccggcagctg    60
cctctgggtg cagaagtcca agctgttggt gattgaagtg aagactattt cctgtcatta   120
tagccgtcgc gctgcttctc gacagtcc                                     148

<210> SEQ ID NO 25
<211> LENGTH: 216
<212> TYPE: DNA
<213> ORGANISM: Rattus norvegicus

<400> SEQUENCE: 25
agtgctctgg cgagtagtcc tccctcagcc gcagtctctg ggcctcttca gcttgagcgg    60
cggcgagcct gccacactcg ctaagctcct ccggcaccgc gcacttgcca ctgccactgc   120
cgcttcgcgc ccgctgcagc cgccggctct gaatccttct ggcttccgcc tcagaggagt   180
tcttagcctg tcccgaaccg taaccccggc gagcag                            216

<210> SEQ ID NO 26
<211> LENGTH: 367
<212> TYPE: DNA
<213> ORGANISM: Rattus norvegicus

<400> SEQUENCE: 26
catcctctct acctccgttc ccttcggtct ttctctttct tctccttctt tccctcgttt    60
cttcggtcgc cgggtctccc cggctcctcc cacggaggag ctctagctct gagagtctgc   120
cgtgaccgcg ggtgcgtcca ctttccgtgc ccagattttt attgatccga accaacctat   180
attgtgactg ctggcaagaa ttaagattct tcagcggggc tctaacagag ggagcgctga   240
ttgggaagca ttcagtcagg aaattaaaag aaagaagcca gaacatacca ccagcccttt   300
gcgtatacca cataacaaac gtcattactt tacaacttga ttaggagaca gtacagagat   360
ctgaagg                                                            367

<210> SEQ ID NO 27
<211> LENGTH: 249
<212> TYPE: DNA
<213> ORGANISM: Rattus norvegicus
```

-continued

```
<400> SEQUENCE: 27
ctccagttct ccccgcccac cctacagaaa gtgtctcctg attggctttg aggccgcagg    60
gctcaggtta cattcgcaag agttgcggag cgcgggagac cggacccaag aggagagagg   120
ctggttctgc accgattctg tgctggtccg ggagtgcccg acagccctg aactaccacc    180 cagcattgta caaacccacc cccactctga gccaggctcc accccagcca aggaccctca   240
acaccggca                                                           249

<210> SEQ ID NO 28
<211> LENGTH: 178
<212> TYPE: DNA
<213> ORGANISM: Saccharomyces cerevisiae

<400> SEQUENCE: 28
accgattaag cacagtacct ttacgttata tataggattg gtgtttagct ttttttcctg    60
agcccctggt tgactgtgc atgaacacga gccatttta gtttgtttaa gggaagtttt    120
ttgccaccca aaacgtttaa agaaggaaaa gttgtttctt aaaccatgag tgtgtcta     178

<210> SEQ ID NO 29
<211> LENGTH: 511
<212> TYPE: DNA
<213> ORGANISM: Saccharomyces cerevisiae

<400> SEQUENCE: 29
aatcattttt ttgaaaatta cattaataag gcttttttca atatctctgg aacaacagtt    60
tgtttctact tactaatagc tttaaggacc ctcttggaca tcatgatggc agacttccat   120
cgtagtggga tgatcatatg atgggcgcta tcctcatcgc gactcgataa cgacgtgaga   180
aacgattttt ttttttcttt ttcaccgtat ttttgtgcgt ccttttttcaa ttatagcttt   240 tttttatttt ttttttttct cgtactgttt cactgacaaa agttttttttt caagaaaaat   300 tttcgatgcc gcgttctctg tgtgcaacgg atggatggta gatggaattt caatatgttg   360
cttgaaattt taccaatctt gatattgtga taatttactt aattatgatt cttcctcttc   420
ccttcaattt cttaaagctt cttactttac tccttcttgc tcataaataa gcaaggtaag   480
aggacaactg taattaccta ttacaataat g                                  511

<210> SEQ ID NO 30
<211> LENGTH: 10
<212> TYPE: RNA
<213> ORGANISM: Saccharomyces cerevisiae

<400> SEQUENCE: 30
acgagccauu                                                          10

<210> SEQ ID NO 31
<211> LENGTH: 10
<212> TYPE: RNA
<213> ORGANISM: Saccharomyces cerevisiae

<400> SEQUENCE: 31
aauggcucau                                                          10

<210> SEQ ID NO 32
<211> LENGTH: 16
<212> TYPE: RNA
<213> ORGANISM: Saccharomyces cerevisiae
```

```
<400> SEQUENCE: 32
gaaauuugca aaaccc                                                    16

<210> SEQ ID NO 33
<211> LENGTH: 16
<212> TYPE: RNA
<213> ORGANISM: Saccharomyces cerevisiae

<400> SEQUENCE: 33
cuuagaacgu ucuggg                                                    16

<210> SEQ ID NO 34
<211> LENGTH: 13
<212> TYPE: RNA
<213> ORGANISM: Saccharomyces cerevisiae

<400> SEQUENCE: 34
cagacuucca ucg                                                       13

<210> SEQ ID NO 35
<211> LENGTH: 13
<212> TYPE: RNA
<213> ORGANISM: Saccharomyces cerevisiae

<400> SEQUENCE: 35
cgauggaagu uug                                                       13

<210> SEQ ID NO 36
<211> LENGTH: 19
<212> TYPE: RNA
<213> ORGANISM: Saccharomyces cerevisiae

<400> SEQUENCE: 36
gcgcuauccu caucgcgac                                                 19

<210> SEQ ID NO 37
<211> LENGTH: 19
<212> TYPE: RNA
<213> ORGANISM: Saccharomyces cerevisiae

<400> SEQUENCE: 37
gucgugcugg ggauagagc                                                 19

<210> SEQ ID NO 38
<211> LENGTH: 15
<212> TYPE: RNA
<213> ORGANISM: Saccharomyces cerevisiae

<400> SEQUENCE: 38
uuaugauucu uccuc                                                     15

<210> SEQ ID NO 39
<211> LENGTH: 15
<212> TYPE: RNA
<213> ORGANISM: Artificial sequence
<220> FEATURE:
<223> OTHER INFORMATION: 18s rRNA

<400> SEQUENCE: 39
gcggaaggau cauua                                                     15
```

```
<210> SEQ ID NO 40
<211> LENGTH: 25
<212> TYPE: RNA
<213> ORGANISM: Saccharomyces cerevisiae

<400> SEQUENCE: 40
cuucccuuca auuucuuaaa gcuuc                                          25

<210> SEQ ID NO 41
<211> LENGTH: 25
<212> TYPE: RNA
<213> ORGANISM: Saccharomyces cerevisiae

<400> SEQUENCE: 41
gaaacuuaaa ggaauugacg gaagg                                          25

<210> SEQ ID NO 42
<211> LENGTH: 30
<212> TYPE: DNA
<213> ORGANISM: Artificial sequence
<220> FEATURE:
<223> OTHER INFORMATION: IRES-29

<400> SEQUENCE: 42
gatccaggca gaggagagga gggacgagcg                                     30

<210> SEQ ID NO 43
<211> LENGTH: 30
<212> TYPE: DNA
<213> ORGANISM: Artificial sequence
<220> FEATURE:
<223> OTHER INFORMATION: IRES-23

<400> SEQUENCE: 43
gatccagagc aggaacagcg gaaacgagcg                                     30

<210> SEQ ID NO 44
<211> LENGTH: 30
<212> TYPE: DNA
<213> ORGANISM: Artificial sequence
<220> FEATURE:
<223> OTHER INFORMATION: IRES-18

<400> SEQUENCE: 44
gatccaacgt agttaagccg gagccgagcg                                     30

<210> SEQ ID NO 45
<211> LENGTH: 30
<212> TYPE: DNA
<213> ORGANISM: Artificial sequence
<220> FEATURE:
<223> OTHER INFORMATION: IRES-16

<400> SEQUENCE: 45
gatccaggaa ggtgaacgtc caatcgagcg                                     30

<210> SEQ ID NO 46
<211> LENGTH: 30
<212> TYPE: DNA
<213> ORGANISM: Artificial sequence
<220> FEATURE:
<223> OTHER INFORMATION: IRES-15

<400> SEQUENCE: 46
gatccagagg agacgcatag agaacgagcg                                     30
```

<210> SEQ ID NO 47
<211> LENGTH: 42
<212> TYPE: DNA
<213> ORGANISM: Artificial sequence
<220> FEATURE:
<223> OTHER INFORMATION: oligonucleotide containing 18 random nucleotide
<220> FEATURE:
<221> NAME/KEY: misc_feature
<222> LOCATION: (13)..(30)
<223> OTHER INFORMATION: n is eithe a, c, g, or t

<400> SEQUENCE: 47
acgcgtgatc cannnnnnnn nnnnnnnnnn cgagcgacgc gt                42

<210> SEQ ID NO 48
<211> LENGTH: 135
<212> TYPE: DNA
<213> ORGANISM: Artificial sequence
<220> FEATURE:
<223> OTHER INFORMATION: oligonucleotide containing two segments of
      9 random nucleotides
<220> FEATURE:
<221> NAME/KEY: misc_feature
<222> LOCATION: (69)..(77)
<223> OTHER INFORMATION: n is either a, c, g, or t
<220> FEATURE:
<221> NAME/KEY: misc_feature
<222> LOCATION: (87)..(95)
<223> OTHER INFORMATION: n is either a, c, g, or t

<400> SEQUENCE: 48
ttaattaaga attcttctga cataaaaaaa aattctgaca taaaaaaaaa ttctgacata    60
aaaaaaaann nnnnnnnaaa aaaaaannnn nnnnaaaaa aaaagactca caaccccaga   120
aacagacata cgcgt                                                   135

<210> SEQ ID NO 49
<211> LENGTH: 30
<212> TYPE: RNA
<213> ORGANISM: Artificial sequence
<220> FEATURE:
<223> OTHER INFORMATION: ICS 1-23 a-b

<400> SEQUENCE: 49
gauccagagc aggaacagcg gaaacgagcg                                    30

<210> SEQ ID NO 50
<211> LENGTH: 15
<212> TYPE: RNA
<213> ORGANISM: Artificial sequence
<220> FEATURE:
<223> OTHER INFORMATION: ICS 1-23 b

<400> SEQUENCE: 50
cagcggaaac gagcg                                                    15

<210> SEQ ID NO 51
<211> LENGTH: 14
<212> TYPE: RNA
<213> ORGANISM: Saccharomyces cerevisiae

<400> SEQUENCE: 51
uucucgauuc cgug                                                     14

<210> SEQ ID NO 52
<211> LENGTH: 9
<212> TYPE: DNA
<213> ORGANISM: Artificial sequence

```
<220> FEATURE:
<223> OTHER INFORMATION: 9 nt segment designated as ICA2-17.2

<400> SEQUENCE: 52 tccggtcgt                                                                    9

<210> SEQ ID NO 53
<211> LENGTH: 148
<212> TYPE: DNA
<213> ORGANISM: Artificial sequence
<220> FEATURE:
<223> OTHER INFORMATION: two random 9 nt segments flanked by poly
      (a) 9 and embedded in beta-globin 5' UT

<400> SEQUENCE: 53
gctagcttaa ttaagaattc ttctgacata aaaaaaaatt ctgacataaa aaaaaattct        60
gacataaaaa aaaagggttg tacaaaaaaa aacccagttt caaaaaaaaa gactcacaac       120
cccagaaaca gacatacgcg tcgccatg                                          148

<210> SEQ ID NO 54
<211> LENGTH: 148
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 54
gctagcttaa ttaagaattc ttctgacata aaaaaaaatt ctgacataaa aaaaaattct        60
gacataaaaa aaaatgatt tgtaaaaaaa aagtgtcgat gaaaaaaaaa gactcacaac       120
cccagaaaca gacatacgcg tcgccatg                                          148

<210> SEQ ID NO 55
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 55
gctagcttaa ttaagaattc ttctgacata aaaaaaaatt ctgacataaa aaaaaattcg        60
acataaaaaa aaacacatcc cgaaaaaaaa attatatatc aaaaaaaaag actcacaacc       120
ccagaaacag acatacgcgt cgccatg                                           147

<210> SEQ ID NO 56
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 56
gctagcttaa ttaagaattc ttctgacata aaaaaaaatt ctgacataaa aaaaaattcg        60
acataaaaaa aaaccctgc tcaaaaaaaa agcgtggtag aaaaaaaaag actcacaacc       120
ccagaaacag acatacgcgt cgccatg                                           147
```

<210> SEQ ID NO 57
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 57
gctagcttaa ttaagaattc ttctgacata aaaaaaaatt ctgacataaa aaaaaattcg      60
acataaaaaa aaaatccggg gtaaaaaaaa attaaataaa aaaaaaaaag actcacaacc    120
ccagaaacag acatacgcgt cgccatg                                        147

<210> SEQ ID NO 58
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 58
gctagcttaa ttaagaattc ttctgacata aaaaaaaatt ctgacataaa aaaaaattcg      60
acataaaaaa aaaatcttaa agaaaaaaaa atgcagcgcg aaaaaaaaag actcacaacc    120
ccagaaacag acatacgcgt cgccatg                                        147

<210> SEQ ID NO 59
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 59
gctagcttaa ttaagaattc ttctgacata aaaaaaaatt ctgacataaa aaaaaattcg      60
acataaaaaa aaatatcgtc ttaaaaaaaa aggttgcact aaaaaaaaag actcacaacc    120
ccagaaacag acatacgcgt cgccatg                                        147

<210> SEQ ID NO 60
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 60
gctagcttaa ttaagaattc ttctgacata aaaaaaaatt ctgacataaa aaaaaattcg      60
acataaaaaa aaattggtaa agaaaaaaaa agaagacccg aaaaaaaaag actcacaacc    120
ccagaaacag acatacgcgt cgccatg                                        147

<210> SEQ ID NO 61
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 61
gctagcttaa ttaagaattc ttctgacata aaaaaaaatt ctgacataaa aaaaaattcg      60
acataaaaaa aaagcatgag taaaaaaaaa agctcaccta aaaaaaaaag actcacaacc     120
ccagaaacag acatacgcgt cgccatg                                        147

<210> SEQ ID NO 62
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 62
gctagcttaa ttaagaattc ttctgacata aaaaaaaatt ctgacataaa aaaaaattcg      60
acataaaaaa aaatcggacg ttaaaaaaaa atccggtcgt aaaaaaaaag actcacaacc    120
ccagaaacag acatacgcgt cgccatg                                        147

<210> SEQ ID NO 63
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 63
gctagcttaa ttaagaattc ttctgacata aaaaaaaatt ctgacataaa aaaaaattcg      60
acataaaaaa aaatttactg ctaaaaaaaa atggctgttc aaaaaaaaag actcacaacc    120
ccagaaacag acatacgcgt cgccatg                                        147

<210> SEQ ID NO 64
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 64
gctagcttaa ttaagaattc ttctgacata aaaaaaaatt ctgacataaa aaaaaattcg      60
acataaaaaa aaattaagta gcaaaaaaaa attgtttagt aaaaaaaaag actcacaacc    120
ccagaaacag acatacgcgt cgccatg                                        147

<210> SEQ ID NO 65
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 65
gctagcttaa ttaagaattc ttctgacata aaaaaaaatt ctgacataaa aaaaaattcg      60
acataaaaaa aaatcttgc gtaaaaaaaa agttcctgcg aaaaaaaaag actcacaacc    120
ccagaaacag acatacgcgt cgccatg                                        147

```
<210> SEQ ID NO 66
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 66
gctagcttaa ttaagaattc ttctgacata aaaaaaaatt ctgacataaa aaaaaattcg      60
acataaaaaa aaaagcatga gtaaaaaaaa aagctcacct aaaaaaaaag actcacaacc    120
ccagaaacag acatacgcgt cgccatg                                         147

<210> SEQ ID NO 67
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 67
gctagcttaa ttaagaattc ttctgacata aaaaaaaatt ctgacataaa aaaaaattcg      60
acataaaaaa aaagcagtta ataaaaaaaa agacatcagc aaaaaaaaag actcacaacc    120
ccagaaacag acatacgcgt cgccatg                                         147

<210> SEQ ID NO 68
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 68
gctagcttaa ttaagaattc ttctgacata aaaaaaaatt ctgacataaa aaaaaattcg      60
acataaaaaa aaaaggctg ccaaaaaaaa aaacgtttag aaaaaaaaag actcacaacc    120
ccagaaacag acatacgcgt cgccatg                                         147

<210> SEQ ID NO 69
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 69
gctagcttaa ttaagaattc ttctgacata aaaaaaaatt ctgacataaa aaaaaattcg      60
acataaaaaa aaacttggct caaaaaaaaa aagttcctgt aaaaaaaaag actcacaacc    120
ccagaaacag acatacgcgt cgccatg                                         147

<210> SEQ ID NO 70
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT
```

```
<400> SEQUENCE: 70
gctagcttaa ttaagaattc ttctgacata aaaaaaaatt ctgacataaa aaaaaattcg    60
acataaaaaa aaattcaaca tgaaaaaaaa aagcgtctat aaaaaaaaag actcacaacc   120
ccagaaacag acatacgcgt cgccatg                                      147

<210> SEQ ID NO 71
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 71
gctagcttaa ttaagaattc ttctgacata aaaaaaaatt ctgacataaa aaaaaattcg    60
acataaaaaa aaatcggccg ttaaaaaaaa acccggtggt aaaaaaaaag actcacaacc   120
ccagaaacag acatacgcgt cgccatg                                      147

<210> SEQ ID NO 72
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 72
gctagcttaa ttaagaattc ttctgacata aaaaaaaatt ctgacataaa aaaaaattcg    60
acataaaaaa aaagcgcgtt agaaaaaaaa acctgccttc aaaaaaaaag actcacaacc   120
ccagaaacag acatacgcgt cgccatg                                      147

<210> SEQ ID NO 73
<211> LENGTH: 145
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 73
gctagcttaa ttaagaattc ttctgacata aaaaaaaatt ctgacataaa aaaaaattcg    60
acataaaaaa aaacttggct caaaaaaaaa gttcctgtaa aaaaaaagac tcacaacccc   120
agaaacagac atacgcgtcg ccatg                                        145

<210> SEQ ID NO 74
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 74
gctagcttaa ttaagaattc ttctgacata aaaaaaaatt ctgacataaa aaaaaattcg    60
acataaaaaa aaacgttgat tcaaaaaaaa aacgacctcc aaaaaaaaag actcacaacc   120
ccagaaacag acatacgcgt cgccatg                                      147
```

<210> SEQ ID NO 75
<211> LENGTH: 146
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 75
gctagcttaa ttaagaattc ttctgacata aaaaaaaatt ctgacataaa aaaaaattcg      60
acataaaaaa aaagtcactg ccaaaaaaaa atcgatatta aaaaaaaaga ctcacaaccc     120
cagaaacaga catacgcgtc gccatg                                          146

<210> SEQ ID NO 76
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 76
gctagcttaa ttaagaattc ttctgacata aaaaaaaatt ctgacataaa aaaaaattcg      60
acataaaaaa aaagagagtg agaaaaaaaa atgtcctatt aaaaaaaaag actcacaacc     120
ccagaaacag acatacgcgt cgccatg                                         147

<210> SEQ ID NO 77
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 77
gctagcttaa ttaagaattc ttctgacata aaaaaaaatt ctgacataaa aaaaaattcg      60
acataaaaaa aaacgttgcg tcaaaaaaaa acgcccggcc aaaaaaaaag actcacaacc     120
ccagaaacag acatacgcgt cgccatg                                         147

<210> SEQ ID NO 78
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 78
gctagcttaa ttaagaattc ttctgacata aaaaaaaatt ctgacataaa aaaaaattcg      60
acataaaaaa aaacgcccgg gtaaaaaaaa acatggcggt aaaaaaaaag actcacaacc     120
ccagaaacag acatacgcgt cgccatg                                         147

<210> SEQ ID NO 79
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

```
<400> SEQUENCE: 79
gctagcttaa ttaagaattc ttctgacata aaaaaaaatt ctgacataaa aaaaaattcg    60
acataaaaaa aaacaatttc gtaaaaaaaa agtccgggac aaaaaaaaag actcacaacc   120
ccagaaacag acatacgcgt cgccatg                                      147

<210> SEQ ID NO 80
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 80
gctagcttaa ttaagaattc ttctgacata aaaaaaaatt ctgacataaa aaaaaattcg    60
acataaaaaa aaaagatagc ctaaaaaaaa attgcttatg aaaaaaaaag actcacaacc   120
ccagaaacag acatacgcgt cgccatg                                      147

<210> SEQ ID NO 81
<211> LENGTH: 145
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 81
gctagcttaa ttaagaattc ttctgacata aaaaaaaatt ctgacataaa aaaaaattcg    60
acataaaaaa aaaccaggcg gaaaaaaaaa ctacttccaa aaaaaaagac tcacaacccc   120
agaaacagac atacgcgtcg ccatg                                        145

<210> SEQ ID NO 82
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 82
gctagcttaa ttaagaattc ttctgacata aaaaaaaatt ctgacataaa aaaaaattcg    60
acataaaaaa aaataatcgt agaaaaaaaa aagcaggatg aaaaaaaaag actcacaacc   120
ccagaaacag acatacgcgt cgccatg                                      147

<210> SEQ ID NO 83
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 83
gctagcttaa ttaagaattc ttctgacata aaaaaaaatt ctgacataaa aaaaaattcg    60
acataaaaaa aaatggcatg agaaaaaaaa atgggcggct aaaaaaaaag actcacaacc   120
ccagaaacag acatacgcgt cgccatg                                      147
```

<210> SEQ ID NO 84
<211> LENGTH: 146
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 84
gctagcttaa ttaagaattc ttctgacata aaaaaaaatt ctgacataaa aaaaaattcg     60
acataaaaaa aaattcaaca tgaaaaaaaa agcgtctata aaaaaaaaga ctcacaaccc    120
cagaaacaga catacgcgtc gccatg                                         146

<210> SEQ ID NO 85
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 85
gctagcttaa ttaagaattc ttctgacata aaaaaaaatt ctgacataaa aaaaaattcg     60
acataaaaaa aaacggcgcc agaaaaaaaa aatgtgtggt aaaaaaaaag actcacaacc    120
ccagaaacag acatacgcgt cgccatg                                        147

<210> SEQ ID NO 86
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 86
gctagcttaa ttaagaattc ttctgacata aaaaaaaatt ctgacataaa aaaaaattcg     60
acataaaaaa aaagtcatat caaaaaaaaa acggtgagcg aaaaaaaaag actcacaacc    120
ccagaaacag acatacgcgt cgccatg                                        147

<210> SEQ ID NO 87
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT

<400> SEQUENCE: 87
gctagcttaa ttaagaattc ttctgacata aaaaaaaatt ctgacataaa aaaaaattcg     60
acataaaaaa aaaggcggcg aaaaaaaaaa atcgtttgcc aaaaaaaaag actcacaacc    120
ccagaaacag acatacgcgt cgccatg                                        147

<210> SEQ ID NO 88
<211> LENGTH: 147
<212> TYPE: DNA
<213> ORGANISM: Artificial sequence
<220> FEATURE:
<223> OTHER INFORMATION: two random 9 nt sequences flanked by poly
      (a) 9 and embedded in beta-globin 5' UT -continued

```
<400> SEQUENCE: 88
gctagcttaa ttaagaattc ttctgacata aaaaaaaatt ctgacataaa aaaaaattcg      60
acataaaaaa aaagtaaccc taaaaaaaaa aagcccgctt aaaaaaaaag actcacaacc     120
ccagaaacag acatacgcgt cgccatg                                         147

<210> SEQ ID NO 89
<211> LENGTH: 9
<212> TYPE: DNA
<213> ORGANISM: Artificial sequence
<220> FEATURE:
<223> OTHER INFORMATION: random 9 nt sequence

<400> SEQUENCE: 89 gggttgtac                                                              9

<210> SEQ ID NO 90
<211> LENGTH: 9
<212> TYPE: DNA
<213> ORGANISM: Artificial sequence
<220> FEATURE:
<223> OTHER INFORMATION: random 9 nt sequence

<400> SEQUENCE: 90 cccagtttc                                                              9

<210> SEQ ID NO 91
<211> LENGTH: 9
<212> TYPE: DNA
<213> ORGANISM: Artificial sequence
<220> FEATURE:
<223> OTHER INFORMATION: random 9 nt sequence

<400> SEQUENCE: 91 atgatttgt                                                              9

<210> SEQ ID NO 92
<211> LENGTH: 9
<212> TYPE: DNA
<213> ORGANISM: Artificial sequence
<220> FEATURE:
<223> OTHER INFORMATION: random 9 nt sequence

<400> SEQUENCE: 92 gtgtcgatg                                                              9

<210> SEQ ID NO 93
<211> LENGTH: 9
<212> TYPE: DNA
<213> ORGANISM: Artificial sequence
<220> FEATURE:
<223> OTHER INFORMATION: random 9 nt sequence

<400> SEQUENCE: 93 cacatcccg                                                              9

<210> SEQ ID NO 94
<211> LENGTH: 9
<212> TYPE: DNA
<213> ORGANISM: Artificial sequence
<220> FEATURE:
<223> OTHER INFORMATION: random 9 nt sequence
```

```
<400> SEQUENCE: 94 ttatatatc                                                                    9

<210> SEQ ID NO 95
<211> LENGTH: 9
<212> TYPE: DNA
<213> ORGANISM: Artificial sequence
<220> FEATURE:
<223> OTHER INFORMATION: random 9 nt sequence

<400> SEQUENCE: 95 accctgctc                                                                    9

<210> SEQ ID NO 96
<211> LENGTH: 9
<212> TYPE: DNA
<213> ORGANISM: Artificial sequence
<220> FEATURE:
<223> OTHER INFORMATION: random 9 nt sequence

<400> SEQUENCE: 96 gcgtggtag                                                                    9

<210> SEQ ID NO 97
<211> LENGTH: 9
<212> TYPE: DNA
<213> ORGANISM: Artificial sequence
<220> FEATURE:
<223> OTHER INFORMATION: random 9 nt sequence

<400> SEQUENCE: 97 atccggggt                                                                    9

<210> SEQ ID NO 98
<211> LENGTH: 9
<212> TYPE: DNA
<213> ORGANISM: Artificial sequence
<220> FEATURE:
<223> OTHER INFORMATION: random 9 nt sequence

<400> SEQUENCE: 98 ttaaataaa                                                                    9

<210> SEQ ID NO 99
<211> LENGTH: 9
<212> TYPE: DNA
<213> ORGANISM: Artificial sequence
<220> FEATURE:
<223> OTHER INFORMATION: random 9 nt sequence

<400> SEQUENCE: 99 atcttaaag                                                                    9

<210> SEQ ID NO 100
<211> LENGTH: 9
<212> TYPE: DNA
<213> ORGANISM: Artificial sequence
<220> FEATURE:
<223> OTHER INFORMATION: random 9 nt sequence

<400> SEQUENCE: 100 tgcagcgcg                                                                    9
```

```
<210> SEQ ID NO 101
<211> LENGTH: 9
<212> TYPE: DNA
<213> ORGANISM: Artificial sequence
<220> FEATURE:
<223> OTHER INFORMATION: random 9 nt sequence

<400> SEQUENCE: 101 tatcgtctt                                                                 9

<210> SEQ ID NO 102
<211> LENGTH: 9
<212> TYPE: DNA
<213> ORGANISM: Artificial sequence
<220> FEATURE:
<223> OTHER INFORMATION: random 9 nt sequence

<400> SEQUENCE: 102 ggttgcact                                                                 9

<210> SEQ ID NO 103
<211> LENGTH: 9
<212> TYPE: DNA
<213> ORGANISM: Artificial sequence
<220> FEATURE:
<223> OTHER INFORMATION: random 9 nt sequence

<400> SEQUENCE: 103 ttggtaaag                                                                 9

<210> SEQ ID NO 104
<211> LENGTH: 9
<212> TYPE: DNA
<213> ORGANISM: Artificial sequence
<220> FEATURE:
<223> OTHER INFORMATION: random 9 nt sequence

<400> SEQUENCE: 104 gaagacccg                                                                 9

<210> SEQ ID NO 105
<211> LENGTH: 9
<212> TYPE: DNA
<213> ORGANISM: Artificial sequence
<220> FEATURE:
<223> OTHER INFORMATION: random 9 nt sequence

<400> SEQUENCE: 105 gcatgagta                                                                 9

<210> SEQ ID NO 106
<211> LENGTH: 9
<212> TYPE: DNA
<213> ORGANISM: Artificial sequence
<220> FEATURE:
<223> OTHER INFORMATION: random 9 nt sequence

<400> SEQUENCE: 106 gctcaccta                                                                 9

<210> SEQ ID NO 107
<211> LENGTH: 9
<212> TYPE: DNA
<213> ORGANISM: Artificial sequence
<220> FEATURE:
<223> OTHER INFORMATION: random 9 nt sequence
```

```
<400> SEQUENCE: 107 tcggacgtt                                                                    9

<210> SEQ ID NO 108
<211> LENGTH: 9
<212> TYPE: DNA
<213> ORGANISM: Artificial sequence
<220> FEATURE:
<223> OTHER INFORMATION: random 9 nt sequence

<400> SEQUENCE: 108 tccggtcgt                                                                    9

<210> SEQ ID NO 109
<211> LENGTH: 9
<212> TYPE: DNA
<213> ORGANISM: Artificial sequence
<220> FEATURE:
<223> OTHER INFORMATION: random 9 nt sequence

<400> SEQUENCE: 109 tttactgct                                                                    9

<210> SEQ ID NO 110
<211> LENGTH: 9
<212> TYPE: DNA
<213> ORGANISM: Artificial sequence
<220> FEATURE:
<223> OTHER INFORMATION: random 9 nt sequence

<400> SEQUENCE: 110 tggctgttc                                                                    9

<210> SEQ ID NO 111
<211> LENGTH: 9
<212> TYPE: DNA
<213> ORGANISM: Artificial sequence
<220> FEATURE:
<223> OTHER INFORMATION: random 9 nt sequence

<400> SEQUENCE: 111 ttaagtagc                                                                    9

<210> SEQ ID NO 112
<211> LENGTH: 9
<212> TYPE: DNA
<213> ORGANISM: Artificial sequence
<220> FEATURE:
<223> OTHER INFORMATION: random 9 nt sequence

<400> SEQUENCE: 112 ttgtttagt                                                                    9

<210> SEQ ID NO 113
<211> LENGTH: 9
<212> TYPE: DNA
<213> ORGANISM: Artificial sequence
<220> FEATURE:
<223> OTHER INFORMATION: random 9 nt sequence

<400> SEQUENCE: 113 atcttgcgt                                                                    9
```

-continued

```
<210> SEQ ID NO 114
<211> LENGTH: 9
<212> TYPE: DNA
<213> ORGANISM: Artificial sequence
<220> FEATURE:
<223> OTHER INFORMATION: random 9 nt sequence

<400> SEQUENCE: 114 gttcctgcg                                                              9

<210> SEQ ID NO 115
<211> LENGTH: 9
<212> TYPE: DNA
<213> ORGANISM: Artificial sequence
<220> FEATURE:
<223> OTHER INFORMATION: random 9 nt sequence

<400> SEQUENCE: 115 agcatgagt                                                              9

<210> SEQ ID NO 116
<211> LENGTH: 9
<212> TYPE: DNA
<213> ORGANISM: Artificial sequence
<220> FEATURE:
<223> OTHER INFORMATION: random 9 nt sequence

<400> SEQUENCE: 116 agctcacct                                                              9

<210> SEQ ID NO 117
<211> LENGTH: 9
<212> TYPE: DNA
<213> ORGANISM: Artificial sequence
<220> FEATURE:
<223> OTHER INFORMATION: random 9 nt sequence

<400> SEQUENCE: 117 gcagttaat                                                              9

<210> SEQ ID NO 118
<211> LENGTH: 9
<212> TYPE: DNA
<213> ORGANISM: Artificial sequence
<220> FEATURE:
<223> OTHER INFORMATION: random 9 nt sequence

<400> SEQUENCE: 118 gacatcagc                                                              9

<210> SEQ ID NO 119
<211> LENGTH: 9
<212> TYPE: DNA
<213> ORGANISM: Artificial sequence
<220> FEATURE:
<223> OTHER INFORMATION: random 9 nt sequence

<400> SEQUENCE: 119 aaggctgcc                                                              9

<210> SEQ ID NO 120
<211> LENGTH: 9
<212> TYPE: DNA
<213> ORGANISM: Artificial sequence
<220> FEATURE:
<223> OTHER INFORMATION: random 9 nt sequence
```

```
<400> SEQUENCE: 120 aacgtttag                                                          9

<210> SEQ ID NO 121
<211> LENGTH: 9
<212> TYPE: DNA
<213> ORGANISM: Artificial sequence
<220> FEATURE:
<223> OTHER INFORMATION: random 9 nt sequence

<400> SEQUENCE: 121 cttggctca                                                          9

<210> SEQ ID NO 122
<211> LENGTH: 9
<212> TYPE: DNA
<213> ORGANISM: Artificial sequence
<220> FEATURE:
<223> OTHER INFORMATION: random 9 nt sequence

<400> SEQUENCE: 122 agttcctgt                                                          9

<210> SEQ ID NO 123
<211> LENGTH: 9
<212> TYPE: DNA
<213> ORGANISM: Artificial sequence
<220> FEATURE:
<223> OTHER INFORMATION: random 9 nt sequence

<400> SEQUENCE: 123 ttcaacatg                                                          9

<210> SEQ ID NO 124
<211> LENGTH: 8
<212> TYPE: DNA
<213> ORGANISM: Artificial sequence
<220> FEATURE:
<223> OTHER INFORMATION: random 9 nt sequence

<400> SEQUENCE: 124 gcgtctat                                                           8

<210> SEQ ID NO 125
<211> LENGTH: 9
<212> TYPE: DNA
<213> ORGANISM: Artificial sequence
<220> FEATURE:
<223> OTHER INFORMATION: random 9 nt sequence

<400> SEQUENCE: 125 tcggccgtt                                                          9

<210> SEQ ID NO 126
<211> LENGTH: 9
<212> TYPE: DNA
<213> ORGANISM: Artificial sequence
<220> FEATURE:
<223> OTHER INFORMATION: random 9 nt sequence

<400> SEQUENCE: 126 cccggtggt                                                          9
```

```
<210> SEQ ID NO 127
<211> LENGTH: 9
<212> TYPE: DNA
<213> ORGANISM: Artificial sequence
<220> FEATURE:
<223> OTHER INFORMATION: random 9 nt sequence

<400> SEQUENCE: 127 gcgcgttag                                                              9

<210> SEQ ID NO 128
<211> LENGTH: 9
<212> TYPE: DNA
<213> ORGANISM: Artificial sequence
<220> FEATURE:
<223> OTHER INFORMATION: random 9 nt sequence

<400> SEQUENCE: 128 cctgccttc                                                              9

<210> SEQ ID NO 129
<211> LENGTH: 8
<212> TYPE: DNA
<213> ORGANISM: Artificial sequence
<220> FEATURE:
<223> OTHER INFORMATION: random 9 nt sequence

<400> SEQUENCE: 129 cttggctc                                                               8

<210> SEQ ID NO 130
<211> LENGTH: 8
<212> TYPE: DNA
<213> ORGANISM: Artificial sequence
<220> FEATURE:
<223> OTHER INFORMATION: random 9 nt sequence

<400> SEQUENCE: 130 gttcctgt                                                               8

<210> SEQ ID NO 131
<211> LENGTH: 9
<212> TYPE: DNA
<213> ORGANISM: Artificial sequence
<220> FEATURE:
<223> OTHER INFORMATION: random 9 nt sequence

<400> SEQUENCE: 131 cgttgattc                                                              9

<210> SEQ ID NO 132
<211> LENGTH: 9
<212> TYPE: DNA
<213> ORGANISM: Artificial sequence
<220> FEATURE:
<223> OTHER INFORMATION: random 9 nt sequence

<400> SEQUENCE: 132 acgacctcc                                                              9

<210> SEQ ID NO 133
<211> LENGTH: 9
<212> TYPE: DNA
<213> ORGANISM: Artificial sequence
<220> FEATURE:
<223> OTHER INFORMATION: random 9 nt sequence
```

```
<400> SEQUENCE: 133 gtcactgcc                                                                    9

<210> SEQ ID NO 134
<211> LENGTH: 8
<212> TYPE: DNA
<213> ORGANISM: Artificial sequence
<220> FEATURE:
<223> OTHER INFORMATION: random 9 nt sequence

<400> SEQUENCE: 134 tcgatatt                                                                     8

<210> SEQ ID NO 135
<211> LENGTH: 9
<212> TYPE: DNA
<213> ORGANISM: Artificial sequence
<220> FEATURE:
<223> OTHER INFORMATION: random 9 nt sequence

<400> SEQUENCE: 135 gagagtgag                                                                    9

<210> SEQ ID NO 136
<211> LENGTH: 9
<212> TYPE: DNA
<213> ORGANISM: Artificial sequence
<220> FEATURE:
<223> OTHER INFORMATION: random 9 nt sequence

<400> SEQUENCE: 136 tgtcctatt                                                                    9

<210> SEQ ID NO 137
<211> LENGTH: 9
<212> TYPE: DNA
<213> ORGANISM: Artificial sequence
<220> FEATURE:
<223> OTHER INFORMATION: random 9 nt sequence

<400> SEQUENCE: 137 cgttgcgtc                                                                    9

<210> SEQ ID NO 138
<211> LENGTH: 9
<212> TYPE: DNA
<213> ORGANISM: Artificial sequence
<220> FEATURE:
<223> OTHER INFORMATION: random 9 nt sequence

<400> SEQUENCE: 138 cgcccggcc                                                                    9

<210> SEQ ID NO 139
<211> LENGTH: 9
<212> TYPE: DNA
<213> ORGANISM: Artificial sequence
<220> FEATURE:
<223> OTHER INFORMATION: random 9 nt sequence

<400> SEQUENCE: 139 cgcccgggt                                                                    9
```

```
<210> SEQ ID NO 140
<211> LENGTH: 9
<212> TYPE: DNA
<213> ORGANISM: Artificial sequence
<220> FEATURE:
<223> OTHER INFORMATION: random 9 nt sequence

<400> SEQUENCE: 140 catggcggt                                                                  9

<210> SEQ ID NO 141
<211> LENGTH: 9
<212> TYPE: DNA
<213> ORGANISM: Artificial sequence
<220> FEATURE:
<223> OTHER INFORMATION: random 9 nt sequence

<400> SEQUENCE: 141 caatttcgt                                                                  9

<210> SEQ ID NO 142
<211> LENGTH: 9
<212> TYPE: DNA
<213> ORGANISM: Artificial sequence
<220> FEATURE:
<223> OTHER INFORMATION: random 9 nt sequence

<400> SEQUENCE: 142 gtccgggac                                                                  9

<210> SEQ ID NO 143
<211> LENGTH: 9
<212> TYPE: DNA
<213> ORGANISM: Artificial sequence
<220> FEATURE:
<223> OTHER INFORMATION: random 9 nt sequence

<400> SEQUENCE: 143 agatagcct                                                                  9

<210> SEQ ID NO 144
<211> LENGTH: 9
<212> TYPE: DNA
<213> ORGANISM: Artificial sequence
<220> FEATURE:
<223> OTHER INFORMATION: random 9 nt sequence

<400> SEQUENCE: 144 ttgcttatg                                                                  9

<210> SEQ ID NO 145
<211> LENGTH: 9
<212> TYPE: DNA
<213> ORGANISM: Artificial sequence
<220> FEATURE:
<223> OTHER INFORMATION: random 9 nt sequence

<400> SEQUENCE: 145 ccaggcgga                                                                  9

<210> SEQ ID NO 146
<211> LENGTH: 8
<212> TYPE: DNA
<213> ORGANISM: Artificial sequence
<220> FEATURE:
<223> OTHER INFORMATION: random 9 nt sequence
```

```
<400> SEQUENCE: 146 ctacttcc                                                          8

<210> SEQ ID NO 147
<211> LENGTH: 9
<212> TYPE: DNA
<213> ORGANISM: Artificial sequence
<220> FEATURE:
<223> OTHER INFORMATION: random 9 nt sequence

<400> SEQUENCE: 147 taatcgtag                                                         9

<210> SEQ ID NO 148
<211> LENGTH: 9
<212> TYPE: DNA
<213> ORGANISM: Artificial sequence
<220> FEATURE:
<223> OTHER INFORMATION: random 9 nt sequence

<400> SEQUENCE: 148 agcaggatg                                                         9

<210> SEQ ID NO 149
<211> LENGTH: 9
<212> TYPE: DNA
<213> ORGANISM: Artificial sequence
<220> FEATURE:
<223> OTHER INFORMATION: random 9 nt sequence

<400> SEQUENCE: 149 tggcatgag                                                         9

<210> SEQ ID NO 150
<211> LENGTH: 9
<212> TYPE: DNA
<213> ORGANISM: Artificial sequence
<220> FEATURE:
<223> OTHER INFORMATION: random 9 nt sequence

<400> SEQUENCE: 150 tgggcggct                                                         9

<210> SEQ ID NO 151
<211> LENGTH: 9
<212> TYPE: DNA
<213> ORGANISM: Artificial sequence
<220> FEATURE:
<223> OTHER INFORMATION: random 9 nt sequence

<400> SEQUENCE: 151 ttcaacatg                                                         9

<210> SEQ ID NO 152
<211> LENGTH: 8
<212> TYPE: DNA
<213> ORGANISM: Artificial sequence
<220> FEATURE:
<223> OTHER INFORMATION: random 9 nt sequence

<400> SEQUENCE: 152 gcgtctat                                                          8
```

```
<210> SEQ ID NO 153
<211> LENGTH: 9
<212> TYPE: DNA
<213> ORGANISM: Artificial sequence
<220> FEATURE:
<223> OTHER INFORMATION: random 9 nt sequence

<400> SEQUENCE: 153 cggcgccag                                                                          9

<210> SEQ ID NO 154
<211> LENGTH: 9
<212> TYPE: DNA
<213> ORGANISM: Artificial sequence
<220> FEATURE:
<223> OTHER INFORMATION: random 9 nt sequence

<400> SEQUENCE: 154 atgtgtggt                                                                          9

<210> SEQ ID NO 155
<211> LENGTH: 9
<212> TYPE: DNA
<213> ORGANISM: Artificial sequence
<220> FEATURE:
<223> OTHER INFORMATION: random 9 nt sequence

<400> SEQUENCE: 155 gtcatatca                                                                          9

<210> SEQ ID NO 156
<211> LENGTH: 9
<212> TYPE: DNA
<213> ORGANISM: Artificial sequence
<220> FEATURE:
<223> OTHER INFORMATION: random 9 nt sequence

<400> SEQUENCE: 156 cggtgagcg                                                                          9

<210> SEQ ID NO 157
<211> LENGTH: 9
<212> TYPE: DNA
<213> ORGANISM: Artificial sequence
<220> FEATURE:
<223> OTHER INFORMATION: random 9 nt sequence

<400> SEQUENCE: 157 ggcggcgga                                                                          9

<210> SEQ ID NO 158
<211> LENGTH: 9
<212> TYPE: DNA
<213> ORGANISM: Artificial sequence
<220> FEATURE:
<223> OTHER INFORMATION: random 9 nt sequence

<400> SEQUENCE: 158 tcgtttgcc                                                                          9

<210> SEQ ID NO 159
<211> LENGTH: 9
<212> TYPE: DNA
<213> ORGANISM: Artificial sequence
<220> FEATURE:
<223> OTHER INFORMATION: random 9 nt sequence
```

-continued

<400> SEQUENCE: 159 gtaaccccta                                                              9

<210> SEQ ID NO 160
<211> LENGTH: 9
<212> TYPE: DNA
<213> ORGANISM: Artificial sequence
<220> FEATURE:
<223> OTHER INFORMATION: random 9 nt sequence

<400> SEQUENCE: 160 agcccgctt                                                               9

<210> SEQ ID NO 161
<211> LENGTH: 156
<212> TYPE: DNA
<213> ORGANISM: Rattus norvegicus

<400> SEQUENCE: 161
agtttcctcg gcggcgggag gcgagagcac taggagcaga gagagcgcgg gggccaccgg       60
agacggcggc ggcggcggcg acgacgcgga cacagtcagg gtgcggcgga tcttccactt      120
gcacacggag cagtcggtgg cccacgcagg atcacg                                156

<210> SEQ ID NO 162
<211> LENGTH: 427
<212> TYPE: DNA
<213> ORGANISM: Rattus norvegicus

<400> SEQUENCE: 162
ccccagcctg cctaggtgct gggagccggg agctggatta tggtggcctg agcagccgac       60
gcagccgcag gagctgggag tccctcacgc tgcaaagtcc gcctggaaga ccctgaaagc      120
tgcaggctcc gatagccatg cccgcccctc ccagccccac aaggggcccg atccccccgc      180
tgaggctggc ggtcgccgtc cagatgtagc tgggtccccc ggatcgccat cgtcctcttc      240
tctcgtgcgc tacagatttc tcctgcccac tctccaccgc cgggagcagg aactgagcga      300
ggggcctgca gactctgcag tcctgatgcc cccgaggccg ctctcctgag agaagccacc      360
accacccaga cttaggggca ggcaagaggg acagtcgcca accggagcca caaggcccgg      420
gctcacc                                                               427

<210> SEQ ID NO 163
<211> LENGTH: 321
<212> TYPE: DNA
<213> ORGANISM: Homo sapiens

<400> SEQUENCE: 163
ccgcgggggg agggaacagc gttgatcacg tgacgtggtt tcagtgttta cacccgcagc       60
gggccggggg ttcggcctca gtcaggcgct cagctccgtt tcggtttcac ttccggtgga      120
gggccgcctc tgagcgggcg gcgggccgac ggcgagcgcg ggcggcggcg gtgacggagg      180
cgccgctgcc aggggggcgtg cggcagcgcg cggcggcgcgg cggcggcggc ggcggcggag      240
gcggcggcgg cggcggcggc ggcggcggct gggcctcgag cgcccgcagc ccacctctcg      300
ggggcgggct cccggcgcta g                                                321

<210> SEQ ID NO 164
<211> LENGTH: 723
<212> TYPE: DNA
<213> ORGANISM: Mus musculus

```
<400> SEQUENCE: 164
cacgaggcat acccagtag actcttacac tgaacctccc aatcctaact tagtacatgc    60
atacaataaa tgctcactaa gtactgatat atgattaaaa cacttgaaaa caaacaaact   120
gtaatgtaca tgacataatc gtgatgagca gtaagtagga acatcttctt ggcaaaggaa   180
ggagtcaaac aatgagcagg ggctgtgagt gtgggtcagt ggtagcacag catgcatgag   240
gccctatatt tggtctctag caacacacat aaaagatgaa caaaaccaga cagaggaaga   300
ggtatgtcga gagtcttaaa taaaacaggt cagatctaaa acaactttta ggagaaacag   360
aaagatactt actttcggtc actcccccaa tagcaagaga aataatagct aaaacgttct   420
cacatgcgga atgatttata atttcttctt ccagaacacc tctgaaagct tggtcaaggg   480
tacatttttt ttcattttca ctgccaggta actgactgaa ggcagtcaac aacggcttga   540 tattttttgtt attcaaggct tctctggtag atttcgtaaa tcgcgtccgc gcctccggca   600
aactgaaaag cgctttatca ggcgtcttcc cgcgccgcag tctctctgtt ctcccggttc   660
cttcgagctc gtcgtctctg ccgtcctctg acttttaatt ccaggacttg ccttctgcc    720 atg                                                                 723

<210> SEQ ID NO 165
<211> LENGTH: 83
<212> TYPE: DNA
<213> ORGANISM: Mus musculus

<400> SEQUENCE: 165
aaaacgttct cacatgcgga atgatttata atttcttctt ccagaacacc tctgaaagct    60
tggtcaaggg tacatttttt ttc                                            83

<210> SEQ ID NO 166
<211> LENGTH: 80
<212> TYPE: DNA
<213> ORGANISM: Mus musculus

<400> SEQUENCE: 166
acgttctcac atgcggaatg atttataatt tcttcttcca gaacacctct gaaagcttgg    60
tcaagggtac attttttttc                                                80

<210> SEQ ID NO 167
<211> LENGTH: 77
<212> TYPE: DNA
<213> ORGANISM: Mus musculus

<400> SEQUENCE: 167
ttctcacatg cggaatgatt tataatttct tcttccagaa cacctctgaa agcttggtca    60
agggtacatt tttttc                                                    77

<210> SEQ ID NO 168
<211> LENGTH: 74
<212> TYPE: DNA
<213> ORGANISM: Mus musculus

<400> SEQUENCE: 168
tcacatgcgg aatgatttat aatttcttct tccagaacac ctctgaaagc ttggtcaagg    60 gtacatttttt ttc                                                      74
```

```
<210> SEQ ID NO 169
<211> LENGTH: 71
<212> TYPE: DNA
<213> ORGANISM: Mus musculus

<400> SEQUENCE: 169
catgcggaat gatttataat ttcttcttcc agaacacctc tgaaagcttg gtcaagggta      60 cattttttt c                                                           71

<210> SEQ ID NO 170
<211> LENGTH: 69
<212> TYPE: DNA
<213> ORGANISM: Mus musculus

<400> SEQUENCE: 170
tgcggaatga tttataattt cttcttccag aacacctctg aaagcttggt caagggtaca      60
ttttttttc                                                             69

<210> SEQ ID NO 171
<211> LENGTH: 65
<212> TYPE: DNA
<213> ORGANISM: Mus musculus

<400> SEQUENCE: 171
gaatgattta aatttcttc ttccagaaca cctctgaaag cttggtcaag ggtacatttt       60
ttttc                                                                 65

<210> SEQ ID NO 172
<211> LENGTH: 62
<212> TYPE: DNA
<213> ORGANISM: Mus musculus

<400> SEQUENCE: 172
tgatttataa tttcttcttc cagaacacct ctgaaagctt ggtcaagggt acattttttt     60
tc                                                                    62

<210> SEQ ID NO 173
<211> LENGTH: 59
<212> TYPE: DNA
<213> ORGANISM: Mus musculus

<400> SEQUENCE: 173
tttataattt cttcttccag aacacctctg aaagcttggt caagggtaca tttttttc       59

<210> SEQ ID NO 174
<211> LENGTH: 58
<212> TYPE: DNA
<213> ORGANISM: Mus musculus

<400> SEQUENCE: 174
ttataatttc ttcttccaga acacctctga aagcttggtc aagggtacat tttttttc       58

<210> SEQ ID NO 175
<211> LENGTH: 57
<212> TYPE: DNA
<213> ORGANISM: Mus musculus

<400> SEQUENCE: 175
tataatttct tcttccagaa cacctctgaa agcttggtca agggtacatt ttttttc        57
```

<210> SEQ ID NO 176
<211> LENGTH: 53
<212> TYPE: DNA
<213> ORGANISM: Mus musculus

<400> SEQUENCE: 176
atttcttctt ccagaacacc tctgaaagct tggtcaaggg tacatttttt ttc    53

<210> SEQ ID NO 177
<211> LENGTH: 50
<212> TYPE: DNA
<213> ORGANISM: Mus musculus

<400> SEQUENCE: 177
tcttcttcca gaacacctct gaaagcttgg tcaagggtac attttttttc    50

<210> SEQ ID NO 178
<211> LENGTH: 47
<212> TYPE: DNA
<213> ORGANISM: Mus musculus

<400> SEQUENCE: 178
tcttccagaa cacctctgaa agcttggtca agggtacatt ttttttc    47

<210> SEQ ID NO 179
<211> LENGTH: 44
<212> TYPE: DNA
<213> ORGANISM: Mus musculus

<400> SEQUENCE: 179
tccagaacac ctctgaaagc ttggtcaagg gtacattttt tttc    44

<210> SEQ ID NO 180
<211> LENGTH: 42
<212> TYPE: DNA
<213> ORGANISM: Mus musculus

<400> SEQUENCE: 180
cagaacacct ctgaaagctt ggtcaagggt acatttttt tc    42

<210> SEQ ID NO 181
<211> LENGTH: 62
<212> TYPE: DNA
<213> ORGANISM: Mus musculus

<400> SEQUENCE: 181
tgatttataa tttcttcttc caaaaaaaaa aaaaaaaaa aaaaaaaaa aaaaaaaaa    60 aa    62

<210> SEQ ID NO 182
<211> LENGTH: 62
<212> TYPE: DNA
<213> ORGANISM: Mus musculus

<400> SEQUENCE: 182
tgatttataa tttcttcttc cagaaaaaaa aaaaaaaaa aaaaaaaaa aaaaaaaaa    60 aa    62

<210> SEQ ID NO 183
<211> LENGTH: 62
<212> TYPE: DNA
<213> ORGANISM: Mus musculus

```
<400> SEQUENCE: 183
tgatttataa tttcttcttc cagaacacaa aaaaaaaaaa aaaaaaaaaa aaaaaaaaaa    60
aa                                                                  62

<210> SEQ ID NO 184
<211> LENGTH: 62
<212> TYPE: DNA
<213> ORGANISM: Mus musculus

<400> SEQUENCE: 184
tgatttataa tttcttcttc cagaacacct caaaaaaaaa aaaaaaaaaa aaaaaaaaaa    60
aa                                                                  62

<210> SEQ ID NO 185
<211> LENGTH: 62
<212> TYPE: DNA
<213> ORGANISM: Mus musculus

<400> SEQUENCE: 185
tgatttataa tttcttcttc cagaacacct ctgaaaaaaa aaaaaaaaaa aaaaaaaaaa    60
aa                                                                  62

<210> SEQ ID NO 186
<211> LENGTH: 62
<212> TYPE: DNA
<213> ORGANISM: Mus musculus

<400> SEQUENCE: 186
tgatttataa tttcttcttc cagaacacct ctgaaagcta aaaaaaaaaa aaaaaaaaaa    60
aa                                                                  62

<210> SEQ ID NO 187
<211> LENGTH: 62
<212> TYPE: DNA
<213> ORGANISM: Mus musculus

<400> SEQUENCE: 187
tgatttataa tttcttcttc cagaacacct ctgaaagctt aaaaaaaaaa aaaaaaaaaa    60
aa                                                                  62

<210> SEQ ID NO 188
<211> LENGTH: 62
<212> TYPE: DNA
<213> ORGANISM: Mus musculus

<400> SEQUENCE: 188
tgatttataa tttcttcttc cagaacacct ctgaaagctt gaaaaaaaaa aaaaaaaaaa    60
aa                                                                  62

<210> SEQ ID NO 189
<211> LENGTH: 62
<212> TYPE: DNA
<213> ORGANISM: Mus musculus

<400> SEQUENCE: 189
tgatttataa tttcttcttc cagaacacct ctgaaagctt ggaaaaaaaa aaaaaaaaaa    60
aa                                                                  62
```

```
<210> SEQ ID NO 190
<211> LENGTH: 62
<212> TYPE: DNA
<213> ORGANISM: Mus musculus

<400> SEQUENCE: 190
tgatttataa tttcttcttc cagaacacct ctgaaagctt ggtcaagaaa aaaaaaaaaa      60
aa                                                                    62

<210> SEQ ID NO 191
<211> LENGTH: 22
<212> TYPE: DNA
<213> ORGANISM: Mus musculus

<400> SEQUENCE: 191 tttataatttt caacaaccag aa                                             22

<210> SEQ ID NO 192
<211> LENGTH: 9
<212> TYPE: DNA
<213> ORGANISM: Mus musculus

<400> SEQUENCE: 192 gaaagcttg                                                              9

<210> SEQ ID NO 193
<211> LENGTH: 15
<212> TYPE: DNA
<213> ORGANISM: Mus musculus

<400> SEQUENCE: 193 ggtacattttt ttttc                                                     15

<210> SEQ ID NO 194
<211> LENGTH: 19
<212> TYPE: DNA
<213> ORGANISM: Mus musculus

<400> SEQUENCE: 194
atgcgggaat gatttataa                                                  19

<210> SEQ ID NO 195
<211> LENGTH: 1798
<212> TYPE: DNA
<213> ORGANISM: Saccharomyces cerevisiae

<400> SEQUENCE: 195
tatctggttg atcctgccag tagtcatatg cttgtctcaa agattaagcc atgcatgtct      60
aagtataagc aatttataca gtgaaactgc gaatggctca ttaaatcagt tatcgtttat     120
ttgatagttc ctttactaca tggtataacc gtggtaattc tagagctaat acatgcttaa     180
aatctcgacc ctttggaaga gatgtattta ttagataaaa aatcaatgtc ttcgcactct     240
ttgatgattc ataataactt ttcgaatcgc atggccttgt gctggcgatg gttcattcaa     300
atttctgccc tatcaacttt cgatggtagg atagtggcct accatggttt caacgggtaa     360
cggggaataa gggttcgatt ccggagaggg agcctgagaa acggctacca catccaagga     420
aggcagcagg cgcgcaaatt acccaatcct aattcaggga ggtagtgaca ataaataacg     480
atacagggcc cattcgggtc ttgtaattgg aatgagtaca atgtaaatac cttaacgagg     540
aacaattgga gggcaagtct ggtgccagca gccgcggtaa ttccagctcc aatagcgtat     600
```

```
attaaagttg ttgcagttaa aaagctcgta gttgaacttt gggcccggtt ggccggtccg    660
atttttcgt gtactggatt tccaacgggg cctttccttc tggctaacct tgagtccttg     720
tggctcttgg cgaaccagga cttttacttt gaaaaaatta gagtgttcaa agcaggcgta    780
ttgctcgaat atattagcat ggaataatag aataggacgt tggttctat tttgttggtt     840
tctaggacca tcgtaatgat taataggac ggtcggggc atcggtattc aattgtcgag      900
gtgaaattct tggatttatt gaagactaac tactgcgaaa gcatttgcca aggacgtttt    960
cattaatcaa gaacgaaagt tagggatcg aagatgatct ggtaccgtcg tagtcttaac    1020
cataaactat gccgactaga tcgggtggtg ttttttaat gacccactcg gtaccttacg    1080
agaaatcaaa gtctttgggt tctgggggga gtatggtcgc aaggctgaaa cttaaaggaa   1140
ttgacggaag gcaccacta ggagtggagc ctgcggctaa tttgactcaa cacggggaaa    1200
ctcaccaggt ccagacacaa taaggattga cagattgaga gctctttctt gattttgtgg   1260
gtggtggtgc atggccgttt ctcagttggt ggagtgattt gtctgcttaa ttgcgataac   1320
gaacgagacc ttaacctact aaatagtggt gctagcattt gctggttatc cacttcttag   1380
agggactatc ggtttcaagc cgatggaagt ttgaggcaat aacaggtctg tgatgccctt   1440
agaacgttct gggccgcacg cgcgctacac tgacggagcc agcgagtcta accttggccg   1500
agaggtcttg gtaatcttgt gaaactccgt cgtgctgggg atagagcatt gtaattattg   1560
ctcttcaacg aggaattcct agtaagcgca agtcatcagc ttgcgttgat tacgtccctg   1620
ccctttgtac acaccgcccg tcgctagtac cgattgaatg gcttagtgag gcctcaggat   1680
ctgcttagag aaggggcaa ctccatctca gagcggagaa tttggacaaa cttggtcatt    1740
tagaggaact aaaagtcgta acaaggtttc cgtaggtgaa cctgcggaag gatcatta    1798
```

<210> SEQ ID NO 196
<211> LENGTH: 1869
<212> TYPE: DNA
<213> ORGANISM: Mus musculus

<400> SEQUENCE: 196

```
tacctggttg atcctgccag tagcatatgc ttgtctcaaa gattaagcca tgcatgtcta     60
agtacgcacg gccggtacag tgaaactgcg aatggctcat taaatcagtt atggttcctt    120
tggtcgctcg ctcctctcct acttggataa ctgtggtaat tctagagcta atacatgccg    180
acgggcgctg acccccttc ccggggggg atgcgtgcat ttatcagatc aaaaccaacc      240
cggtgagctc cctcccggct ccggccgggg gtcgggcgcc ggcggcttgg tgactctaga    300
taacctcggg ccgatcgcac gcccccgtg gcggcgacga cccattcgaa cgtctgccct    360
atcaactttc gatggtagtc gccgtgccta ccatggtgac cacgggtgac ggggaatcag    420
ggttcgattc cggagaggga gcctgagaaa cggctaccac atccaaggaa ggcagcaggc    480
gcgcaaatta cccactcccg acccgggag gtagtgacga aaataacaa tacaggactc      540
tttcgaggcc ctgtaattgg aatgagtcca ctttaaatcc tttaacgagg atccattgga    600
gggcaagtct ggtgccagca gccgcggtaa ttccagctcc aatagcgtat attaaagttg    660
ctgcagttaa aaagctcgta gttggatctt gggagcgggc gggcggtccg ccgcgaggcg    720
agtcaccgcc cgtccccgcc ccttgcctct cggcgcccc tcgatgctct agctgagtg     780
tcccgcgggg cccgaagcgt ttactttgaa aaaattagag tgttcaaagc aggcccgagc    840
cgcctggata ccgcagctag gaataatgga ataggaccgc ggttctattt tgttggtttt    900
cggaactgag gccatgatta gagggacgg ccgggggcat tcgtattgcg ccgctagagg     960
```

```
tgaaattctt ggaccggcgc aagacggacc agagcgaaag catttgccaa gaatgttttc    1020
attaatcaag aacgaaagtc ggaggttcga agacgatcag ataccgtcgt agttccgacc    1080
ataaacgatg ccgactggcg atgcggcggc gttattccca tgacccgccg ggcagcttcc    1140
gggaaaccaa agtctttggg ttccgggggg agtatggttg caaagctgaa acttaaagga    1200
attgacggaa gggcaccacc aggagtgggc ctgcggctta atttgactca acacgggaaa    1260
cctcacccgg cccggacacg gacaggattg acagattgat agctctttct cgattccgtg    1320
ggtggtggtg catggccgtt cttagttggt ggagcgattt gtctggttaa ttccgataac    1380
gaacgagact ctggcatgct aactagttac gcgaccccg agcggtcggc gtcccccaac     1440
ttcttagagg acaagtggc gttcagccac ccgagattga gcaataacag gtctgtgatg     1500
cccttagatg tccggggctg cacgcgcgct acactgactg gctcagcgtg tgcctaccct    1560
gcgccggcag gcgcgggtaa cccgttgaac cccattcgtg atggggatcg gggattgcaa    1620
ttattcccca tgaacgagga attcccagta agtgcgggtc ataagcttgc gttgattaag    1680
tccctgccct ttgtacacac cgcccgtcgc tactaccgat tggatggttt agtgaggccc    1740
tcggatcggc cccgccgggg tcggcccacg gccctggcgg agcgctgaga agacggtcga    1800
acttgactat ctagaggaag taaaagtcgt aacaaggttt ccgtaggtga acctgcggaa    1860
ggatcatta                                                           1869

<210> SEQ ID NO 197
<211> LENGTH: 1869
<212> TYPE: DNA
<213> ORGANISM: Homo sapiens
<220> FEATURE:
<221> NAME/KEY: modified_base
<222> LOCATION: (27)..(27)
<223> OTHER INFORMATION: m2a--2'-o-methyladenosine (genebank # 36162)
<220> FEATURE:
<221> NAME/KEY: modified_base
<222> LOCATION: (99)..(99)
<223> OTHER INFORMATION: m2a--2'-o-methyladenosine
<220> FEATURE:
<221> NAME/KEY: modified_base
<222> LOCATION: (159)..(159)
<223> OTHER INFORMATION: m2a--2'-o-methyladenosine
<220> FEATURE:
<221> NAME/KEY: modified_base
<222> LOCATION: (166)..(166)
<223> OTHER INFORMATION: m2a--2'-o-methyladenosine
<220> FEATURE:
<221> NAME/KEY: modified_base
<222> LOCATION: (468)..(468)
<223> OTHER INFORMATION: m2a--2'-o-methyladenosine
<220> FEATURE:
<221> NAME/KEY: modified_base
<222> LOCATION: (484)..(484)
<223> OTHER INFORMATION: m2a--2'-o-methyladenosine
<220> FEATURE:
<221> NAME/KEY: modified_base
<222> LOCATION: (512)..(512)
<223> OTHER INFORMATION: m2a--2'-o-methyladenosine
<220> FEATURE:
<221> NAME/KEY: modified_base
<222> LOCATION: (576)..(576)
<223> OTHER INFORMATION: m2a--2'-o-methyladenosine
<220> FEATURE:
<221> NAME/KEY: modified_base
<222> LOCATION: (590)..(590)
<223> OTHER INFORMATION: m2a--2'-o-methyladenosine
<220> FEATURE:
<221> NAME/KEY: modified_base
<222> LOCATION: (668)..(668)
<223> OTHER INFORMATION: m2a--2'-o-methyladenosine
```

```
<220> FEATURE:
<221> NAME/KEY: modified_base
<222> LOCATION: (1031)..(1031)
<223> OTHER INFORMATION: m2a--2'-o-methyladenosine
<220> FEATURE:
<221> NAME/KEY: modified_base
<222> LOCATION: (1383)..(1383)
<223> OTHER INFORMATION: m2a--2'-o-methyladenosine
<220> FEATURE:
<221> NAME/KEY: modified_base
<222> LOCATION: (1678)..(1678)
<223> OTHER INFORMATION: m2a--2'-o-methyladenosine
<220> FEATURE:
<221> NAME/KEY: modified_base
<222> LOCATION: (1832)..(1832)
<223> OTHER INFORMATION: m2a--2'-o-methyladenosine
<220> FEATURE:
<221> NAME/KEY: modified_base
<222> LOCATION: (1850)..(1850)
<223> OTHER INFORMATION: m2a--2'-o-methyladenosine
<220> FEATURE:
<221> NAME/KEY: modified_base
<222> LOCATION: (116)..(116)
<223> OTHER INFORMATION: um
<220> FEATURE:
<221> NAME/KEY: modified_base
<222> LOCATION: (121)..(121)
<223> OTHER INFORMATION: um
<220> FEATURE:
<221> NAME/KEY: modified_base
<222> LOCATION: (172)..(172)
<223> OTHER INFORMATION: um
<220> FEATURE:
<221> NAME/KEY: modified_base
<222> LOCATION: (428)..(428)
<223> OTHER INFORMATION: um
<220> FEATURE:
<221> NAME/KEY: modified_base
<222> LOCATION: (627)..(627)
<223> OTHER INFORMATION: um
<220> FEATURE:
<221> NAME/KEY: modified_base
<222> LOCATION: (799)..(799)
<223> OTHER INFORMATION: um
<220> FEATURE:
<221> NAME/KEY: modified_base
<222> LOCATION: (1288)..(1288)
<223> OTHER INFORMATION: um
<220> FEATURE:
<221> NAME/KEY: modified_base
<222> LOCATION: (1326)..(1326)
<223> OTHER INFORMATION: um
<220> FEATURE:
<221> NAME/KEY: modified_base
<222> LOCATION: (1442)..(1442)
<223> OTHER INFORMATION: um
<220> FEATURE:
<221> NAME/KEY: modified_base
<222> LOCATION: (1668)..(1668)
<223> OTHER INFORMATION: um
<220> FEATURE:
<221> NAME/KEY: modified_base
<222> LOCATION: (1804)..(1804)
<223> OTHER INFORMATION: um
<220> FEATURE:
<221> NAME/KEY: modified_base
<222> LOCATION: (174)..(174)
<223> OTHER INFORMATION: cm 2'-o-cytidine
<220> FEATURE:
<221> NAME/KEY: modified_base
<222> LOCATION: (462)..(462)
<223> OTHER INFORMATION: cm
<220> FEATURE:
<221> NAME/KEY: modified_base
<222> LOCATION: (517)..(517)
<223> OTHER INFORMATION: cm
```

```
<220> FEATURE:
<221> NAME/KEY: modified_base
<222> LOCATION: (797)..(797)
<223> OTHER INFORMATION: cm
<220> FEATURE:
<221> NAME/KEY: modified_base
<222> LOCATION: (1391)..(1391)
<223> OTHER INFORMATION: cm
<220> FEATURE:
<221> NAME/KEY: modified_base
<222> LOCATION: (1703)..(1703)
<223> OTHER INFORMATION: cm
<220> FEATURE:
<221> NAME/KEY: modified_base
<222> LOCATION: (436)..(436)
<223> OTHER INFORMATION: gm
<220> FEATURE:
<221> NAME/KEY: modified_base
<222> LOCATION: (509)..(509)
<223> OTHER INFORMATION: gm
<220> FEATURE:
<221> NAME/KEY: modified_base
<222> LOCATION: (601)..(601)
<223> OTHER INFORMATION: gm
<220> FEATURE:
<221> NAME/KEY: modified_base
<222> LOCATION: (644)..(644)
<223> OTHER INFORMATION: gm
<220> FEATURE:
<221> NAME/KEY: modified_base
<222> LOCATION: (683)..(683)
<223> OTHER INFORMATION: gm
<220> FEATURE:
<221> NAME/KEY: modified_base
<222> LOCATION: (867)..(867)
<223> OTHER INFORMATION: gm
<220> FEATURE:
<221> NAME/KEY: modified_base
<222> LOCATION: (1328)..(1328)
<223> OTHER INFORMATION: gm
<220> FEATURE:
<221> NAME/KEY: modified_base
<222> LOCATION: (1447)..(1447)
<223> OTHER INFORMATION: gm
<220> FEATURE:
<221> NAME/KEY: modified_base
<222> LOCATION: (1490)..(1490)
<223> OTHER INFORMATION: gm
<220> FEATURE:
<221> NAME/KEY: modified_base
<222> LOCATION: (1639)..(1639)
<223> OTHER INFORMATION: gm
<220> FEATURE:
<221> NAME/KEY: modified_base
<222> LOCATION: (1248)..(1248)
<223> OTHER INFORMATION: x 3-(3-amino-3-carboxypropyl)
      -1-methylpseudouridine

<400> SEQUENCE: 197
tacctggttg atcctgccag tagcatatgc ttgtctcaaa gattaagcca tgcatgtcta      60
agtacgcacg gccggtacag tgaaactgcg aatggctcat taaatcagtt atggttcctt    120
tggtcgctcg ctcctctccc acttggataa ctgtggtaat tctagagcta atacatgccg    180
acgggcgctg accccctttcg cggggggggat gcgtgcattt atcagatcaa aaccaacccg    240
gtcagcccct ctccggcccc ggccgggggg cgggcgccgg cggctttggt gactctagat    300
aacctcgggc cgatcgcacg ccccccgtgg cggcgacgac ccattcgaac gtctgcccta    360
tcaactttcg atggtagtcg ccgtgcctac catggtgacc acgggtgacg gggaatcagg    420
gttcgattcc ggagagggag cctgagaaac ggctaccaca tccaaggaag gcagcaggcg    480 cgcaaaattac ccactcccga cccggggagg tagtgacgaa aaataacaat acaggactct    540
ttcgaggccc tgtaattgga atgagtccac tttaaatcct ttaacgagga tccattggag    600
```

```
                                                          -continued
ggcaagtctg gtgccagcag ccgcggtaat tccagctcca atagcgtata ttaaagttgc    660
tgcagttaaa aagctcgtag ttggatcttg ggagcgggcg ggcggtccgc cgcgaggcga    720
gccaccgccc gtccccgccc cttgcctctc ggcgccccct cgatgctctt agctgagtgt    780 cccgcgggc  ccgaagcgtt tactttgaaa aaattagagt gttcaaagca ggcccgagcc    840
gcctggatac cgcagctagg aataatggaa taggaccgcg gttctatttt gttggttttc    900
ggaactgagg ccatgattaa gagggacggc cgggggcatt cgtattgcgc cgctagaggt    960
gaaattcttg gaccggcgca agacggacca gagcgaaagc atttgccaag aatgttttca   1020
ttaatcaaga acgaaagtcg gaggttcgaa gacgatcaga taccgtcgta gttccgacca   1080
taaacgatgc cgaccggcga tgcggcggcg ttattcccat gacccgccgg gcagcttccg   1140
ggaaaccaaa gtctttgggt tccgggggga gtatggttgc aaagctgaaa cttaaaggaa   1200
ttgacggaag ggcaccacca ggagtggagc ctgcggctta atttgactca acacgggaaa   1260
cctcacccgg cccggacacg gacaggattg acagattgat agctctttct cgattccgtg   1320
ggtggtggtg catggccgtt cttagttggt ggagcgattt gtctggttaa ttccgataac   1380
gaacgagact ctggcatgct aactagttac gcgaccccg  agcggtcggc gtcccccaac   1440
ttcttagagg gacaagtggc gttcagccac ccgagattga gcaataacag gtctgtgatg   1500
cccttagatg tccggggctg cacgcgcgct acactgactg gctcagcgtg tgcctaccct   1560
acgccggcag gcgcgggtaa cccgttgaac cccattcgtg atggggatcg gggattgcaa   1620
ttattcccca tgaacgagga attcccagta agtgcgggtc ataagcttgc gttgattaag   1680
tccctgccct ttgtacacac cgcccgtcgc tactaccgat tggatggttt agtgaggccc   1740
tcggatcggc cccgccgggg tcggcccacg gccctggcgg agcgctgaga agacggtcga   1800
acttgactat ctagaggaag taaaagtcgt aacaaggttt ccgtaggtga acctgcggaa   1860
ggatcatta                                                          1869
```

SYNTHETIC INTERNAL RIBOSOME ENTRY SITES AND METHODS OF IDENTIFYING SAME

This application claims the benefit of priority under 35 U.S.C. § 119(e) of U.S. Ser. No. 60/230,956, filed Sep. 7, 2000; U.S. Ser. No. 60/230,852, filed Sep. 7, 2000; U.S. Ser. No. 60/207,804, filed May 30, 2000; U.S. Ser. No. 60/186,496, filed Mar. 2, 2000; U.S. Ser. No. 60/178,816, filed Jan. 28, 2000; and U.S. Ser. No. 60/261,312, filed Jan. 12, 2001, each of which is incorporated herein by reference.

This invention was made in part with government support under Grant No. MCB9982574 awarded by the National Science Foundation. The government has certain rights in this invention.

BACKGROUND OF THE INVENTION

1. Field of the Invention

The present invention relates generally to compositions for modulating the level of translation of a polypeptide, and more specifically to synthetic internal ribosome entry site (IRES) nucleotide sequence and to methods of identifying a synthetic IRES.

2. Background Information

Molecular biology provides tools for genetically engineering organisms to express large amounts of useful gene products, including new and useful gene products. As such, medically useful gene products such as growth factors, hormones, and immunoregulatory polypeptides, for example, interferons and interleukins are now available in sufficient quantities for therapeutic use. In addition, molecular biology has allowed gene therapy to evolve to a form that it promises to provide new ways for doctors to manage previously untreatable conditions.

Although molecular biology currently provides tools for expressing recombinant proteins in the cells of bacteria, plants, and animals, including human cells, methods for manipulating the amount of a protein that is expressed in the cells are limited. For example, the recombinant protein can be expressed from a particular gene promoter, that has a known level of activity or that is expressed only in one or a few cell types. However, while the use of a particular promoter may result in the expression of a particular amount of RNA encoding the protein, the amount of protein translated from the RNA does not always correlate directly with the amount of RNA that is expressed. For example, some of the RNA may be degraded in the particular cell, or the RNA may not be translated efficiently. In other cases, the protein may be translated in an amount that is toxic, either to the cell expressing the protein or to another cell that is in proximity to a cell that produces and secretes the protein.

Nucleotide sequences that are involved in regulating the translation of a polypeptide have been described, and can be utilized to help regulate the amount of a protein translated from an RNA molecule. Some of these nucleotide sequences are functional only when positioned at the 5' end of an RNA molecule, and are useful for regulating the expression of a protein encoded by the nucleotide immediately downstream of the translation regulatory element. However, such nucleotide sequences are not useful for regulating the expression of a number of proteins that are encoded by a single RNA molecule containing a series of open reading frames. For this purpose, nucleotide sequences that can regulate translation from within a nucleotide sequence can be useful. However, only a few such sequences, referred to as internal ribosome binding sites (IRES), have been described, and they generally are very large, containing more than a hundred, generally several hundred, nucleotides.

The large size of the known IRES sequences limits their usefulness. For example, many gene therapy vectors such as retrovirus vectors are limited in the size of a polynucleotide insert that can be contained in and expressed from the vector. As such, polynucleotides that encode very large proteins cannot be used with certain vectors. The use of an IRES, which can consist of several hundred nucleotides, only further limits the size of the encoding polynucleotide that can be included in the vector, thus further limiting the polynucleotides that can be used in a gene therapy procedure. Furthermore, the use of a single IRES may not result in sufficient expression of a desired polypeptide. Thus, a need exists for regulatory elements that are useful for modulating the level of protein expression. The present invention satisfies this need and provides additional advantages.

SUMMARY OF THE INVENTION

The present invention relates to an isolated synthetic translational regulatory element, which includes at least one oligonucleotide consisting of about 6 to 125 ribonucleotides, or a deoxyribonucleotide sequence encoding the oligonucleotide. The oligonucleotide is characterized, in part, in having translational regulatory activity, for example, translational enhancing activity, translational inhibitory activity, internal ribosome entry site (IRES) activity or a combination thereof, and has such translational regulatory activity in a eukaryotic cell.

A synthetic translational regulatory element of the invention is exemplified herein by an oligonucleotide encoded by any of SEQ ID NOS: 42 to 46, 49, 50, 52, and 89 to 160, which were identified by screening libraries of randomized oligonucleotides. In addition, a synthetic translational regulatory element is exemplified herein by an oligonucleotide that is complementary to an oligonucleotide sequence of a ribosomal RNA, particularly to an oligonucleotide sequence of an un-base paired region of ribosomal RNA, for example, an oligonucleotide encoded by any of SEQ ID NOS: 2, 30, 32, 34, 36, 38, 40 and 50.

A synthetic translational regulatory element of the invention can contain two or more oligonucleotides having translational regulatory activity, wherein the oligonucleotides are operatively linked to each other, and can be the same or different Examples of such synthetic translational regulatory elements include those encoded by a nucleotide sequence selected from any of SEQ ID NOS: 42 to 46, 49, 50, 52, and 89 to 160. In one embodiment, a synthetic translational regulatory element contains five operatively linked oligonucleotides having translational regulatory activity. In another embodiment, a synthetic translational regulatory element contains ten operatively linked oligonucleotides having translational regulatory activity. In still another embodiment, a synthetic translational regulatory element contains up to fifty operatively linked oligonucleotides having translational regulatory activity. Such oligonucleotides in a synthetic translational regulatory element can be adjacent to each other, or can be separated from each other by a spacer nucleotide sequence, which can consist of about 1 to 100 ribonucleotides, for example, the synthetic translational regulatory elements encoded by any of SEQ ID NOS: 53 to 88.

The present invention also relates to a vector containing a synthetic translational regulatory element of the invention. In one embodiment, the vector is an expression vector, which can contain a translation initiation site in addition to the synthetic translational regulatory element, which can have, for example, translational enhancing activity. In addition, the vector can contain a translation start codon operatively linked to the translation initiation site. In another embodiment, the expression vector contains an expressible polynucleotide, wherein the translational regulatory element is operatively linked to the expressible polynucleotide, and wherein the translational regulatory element has transcriptional enhancing activity or IRES activity. The expressible polynucleotide can include one cistron or can be polycistronic, for example, dicistronic. Also provided is a host cell containing a synthetic translational regulatory element of the invention.

The present invention also relates to an isolated translational regulatory element, which includes at least one 5' untranslated region (5' UTR) of a eukaryotic messenger RNA (mRNA) or an oligonucleotide portion thereof, or a deoxyribonucleotide sequence encoding said 5' UTR or oligonucleotide portion thereof. The 5' UTR or oligonucleotide portion thereof is characterized, in part in having translational enhancing activity, internal ribosome entry site (IRES) activity or a combination thereof, and the translational regulatory activity is effective in a eukaryotic cell.

In one embodiment, the 5' UTR of an isolated translational regulatory element is encoded by a nucleotide sequence selected from any of SEQ ID NOS: 1, 23 to 29, 161, 162, and 164, and the 5' UTR or oligonucleotide portion thereof has translational enhancing activity or IRES activity or both. An oligonucleotide portion of a 5' UTR in such an isolated translational regulatory element is exemplified by an oligonucleotide encoded by any of nucleotides 1 to 40, 1 to 81, 1 to 120, 41 to 81, 14 to 196, 80 to 120, 80 to 196, 120, to 166, and 120 to 196 of a Gtx homeodomain 5' UTR (SEQ ID NO: 1). A particular oligonucleotide portion of the Gtx 5' UTR is shown as SEQ ID NO: 2, which can be linked at its upstream (5') end or downstream (3') end or both ends to a spacer nucleotide sequence, which can be about 1 to 100 ribonucleotides in length, for example, an oligonucleotide encoded by SEQ ID NOS: 4, 5, 12, and 20 to 22. An isolated translational regulatory element also can contain two or more oligonucleotide portions encoded by SEQ ID NO: 2, which are operatively linked to each other, for example, five or ten of the oligonucleotides in operative linkage, and each of the oligonucleotides (SEQ ID NO: 2) can, but need not, be separated from each other by a spacer nucleotide sequence. Examples of such isolated translational regulatory elements are encoded by any of SEQ ID NOS: 6 to 11 and 13 to 15.

Additional examples of an oligonucleotide portion of a 5' UTR having translational regulatory activity including oligonucleotide portions of the yeast YAP1 mRNA (SEQ ID NOS: 30 and 32), and oligonucleotide portions of the yeast p150 mRNA, including any of nucleotides 1 to 250, 100 to 508, 160 to 508, 250 to 508, 375 to 508, 429 to 508, 481 to 508, and 250 to 390 of SEQ ID NO: 29; or any of SEQ ID NOS: 36, 38 and 40. In addition, oligonucleotide sequences of the mouse Rbm3 mRNA, including any of SEQ ID NOS: 165 to 169, 171 to 176, and 182 to 192 have translational regulatory activity. An isolated translational regulatory element also can include at least two 5' UTRs or oligonucleotide portions thereof, wherein the at least two 5' UTRs or oligonucleotide portions are operatively linked to each other, and wherein each of the at least two 5' UTRs or oligonucleotide portions independently is the same or different from each other.

In another embodiment, an isolated translational regulatory element includes an oligonucleotide portion of a 5' UTR encoded by any of SEQ ID NOS: 1, 23 to 29, 161, 162, and 164, wherein said oligonucleotide portion thereof has translational inhibitory activity. Examples of such oligonucleotides having translational inhibitory activity include those encoded by nucleotides 120 to 196 and 167 to 196 of the Gtx homeodomain protein mRNA (SEQ ID NO: 1), those encoded by nucleotides 1 to 100 and 100 to 160 of the yeast p150 mRNA (SEQ ID NO: 29), the portion of the yeast p150 mRNA shown as SEQ ID NO: 34, and those encoded by SEQ ID NO: 193 and SEQ ID NO: 194, which encode portions of the mouse Rbm3 mRNA.

The present invention also relates to a kit, which contains a synthetic translational regulatory element or an isolated translational regulatory element of the invention. In particular, a kit of the invention can contain a plurality of synthetic transcriptional regulatory elements, which are the same as or different from each other, and which can contain a flanking sequence independently at a 5' end or a 3' end or both 5' and 3' ends, to facilitate operatively linking two or more synthetic translational regulatory elements in the plurality to each other.

The present invention further relates to a recombinant nucleic acid molecule, which contains a synthetic translational regulatory element operatively linked to an expressible polynucleotide. The expressible polynucleotide can comprise a cistron, and the synthetic translational regulatory element has translational enhancing activity or IRES activity. The expressible polynucleotide also can comprise, in operative linkage in a 5' to 3' orientation, a first cistron, a spacer nucleotide sequence, and a second cistron, and the synthetic translational regulatory element can have IRES activity, and be operatively linked to the second cistron. The synthetic translational regulatory element in a recombinant nucleic acid molecule of the invention can include two or more operatively linked oligonucleotides having translational regulatory activity.

The polypeptide encoded by a recombinant nucleic acid molecule of the invention can be any polypeptide. A polypeptide encoded by a recombinant nucleic acid molecule can be any other polypeptide, for example, a viral or bacterial polypeptide or an epitope expressed by a virus, bacterium or other pathogenic organism; or a growth factor, a hormone and a receptor for a growth factor or a hormone. The recombinant nucleic acid molecule also can encode two or more polypeptides.

A particularly useful polypeptide that can be expressed by a recombinant nucleic acid molecule of the invention, or that can be encoded by an expressible polynucleotide useful in a composition or method of the invention is a reporter molecule, which provides a means to detect, select or isolate, for example, a cell expressing the reporter polypeptide. Reporter molecules (polypeptides) are well known in the art and include, for example, fluorescent polypeptides such as green fluorescent protein, cyan fluorescent protein, red fluorescent protein, or enhanced forms thereof, an antibiotic resistance polypeptide such as puromycin N-acetyltransferase, hygromycin B phosphotransferase, neomycin (aminoglycoside) phosphotransferase, and the Sh ble gene product, a cell surface protein marker such as the cell surface protein marker is neural cell adhesion molecule (N-CAM), an enzyme such as β-galactosidase, chloramphenicol acetyltransferase, luciferase, and alkaline phosphatase, or a peptide tag such as a c-myc peptide, a polyhistidine, or the like.

Expression of a reporter molecule can be detected using the appropriate reagent, for example, by detecting fluorescence of a green fluorescent protein or light emission upon addition of luciferin to a luciferase reporter molecule, or by detecting binding of nickel ion to a polypeptide containing a polyhistidine tag. Furthermore, the reporter molecule can provide a means of isolating the expressed reporter molecule or a cell expressing the reporter molecule. For example, where the reporter molecule is a polypeptide that is expressed on a cell surface and that contains an operatively linked c-myc epitope, an anti-c-myc epitope antibody can be immobilized on a solid matrix and cells, some of which express the tagged polypeptide, can be contacted with the matrix under conditions that allow selective binding of the antibody to the epitope. Unbound cells can be removed by washing the matrix, and bound cells, which express the reporter molecule, can be eluted and collected. Methods for detecting such reporter molecules and for isolating the molecules, or cells expressing the molecules, are well known to those in the art (see, for example, Hopp et al., *BioTechnology* 6:1204, 1988; U.S. Pat. No. 5,011,912; each of which is incorporated herein by reference).

The present invention also relates to a method of producing a genetically modified cell that exhibits altered expression of a polypeptide. The method can be performed, for example, by introducing a synthetic translational regulatory element of the invention into a cell, whereby the synthetic translational regulatory element operatively linked to a nucleotide sequence encoding a polypeptide, thereby producing a genetically modified cell that exhibits altered expression of a polypeptide. In one embodiment, the synthetic translational regulatory element is operatively linked to the nucleotide sequence prior to introducing the synthetic translational regulatory element into the cell, wherein the synthetic translational regulatory element has translational enhancing activity or IRES activity. The polypeptide can be any polypeptide, for example, a reporter polypeptide, is a toxin, or a therapeutic agent. The synthetic translational regulatory element can be stably maintained in the cell, for example, by integration into the cell genome.

In another embodiment, the nucleotide sequence to which the synthetic translational regulatory element is operatively linked is a sequence of an endogenous gene in the cell genome. The synthetic translational regulatory element can have translational inhibitory activity, translational enhancing activity or IRES activity. Accordingly, the present invention also relates to a genetically modified eukaryotic cell produced by a method of the invention, as well as to a transgenic non-human eukaryotic organism containing or derived from such a genetically modified cell, a cell or tissue obtained from the transgenic non-human eukaryotic organism, and a cDNA or genomic DNA library prepared from the transgenic non-human eukaryotic organism or from a cell or tissue obtained from said transgenic non-human eukaryotic organism.

The present invention further provides a method of altering translational activity in a eukaryotic cell, the method comprising introducing into the cell a synthetic translational regulatory element, whereby the synthetic translational regulatory element interacts with a translation regulatory factor in the cell, thereby altering translational activity in the eukaryotic cell. In addition, the invention provides a method of altering translational activity in a eukaryotic cell, the method comprising introducing into the cell an isolated translational regulatory element, whereby the synthetic translational regulatory element interacts with a translation regulatory factor in the cell, thereby altering translational activity in the eukaryotic cell. The translational regulatory element can have translational enhancing activity or IRES activity, whereby translational activity in the cell is decreased, or can have translational inhibitory activity, whereby translational activity in the cell is decreased.

The present invention also provides a method of improving protein yield by a eukaryotic cell. Such a method can be performed, for example, by introducing into the cell a recombinant nucleic acid molecule containing a translational regulatory element operatively linked to an expressible polynucleotide, and expressing a polypeptide encoded by the expressible polynucleotide in the cell. The translational regulatory element generally has translational enhancing activity or IRES activity. In one embodiment, the expressible polynucleotide comprises a first cistron encoding a polypeptide that enhances protein stability or cell viability, and can also comprises a second cistron, which can encode any polypeptide of interest. Where the expressible polynucleotide contains two, or more, cistrons, the second, and other, cistron is operatively linked to the first cistron. Preferably, such an expressible polynucleotide contains one or more IRES elements, which can be operatively linked to the first cistron or the second or other cistrons or to all of the cistrons, and can be operatively linked to each other to form a concatemer of IRES elements. In such a method, the polypeptide that enhances protein stability or cell viability can be any polypeptide, for example, a chaperone protein, a heat shock protein, a protein having anti-oxidant activity, a protease inhibitor, a phosphatase inhibitor, a caspase inhibitor, or an antibiotic peptide such as a magainin, a defensin, or a cryptdin.

In another embodiment, the expressible polynucleotide comprises a first cistron encoding a polypeptide that enhances transcription or translation of a polynucleotide in the cell, for example, a transcription factor or a translation regulatory factor such as eukaryotic initiation factor or ribosomal protein or the like. The expressible polynucleotide also can comprise a second operatively linked cistron encoding a polypeptide of interest, which can be under the control of an IRES element of the invention, and the polypeptide that enhances transcription or translation of a polynucleotide can be a polypeptide that enhances transcription or translation of the expressible polynucleotide.

The present invention further relates to a method of expressing a polypeptide in a eukaryotic cell. Such a method can be performed, for example, by introducing into the cell a recombinant nucleic acid molecule comprising a translational regulatory element operatively linked to an expressible polynucleotide, wherein the translational regulatory element has an activity selected from translational enhancing activity and IRES activity, and expressing the expressible polynucleotide in the cell. The expressible polynucleotide can comprise a first cistron encoding a therapeutic polypeptide or a reporter polypeptide, which can be useful as a diagnostic agent. A therapeutic polypeptide can be, for example, an immunomodulator such as a cytokine, a neuromodulator, a hormone such as preproinsulin, a growth factor such as epidermal growth factor, a growth factor receptor such as a PDGF receptor, an apoptotic polypeptide such as Bax, an anti-apoptotic polypeptide such as Bcl-2, or an antibiotic. The expressible polynucleotide also can contain a second cistron encoding a polypeptide that facilitates expression of the therapeutic or diagnostic polypeptide or that facilitates activity of the therapeutic polypeptide. A polypeptide that facilitates expression or activity of such a polypeptide can be, for example, a transcription factor, which can increase transcription of the expressible polynucleotide; a translational regulatory factor, which can increase translation of the encoded polypeptide; a chaperone protein, a protein having anti-oxidant activity, a protease inhibitor, or a phosphatase inhibitor.

According to a method of the invention, the expressible polynucleotide can be introduced into a cell ex vivo, for example, into a cell in culture, or can be introduced into a cell in vivo in a eukaryotic organism, including a mammalian organism such as a human. As such, the recombinant nucleic acid molecule can be contained in a vector, which can be a plasmid vector or a viral vector such as an adenovirus vector, an adeno-associated virus vector, or a retrovirus vector. Such a method can be useful for treating or diagnosing a pathologic condition, or to monitor the progression of a pathologic condition.

The present invention also relates to a method of identifying a cell. Such a method can be performed by introducing into the cell a recombinant nucleic acid molecule comprising a translational regulatory element of the invention operatively linked to an expressible polynucleotide, wherein the translational regulatory element has an activity selected from translational enhancing activity and IRES activity, wherein the expressible polynucleotide comprises at least one cistron, which encodes a first reporter polypeptide, and wherein expression of the reporter polypeptide in the cell provides a means to identify the cell. If desired, the expressible polynucleotide also can contain a second cistron encoding a polypeptide of interest, in which case the second cistron is operatively linked to the first cistron, and the expressible polynucleotide also contains a synthetic IRES element of the invention, which can be operatively linked to the first cistron or the second cistron or both. The polypeptide of interest can be any polypeptide, including a second reporter polypeptide, which can be the same as or different from the first reporter polypeptide.

A method of identifying a cell as disclosed herein can further include a step of isolating a cell expressing a reporter polypeptide. In one embodiment, the step of isolating utilizes a reporter polypeptide expressed from the expressible polynucleotide. Thus, the reporter polypeptide can be, for example, a cell surface marker, wherein isolating the cell expressing the cell surface marker utilizes an antibody that specifically binds the cell surface marker. A cell surface marker can be a polypeptide that is normally expressed on a cell surface, for example, N-CAM, and the antibody can be an anti-N-CAM antibody, or the cell surface marker can comprise a peptide tag, which is expressed as part of a cell surface protein, in which case the cell can be isolated using an antibody specific for the cell surface protein, or an antibody or other ligand specific for the peptide tag. Accordingly, the present invention also provides an isolated cell obtained according to a method of the invention.

BRIEF DESCRIPTION OF THE FIGURES

FIG. 3 shows regions of complementarity between sequences of yeast 18S ribosomal RNA (SEQ ID NOS: 31, 33, 35, 37 and 39) and oligonucleotide portions of the yeast YAP1 5' UTR (SEQ ID NOS: 30 and 32) or the yeast p150 5' UTR (SEQ ID NOS: 34, 36, 38 and 40). Nucleotide sequences of the yeast YAP1 5' UTR (SEQ ID NO: 28), yeast p150 5' UTR (SEQ ID NO: 29), and 18S ribosomal RNA are indicated.

FIG. 7A provides a linear representation of the 18S rRNA, the vertical lines below the linear representation are sites at which selected IRES modules share 8 or 9 nucleotides of complementarity with the to 18S rRNA sequence.

FIG. 7B shows a secondary structure of the 18S rRNA, and the dark bars indicate the positions of the complementary sequence matches to selected IRES modules of the invention.

DETAILED DESCRIPTION OF THE INVENTION

Figure 1:
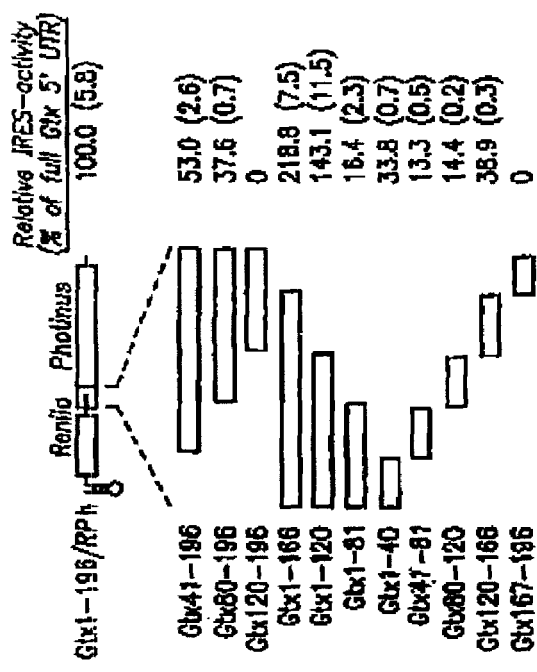
FIG. 1 illustrates the structure of Gtx (SEQ ID NO: 1) deletion constructs used to identify sequences having translational regulatory activity, and shows the relative IRES activity as determined using the RPh construct (see Example 1). Gtx1-196/RPh indicates a portion of the RPh plasmid containing a nucleotide sequence encoding the 196 nucleotide Gtx 5' untranslated region (5' UTR). Nucleotides included in the various constructs are indicated. Relative IRES activity is shown as a percent of the activity of the full length Gtx 5' UTR. Numbers in parentheses indicate standard error.

The present invention provides a synthetic translational regulatory element, which includes at least one oligonucleotide consisting of about 6 to 125 ribonucleotides, or a deoxyribonucleotide sequence encoding the oligonucleotide. The oligonucleotide is characterized, in part, in having translational regulatory activity, for example, translational enhancing activity, translational inhibitory activity, internal ribosome entry site (IRES) activity or a combination thereof, and has such translational regulatory activity in a eukaryotic cell.

As disclosed herein, a synthetic translational regulatory element can be identified by screening libraries of randomized oligonucleotides and identifying those having translational enhancing activity, translational inhibitory activity, IRES activity, or a combination thereof in a eukaryotic cell. In addition, a synthetic translational regulatory element can be designed based on the nucleotide sequence of a ribosomal RNA (rRNA; see SEQ ID NOS: 195-197; GenBank Accession Nos. V01335, X00686, X03205, respectively, each of which is incorporated herein by reference). In particular, oligonucleotides to be examined for translational regulatory activity, including IRES activity, can be designed so as to be complementary to an oligonucleotide sequence of rRNA, preferably an un-base paired oligonucleotide sequence of rRNA, which is not generally part of a double stranded region that forms due to hybridization of self-complementary sequence of the rRNA (see FIG. 7B). Furthermore, the a synthetic translational regulatory element can be identified by screening a variegated population of oligonucleotide sequences (see, for example, U.S. Pat. No. 5,837,500), which can be based, for example, on a translational regulatory element of the invention as disclosed herein or on an oligonucleotide sequence complementary to an un-base paired region of a rRNA.

The present invention also provides an isolated translational regulatory element, which includes at least one 5' untranslated region (5' UTR) of a eukaryotic messenger RNA (mRNA) or an oligonucleotide portion thereof, or a deoxyribonucleotide sequence encoding said 5' UTR or oligonucleotide portion thereof. The 5' UTR or oligonucleotide portion thereof is characterized, in part, in having translational enhancing activity, internal ribosome entry site (IRES) activity or a combination thereof, and the translational regulatory activity is effective in a eukaryotic cell.

As used herein, the term "isolated," when used in reference to a translational regulatory element or a nucleotide sequence encoding the element, indicates that the nucleotide sequence is in a form other than the form in which it is found in nature. Thus, a nucleotide sequence encoding an isolated translational regulatory element is separated, for example, from a gene in which it normally can be found in nature, and particularly from a chromosome in a cell, and an isolated translational regulatory element is separated, for example, from an mRNA that normally contains the element. It should be recognized, however, that a translational regulatory element of the invention can be linked to additional nucleotide sequences, yet still be considered "isolated" provided the construct comprising the regulatory element is not in a form that is found in nature. Thus, the translational regulatory element can be contained within a vector, or can be operatively linked to a second nucleotide sequence, for example, another regulatory element or an expressible polynucleotide.

The term "synthetic" also is used herein to refer to a translational regulatory element of the invention. For convenience, the term "synthetic" is used herein to refer to a translational regulatory element that is identified by screening a library of oligonucleotides, which can be randomized oligonucleotides, variegated oligonucleotides, or the like. In comparison, the term "isolated translational regulatory element" is used to refer to an element that is identified by examining a naturally occurring nucleotide sequence, particularly a 5' UTR of an mRNA, which can be a 5' UTR of a known mRNA, or can be identified by screening a cDNA library, particularly those portions of the cDNA encoding mRNA 5' UTRs, or by screening a genomic DNA library. Nevertheless, it should be recognized that the means of producing or identifying a translational regulatory element of the invention is not relevant to the composition, activity or use of the element. As such, an isolated translational regulatory element, having been identified from an mRNA, for example, can be produced using routine chemical or biochemical methods of nucleic acid synthesis and, similarly, a library of oligonucleotides used to identify a synthetic regulatory element can contain oligonucleotides that correspond to translational regulatory elements that also can be found in nature.

As disclosed herein, the translational regulatory elements of the invention can have translational enhancing or translational inhibitory activity, and also can have IRES activity, which provides a means to effect cap-independent translation. In eukaryotes, the initiation of mRNA translation is believed to occur generally by a cap-binding/scanning mechanism, although some mRNAs are translated efficiently despite the lack of a cap structure or a free 5' end (Kozak, *Gene* 234:187-208, 1999; Gingras et al., *Ann. Rev. Biochem.* 68:913-963, 1999). In some of these cases, sequences contained within the mRNA nucleotide sequence directly recruit the translation machinery. These sequences, IRESes, are defined functionally using dicistronic mRNAs, wherein a nucleotide sequence is considered to function as an IRES if, when present in the intercistronic region of a dicistronic mRNA, it directs translation of the second cistron in a manner that is independent of the first cistron.

IRESes have been identified in the 5' UTRs of cellular and viral mNRAs, and have been extensively characterized in picornaviral mRNAs, where they comprise well defined segments of about 450 nucleotides (Nicholson et al., *J. Virol.* 65:5886-5894, 1991). These IRESes have been categorized on the basis of sequence and structural similarities (Jackson and Kaminski, *RNA* 1:985-1000, 1995). In contrast, the IRES elements of cellular mRNAs are not as well characterized, and in many cases distinct boundaries have been difficult to determine by deletion analysis (Stoneley et al., *Oncogene* 16:423-428, 1998; Huez et al., *Mol. Cell. Biol.* 18:6178-6190, 1998; Gan et al., *J. Biol. Chem.* 273:5006-5012, 1998; Bernstein et al., *J. Biol. Chem.* 272:9356-9362, 1997, each of which is incorporated herein by reference). However, a 55 nucleotide sequence of the *Drosophila Antennapedia* 5' UTR has been reported to have IRES activity (Oh et al., *Genes Devel.* 6:1643-1653, 1992, which is incorporated herein by reference).

Cellular IRESes do not contain any obvious sequence similarity to each other or to picornaviral IRES sequences. It has been suggested that IRESes may resemble each other in secondary structure (Le and Maizel, *Nucl. Acids Res.* 25:362-369, 1997). RNA folding analyses have indicated that some cellular IRESes may contain a Y-type system-loop structure, followed by a stem-loop immediately upstream of the initiation codon. This Y-shaped conformation was predicted to occur in IRES sequences of mRNAs encoding the immunoglobulin heavy chain binding protein (BiP), fibroblast growth factor-2, and the *Antennapaedia* gene product, and is reportedly similar to one contained within picornavirus, pestivirus, and hepatitis C virus IRESes (Le et al., *Virus Genes* 12:135-147, 1996). RNA conformations, including Y-shaped secondary structures, also have been predicted to occur within several other cellular IRES sequences (Stoneley et al., supra, 1998; Huez et al., supra, 1998; Sella et al., *Mol. Cell. Biol.* 19:5429-5440, 1999; Nanbru et al., *J. Biol. Chem.* 272: 32061-32066, 1997). In the c-sis mRNA, for example, three independent fragments have IRES activity, and each fragment is proposed to contain a Y-type stem-loop structure (Sella et al., supra, 1999).

No independent physical evidence has demonstrated that the predicted Y-shaped RNA conformations occur in nature, and for many cellular IRESes, the ability to internally initiate translation is not correlated with the presence of the proposed secondary structure. For example, 5' or 3' deletions of the BiP IRES maintain IRES activity even though the deleted fragments do not contain the predicted Y-type stem loop structure (Yan and Sarnow, *Nucl. Acids Res.* 25:2800-2807, 1997).

This lack of correlation between proposed RNA conformations and IRES activity has also been observed in other studies. For example, the vascular endothelial growth factor and c-myc IRESes each contain two non-overlapping fragments with IRES activity (Stoneley et al., supra, 1998; Huez et al., supra, 1998), and the BiP IRES has three non-overlapping fragments with IRES activity, none of which contain the proposed Y-type stem-loop structure, or, at best, contain only part of it (Yang and Sarnow, supra, 1997). Such observations suggest that cellular IRESes may be composed of numerous, short segments that have independent IRES activity or that act together to affect overall IRES activity.

As disclosed herein, analysis of the Gtx 5' UTR (SEQ ID NO: 1) revealed numerous oligonucleotide portions of the 5' UTR having translational regulatory activity (see Example 1). Thus, the present invention provides, for example, an isolated translational regulatory element encoded by any of nucleotides 1 to 40, 1 to 81, 1 to 120, 41 to 81, 14 to 196, 80 to 120, 80 to 196, 120, to 166, and 120 to 196 of the Gtx homeodomain 5' UTR (SEQ ID NO: 1). Even more remarkably, a 9 nucleotide sequence the Gtx homeodomain mRNA 5' UTR (SEQ ID NO: 2; nucleotides 141 of the 196 nucleotide Gtx 5' UTR; SEQ ID NO: 1) was demonstrated to have the characteristics of an IRES element (see Example 1; Komuro et al., *EMBO J.* 12:1387-1401, 1993, which is incorporated herein by reference). This GtX IRES module (SEQ ID NO: 2) functions independently to enhance translational activity, and multiple copies of the IRES module synergistically enhance translational activity (see Example 1). Accordingly, the present invention also provides an isolated translational regulatory element encoded by SEQ ID NO: 2.

As disclosed herein, the Gtx 5' IRES module (SEQ ID NO: 2) can be linked at its upstream (5) end or downstream (3) end or both ends to a spacer nucleotide sequence, which can be about 1 to 100 ribonucleotides in length such that the activity of the IRES module can be varied. Thus, the invention provides, for example, a translational regulatory element encoded by any of SEQ ID NOS: 4, 5, 12, and 20 to 22, which includes a Gtx IRES module (SEQ ID NO: 2) and confers variable levels of IRES activity on an operatively linked expressible polynucleotide.

An isolated translational regulatory element also can contain two or more of the oligonucleotide portions encoded by SEQ ID NO: 2, which are operatively linked to each other, for example, five or ten of the oligonucleotides in operative linkage, and each of the oligonucleotides (SEQ ID NO: 2) can, but need not, be separated from each other by a spacer nucleotide sequence. As disclosed herein, multiple copies of a Gtx IRES module exhibit a greater than additive amount of IRES activity (see Example 1). Thus, the present invention provides, for example, an isolated translational regulatory elements encoded by any of SEQ ID NOS: 6 to 11 and 13 to 15.

The cooperative increase in IRES activity exhibited by multiple copies of the Gtx IRES module indicates that cellular IRES activity can depend on the strength, number and spacing of various individual IRES modules. Photochemical crosslinking studies previously demonstrated that this region of the Gtx mRNA sequence binds to 40S ribosomal subunits by crosslinking to its complement within the 18S rRNA (Hu et al., *Proc. Natl. Acad. Sci., USA* 96:1339-1344, 1999, which is incorporated herein by reference). As disclosed herein, the 9 nucleotide IRES module is 100% complementary to the 18S rRNA at nucleotides 1132 to 1124.

A further examination of 5' UTRs of eukaryotic mRNAs revealed that translational regulatory activity, including IRES activity, was effected by the 5' UTRs of five dendritically localized mRNAs, including the rat activity related cytoskeletal protein (ARC; see SEQ ID NO: 25), rat dendrin (see SEQ ID NO: 24), rat microtubule associated protein-2 (MAP2; see SEQ ID NO: 26), the rat α-Cam Kinase II subunit (CamK IIa; SEQ ID NO: 23), and the rat RC3 neurogranin gene (see SEQ ID NO: 27), by two yeast 5' UTRs, yeast YAP1 (see SEQ ID NO: 28) and yeast p150 (see SEQ ID NO: 29), by the 5' UTRs of mRNAs encoding the rat amyloid precursor protein (APP; see SEQ ID NO: 161), the rat beta-site APP cleaving enzyme (Bace; SEQ ID NO: 162), the human FMR protein (see SEQ ID NO: 164), and the mouse Rbm3 protein (see SEQ ID NO: 164), each of which internally initiated translation when placed in the intercistronic region of a dicistronic RNA (see Examples 2 and 3). Accordingly, in one embodiment, the present invention provides an isolated translational regulatory element encoded by a nucleotide sequence selected from any of SEQ ID NOS: 1, 23 to 29, 161 to 164

Detailed analysis of two of the 5' UTRs, yeast p150 and mouse Rbm3, confirmed the results obtained for the Gtx 5' UTR. Thus, oligonucleotide portions of the yeast p150 5' UTR, including, for example, those encoded by any of nucleotides 1 to 250, 100 to 508, 160 to 508, 250 to 508, 375 to 508, 429 to 508, 481 to 508, and 250 to 390 of SEQ ID NO: 29 (see Example 3); and oligonucleotide portions of the mouse Rbm3 5' UTR, including, for example, those encoded by any of SEQ ID NOS: 165 to 169, 171 to 176, and 182 to 192 (see Example 6 and FIG. 6), and, therefore, are examples of isolated translational regulatory elements of the invention that have translational enhancing activity or IRES activity or both. In addition, examples of oligonucleotide portions of a eukaryotic mRNA 5' UTR having translational inhibitory activity include those encoded by nucleotides 120 to 196 and 167 to 196 of the Gtx homeodomain protein mRNA (SEQ ID NO: 1), and by nucleotides 1 to 100 and 100 to 160 of the yeast p150 mRNA (SEQ ID NO: 29).

Analysis of the mouse Rbm3 5' UTR further revealed modular elements consisting of about 9 to 22 nucleotides, which exhibited IRES activity (see SEQ ID NO: 191), translational enhancing activity (see SEQ ID NO: 192), and translational inhibitory activity (see SEQ ID NOS: 193 and 194). These results indicate that the 5' UTRs of eukaryotic mRNAs consist of a modular structure containing one or more elements that variously effect translational regulatory activity. Accordingly, the present invention also provide oligonucleotide portions of a 5' UTR of a eukaryotic mRNA that have translational enhancing activity, translational inhibitory activity, IRES activity, or a combination thereof, including, for example, SEQ ID NOS: 192 to 194.

As further disclosed, screening of libraries of random oligonucleotides containing 9 or 18 nucleotides identified numerous novel oligonucleotides having IRES activity, including combinations of such oligonucleotides. Accordingly, the present invention provides relates to a synthetic translational regulatory element, which includes at least one oligonucleotide consisting of about 6 to 125 ribonucleotides, or a deoxyribonucleotide sequence encoding the oligonucleotide. For example, the invention provide a synthetic translational regulatory element encoded by any of SEQ ID NOS: 42 to 46, 49, 50, 52, and 89 to 160, which were identified by screening libraries of randomized oligonucleotides (Example 4D). Furthermore, as disclosed herein, such oligonucleotides having translational regulatory activity can be operatively linked to each other, and can be the same or different Examples of synthetic translational regulatory elements containing operatively linked oligonucleotides that have translational regulatory activity and are different from each other are exemplified by those encoded by any of SEQ ID NOS: 53 to 88 (see Example 4D), and examples of synthetic translational regulatory elements containing operatively linked oligonucleotides that have translational regulatory activity and are the same are exemplified by those encoded by elements containing 3 or 5 copies of SEQ ID NO: 51 or 5 copies of SEQ ID NO: 52, each copy separated by a 9 nucleotide spacer sequence (see Example 4C).

The identification of these modular IRES elements such as the 9 nucleotide Gtx IRES module, which functions independently as an IRES, is inconsistent with the hypothesis that Y-shaped RNA conformations are required for IRES activity in cellular mRNA (see, for example, Le and Maizel, supra, 1997). While RNA conformation may be critical for the activity of some cellular IRESes, as it is for picornavirus IRES element, the present results suggest that RNA secondary structures may simply alter the accessibility or presentation of individual IRES modules to the translation machinery.

A nucleotide sequence including the Gtx IRES module (SEQ ID NO: 2) directly bound to 40S ribosomal subunits by base pairing to the 18S rRNA (Hu et al., supra, 1999). When tested in the 5' UTR of a monocistronic reporter construct, this nucleotide sequence inhibited translation, and mutations that increased the degree of complementarily to the rRNA decreased the translation of a monocistronic mRNA, whereas mutations that decreased complementarity increased translation (Tranque et al., *Proc. Natl. Acad. Sci., USA* 95:12238-12243, 1998, which is incorporated herein by reference). Nucleotide sequences of the yeast YAP1 and yeast p150 5' UTRs also share complementarity with 18S rRNA sequences (see FIG. 5). As disclosed herein, the Gtx IRES module (SEQ ID NO: 2) also functions as an IRES element when positioned in the intercistronic region of a dicistronic mRNA. As such, this element has opposite effects on translation, depending on whether it is present in a monocistronic mRNA or in a dicistronic mRNA. Very active IRES modules likely recruit the 40S subunit efficiently, but allow it to detach for protein synthesis to occur, whereas less active IRES modules either may recruit poorly because of weak initial interactions with the 40S subunit or may form very stable interactions that effectively sequester the mRNA.

The results disclosed herein indicate that base pairing between segments of mRNA and 18S rRNA can lead to ribosome recruitment and translation initiation, thus explaining an earlier observation that large numbers of eukaryotic mRNAs contain segments complementary to 18S rRNA (Mauro and Edelman, *Proc. Natl. Acad. Sci., USA* 94:422-427, 1997, which is incorporated herein by reference). If particular subsets of these mRNA sequences function as IRES modules, then large numbers of different mRNAs may use these sequences to recruit ribosomes. Sequences complementary to 18S rRNA also are present in other cellular IRESes (Gan et al., supra, 1998; Bernstein et al., supra, 1997). Similarly, the picornaviral IRES elements contains an oligopyrimidine stretch that is complementary to the 3' end of the 18S rRNA (Scheper et al., *FEBS Lett.* 352:271-273, 1994). While this oligopyrimidine sequence is important for IRES activity (Meerovitch et al., *J. Virol.* 65:5895-5901, 1991; Pestova et al., *J. Virol.* 65:6194-6204, 1991), it has not been shown to base pair to the 18S rRNA. Such sequences are not found in the hepatitis C, classic swine fever, and bovine diarrhea pestivirus IRESes, although reconstitution studies provide indirect evidence for base pairing interactions between these IRESes and 18S rRNA (Pestova et al., *Genes Devel.* 12:67-83, 1998; Pestova and Hellen, *Virology* 258:249-256, 1999).

In addition to complementarity to 18S rRNA, IRES modules also may recruit ribosomes through interactions with ribosomal proteins or with components of the translation machinery such as initiation factors, or through other intermediary proteins. For example, the iron regulatory element (IRE), which is an RNA translational control sequence, functioned as an IRES module in the presence of an engineered intermediary protein (De Gregorio et al., *EMBO J.* 18:4865-4874, 1999). In this system, the IRE binding protein (IRP-1), which binds the IRE, was fused to the C-terminal region of initiation factor eIF4G to produce a fusion protein that acts as an intermediary protein that can recruit the preinitiation complex, presumably though an interaction with initiation factor eIF3. This artificial recruitment of the translation machinery was sufficient to obtain weak but detectable IRES activity when the IRE was inserted in the intercistronic region of a dicistronic mRNA (De Gregorio et al., supra, 1999).

The ability to internally initiate translation may be used by some mRNAs under conditions that are not favorable for cap-dependent translation, for example, during mitosis or poliovirus infection (Johannes et al., *Proc. Natl. Acad. Sci., USA* 96:13118-13123, 1999). However, in contrast to many viral mRNAs, virtually all eukaryotic mRNAs are monocistronic and contain a cap structure (Kozak, supra, 1999; Shatkin, *Cell* 9:645-653, 1976). Thus, the ability to internally initiate translation may be a reflection of the ability of a sequence to recruit ribosomes, and if the recruitment is sufficient to enhance translation, these sequences can confer a selective advantage to some mRNAs over others under competitive situations within the cell. IRES modules in eukaryotic mRNAs also can be mechanistically analogous to the prokaryotic Shine and Dalgarno sequence, albeit more complex because they are combined as multiple elements and the complementary sequences are not fixed in location either within the mRNA or rRNA.

As disclosed herein, two, five or ten copies of the 9 nucleotide Gtx IRES module (SEQ ID NO: 2) and of two synthetic oligonucleotides (SEQ ID NOS: 51 and 52) have a synergistic effect on IRES activity (Examples 1 and 4). This effect is similar to that observed with cis-acting transcriptional enhancers (Busby et al., *J. Mol. Biol.* 241:341-352, 1994), suggesting that the evolution of translational enhancers and regulators and may parallel that of cis-acting transcriptional enhancers. It has been suggested that the synergistic effect of transcriptional enhancers may be due to cooperative interactions between weak transcription factors, thus increasing the local concentration of these factors (Ptashne and Gann, *Curr. Biol.* 8:R812-R822, 1998; Ptashne and Gann, *Nature* 386:569-577, 1997). Although the mechanism for the observed synergistic effect of translational enhancement is not relevant to the present invention, it is noted that, similar to synergistic transcriptional enhancement, weak interactions between components of the translational machinery may explain the synergistic effects disclosed herein. Alternatively, or in addition, increased recruitment may lead to higher local concentrations of some of the initiation factors that otherwise are limiting for translation. For example, high levels of eIF4A, which is an RNA helicase, may maintain a more open mRNA secondary structure and allow more efficient translation.

As disclosed herein, a translational regulatory element of the invention is useful for modulating the expression of a polypeptide. Synthetic IRESes of the invention were up to 63-fold more active than the EMCV IRES and appear to be much stronger than most or all of the naturally occurring IRESes that have been characterized (Borman et al., *Nucl. Acids Res.* 25:925-932, 1997; Martinez-Salas, *Curr. Opin. Biotech.* 10:458-465, 1999). In particular, methods of finely tuning the level of IRES activity by varying the number of operatively linked IRES modules are provided. Thus, the compositions and methods of the invention are useful, for example, for gene therapy, protein manufacturing, and the like.

The 5' UTR from five dendritically localized mRNAs, ARC, dendrin, MAP2, CamK IIa, and RC3, internally initiated translation when placed in the intercistronic region of a dicistronic RNA (Example 2). Furthermore, these 5' UTRs utilize both cap-independent and cap-dependent mechanisms simultaneously, resulting in the increased translation of monocistronic reporter mRNAs. Such IRES elements provide a means to ensure efficient translation of the dendritically localized transcripts.

A small number of mRNAs are localized to dendrites and the translation of some or all of these mRNAs is likely required to affect synaptic efficacy. Inasmuch as many of the components of the translational machinery can be limiting at these cellular sites, dendritically localized mRNAs were examined for internal ribosomal entry sites (IRES elements), which can increase translation efficiency. The 5' UTRs of the dendritically localized mRNAs were tested for IRES activity in the intercistronic region of dual luciferase dicistronic mRNAs. Transfection of neural and non-neural cell lines with constructs containing the 5' UTRs from the dendritically localized mRNAs and the encephalomyocarditis virus (EMCV) IRES resulted in translation of the second cistron that was significantly higher than that observed for a control construct containing the β-globin 5' UTR. Translation facilitated by these IRES elements was independent of the first cistron; translation of the second cistron occurred even when translation of the first cistron was blocked. Each of the ARC, MAP2 and CamK IIa 5' UTRs functioned as a translational enhancer in a monocistronic reporter mRNA, whereas the dendrin 5' UTR slightly inhibited translation compared to a control construct Blocking of cap-dependent translation in these monocistronic constructs showed that internal initiation accounted for about 60% to 90% of the translation initiation of these mRNAs.

The ability of the dendritically localized 5' UTRs to direct internal initiation of translation was demonstrated using a dicistronic RNA containing two separately assayable luciferase reporter genes in three neural cell lines and three non-neural cell lines (Example 2). When introduced into the intercistronic region of the dual luciferase dicistronic message, each of the 5' UTRs significantly induced translation of the second cistron. Furthermore, this activity was not inhibited by the presence of a hairpin structure at the 5' end of the dicistronic message, which effectively reduces the possibility of read-through translation from one cistron to the next, thus demonstrating that the 5' UTRs direct internal initiation of translation in a manner characteristic of an IRES. The ARC, dendrin, MAP2 and CamK IIa 5' UTRs generated significant levels of IRES activity and internally initiated translation in neural and non-neuronal cells and, therefore, can be used to modulate translation in a variety of different cell types. In addition, while the relative IRES activity generated by the 5' UTRs in non-neural cells was similar to that observed for the neural cell lines, the overall levels of IRES activity differed across cell types, and was consistently higher in non-neural cell lines.

The translation efficiency of monocistronic mRNAs is believed to be a function of the length of the 5' UTR, combined with other factors such as structure and upstream initiation codons. The β-globin 5' UTR is considered to be the standard of cap-dependent translation, being an optimal length, having very little secondary structure, and having no upstream AUG codons. In comparison, the lengths of the 5' UTRs for MAP2, CamK IIa and ARC average about 3 times the length of the β-globin 5' UTR, yet monocistronic mRNAs containing these 5' UTRs all were translated significantly better than that containing β-globin. However, the dendrin 5' UTR inhibited translation of monocistronic RNAS. Inhibition of translation has been observed for some viral IRES elements positioned 5' to monocistronic reporter mRNAs, and can be due to the secondary structure associated with the viral IRES inhibiting ribosomal scanning from the cap. As there is no evidence of a change in mRNA stability, the dendrin 5' UTR may have more secondary structure than the other 5' UTRs examined here. Several 5' UTRs also have been shown to be important in the developmental regulation of translation, and many of these function through IRES elements.

Since all monocistronic mRNAs should be equally capable of utilizing cap-dependent translation, the differences in translation of the monocistronic mRNAs observed herein likely is intrinsic to each 5' UTR. Since mRNA stability was not affected by the 5' UTRs (Example 2), the IRES elements contained in these 5' UTRs likely modulate translation of the monocistronic mRNAs. For the MAP2, ARC, and CamK IIa 5' UTRs, IRES activity can supplement cap-dependent translation to provide higher levels of translation. Monocistronic reporter gene mRNAs, although more physiologically relevant than dicistronic mRNAs, cannot discriminate as to whether the 5' UTRs from the dendritically localized mRNAs can employ cap-independent translational mechanisms.

The incorporation of a stable hairpin structure to prevent cap-dependent translation via ribosomal scanning of the mRNAs confirmed that all four of the 5' UTRs utilize internal initiation in monocistronic mRNAs (Example 2). In addition, the differential effects of the hairpin on the monocistronic mRNAs demonstrated that varying degrees of cap-dependent and independent mechanisms occur for each 5' UTR. For example, the dendrin 5' UTR which, unlike the other three 5' UTRs, did not increase the translation of non-hairpin monocistronic mRNA, exhibited one of the strongest effects when cap-dependent translation was inhibited. These results indicate that the dendrin 5' UTR directs translation primarily through cap-independent mechanisms; the absence of cap-dependent translation explains the observation that the dendrin 5' UTR was below control values in the monocistronic construct. The ability of a 5' UTR to effect both cap-dependent and cap-independent translation indicates that an mRNA containing such a 5' UTR is more likely to be translated than a cap-dependent mRNA such as β-globin, particularly under conditions where cap-dependent translation is compromised. As such, these 5' UTRs can provide a means to ensure translation of these dendritically localized mRNAs.

In viral RNAs, which lack a cap, IRES elements likely serve to circumvent cap-dependent recruitment of the translational machinery to the 5' UTR. However, since most eukaryotic mRNAs contain a cap structure, IRES elements can serve other functions in eukaryotes. In particular, a eukaryotic IRES can ensure the translation of a particular message under conditions where cap-dependent translation is inefficient or inhibited. For several eukaryotic IRES elements that have been described, stress and other cellular states that generally hinder cap-dependent protein synthesis have little or no effect on IRES mediated translation. A similar case may occur for the dendritically localized mRNAs, which, as disclosed herein, contain 5' UTRs direct cap-dependent and cap-independent translation (Example 2). Furthermore, cap-dependent translation is tightly regulated by cellular events and often involves modulation of cap-binding activity. As such, an mRNA containing an IRES can be translated efficiently during a cellular stress condition such as ischemia or apoptosis, which otherwise affects overall levels of translation.

Experiments using a dominant negative form of the eukaryotic initiation factor-4 (eIF4) binding protein, eIF4-bp1, demonstrated that the 5' UTRs from the dendritically localized mRNAs initiated translation under conditions where cap binding is inhibited. Endogenous 4E-BP1 binds to and sequesters eIF4E, disabling cap-dependent translation until 4E-BP1 is phosphorylated. The 4E-BP1 mutant, which lacks the critical phosphorylation sites necessary for disengagement with eIF4E, irreversibly binds eIF4E and prevents cap-dependent translation. Transfection of this mutant 4E-BP1 with monocistronic 5' UTR constructs reduced the cap-dependent translation from the 5' UTR of β-globin by greater than 55% (lack of further reduction of β-globin can be related to plasmid titer, lack of co-transfection in some cells, or feedback on the 4E-BP1 mutant's own capped message), whereas constructs containing the 5' UTRs initiated translation of monocistronic mRNAs to various degrees in the absence of cap-binding. The lack of dependence of dendrin 5' UTR on cap-binding for translation supports the previous observation that this 5' UTR is primarily translated through cap-independent mechanisms. These results indicate that IRES mediated translation can yield constitutive expression of certain proteins, regardless of cap-dependent translational control. Furthermore, the degree to which the IRES can internally initiate translation in the absence of cap-binding provides an additional level of translational regulation, including providing a means for maintaining translation of cellular messages critical for important cellular events.

Although it is not clear whether cap-independent mechanisms are utilized within the dendritic compartment, each of the five 5' UTRs, which were selected based on their mRNA subcellular distribution, demonstrated IRES activity to some degree. Remarkably, these 5' UTRs do not share characteristics of other IRES elements, were not selected, for example, based on length, exceptional GC content, or excess of upstream AUG start codons, and have no overall sequence similarity. The 5' UTR from the neural cell adhesion molecule (NCAM) mRNA, a neuronal message that is not dendritically localized, did not demonstrate any significant IRES activity. It has been reported that cap-analogs, which prevent cap-dependent protein synthesis, can perturb lasting changes in long-term depression Those observation together with the results disclosed herein suggest that dendrites may utilize internal initiation as a mechanism for translation of dendritically localized messages, and may do so in response to synaptic stimuli or other perturbations in cellular homeostasis.

As disclosed herein, a translational regulatory element of the invention can be contained in a vector. The vector can be any vector, but preferably is an expression vector, which can contain a translation initiation site in addition to the translational regulatory element Generally, the translational regulatory element will have translational enhancing activity or IRES activity, particularly where the vector is to further contain an expressible polynucleotide. However, the vector also can contain a translational regulatory element of the invention having translational inhibitory activity, for example, where it is desired to introduce the element into a cell to inhibit translation of a polypeptide to which it is operatively linked, or where it is desired to use the element to bind translational regulatory factors that would otherwise bind an endogenous form of such an element and inhibit translation.

Where the vector is an expression vector, it can further contain a translation start codon, which can be operatively linked to a translation initiation site and to the translational regulatory element. However, such elements also can be part of an expressible polynucleotide that is to be inserted into the vector. Accordingly, a vector of the invention can contain an expressible polynucleotide, wherein the translational regulatory element is operatively linked to the expressible polynucleotide. As used herein, the term "expressible polynucleotide" refers to any polynucleotide that can be transcribed into an RNA molecule and, particularly, can be translated into a polypeptide. The expressible polynucleotide can simply be a coding sequence of a polypeptide, or can contain one or more regulatory elements generally associated with a polynucleotide to be transcribed or translated, for example, a transcriptional promoter, transcription start site, polyadenylation signal sequence, Kozak sequence, initiator methionine codon, stop codon and the like. Where the expressible polynucleotide contains all or substantially all of the elements required for expression of a polypeptide, it also is referred to herein as a "cistron". In referring to "substantially" all of the element required for expression, it will be recognized that a cistron may or may not contain a translational regulatory element, since such an element is provided according to the present invention.

It should further be recognized that an expressible polynucleotide can contain more than one cistron, for example, can be dicistronic such as the numerous dicistronic expressible polynucleotide described in the Examples. In general, where an expressible polynucleotide contains more than one cistron, the cistrons are operatively linked such that they are transcribed as a single RNA molecule. In addition, a spacer nucleotide sequence generally will be present between the cistrons, and, if desired, a translational regulatory element of the invention having IRES activity or translational enhancing activity or both can be inserted into the spacer nucleotide sequence. As disclosed herein, an expressible polynucleotide can be contained in a vector of the invention.

A vector of the invention also can contain additional elements generally found in a vector, including, for example, a nucleotide sequence encoding a polypeptide that confers antibiotic resistance upon a cell containing the vector, including a bacterial cell, an insect cell, or a mammalian cell, as desired, and can contain an origin of replication, for example, a bacterial origin of replication such that the vector can be amplified in a bacterial host cell. Accordingly, the invention also provides a host cell containing a vector of the invention. Vectors, which include plasmid vectors and viral vectors such as bacteriophage, baculovirus, retrovirus, lentivirus, adenovirus, vaccinia virus, semliki forest virus and adeno-associated virus vectors, and host cells for containing a particular vector, are well known and can be purchased from a commercial source (Promega, Madison Wis.; Stratagene, La Jolla Calif.; Invitrogen, La Jolla Calif.) or can be constructed by one skilled in the art (see, for example, *Meth. Enzymol., Vol.* 185, Goeddel, ed. (Academic Press, Inc., 1990); Jolly, *Canc. Gene Ther.* 1:51-64, 1994; Flotte, *J. Bioenerg. Biomemb.* 25:37-42, 1993; Kirshenbaum et al., *J. Clin. Invest.* 92:381-387, 1993; each of which is incorporated herein by reference).

Where a translational regulatory element of the invention is to be introduced into a cell in culture or in an organism, a viral vector can be particularly useful. Viral vectors provide the advantage that they can infect host cells with relatively high efficiency and can infect specific cell types. For example, a translational regulatory element of the invention operatively linked to an expressible polynucleotide that is to be expressed in lung cells can be cloned into an adenovirus vector, which effectively infects lung epithelial cells. Similarly, a translational regulatory element of the invention operatively linked to an expressible polynucleotide that is to be expressed in neuronal cells can be cloned into a herpesvirus vector, which effectively infects neuronal cells. Viral vectors have been developed for use in particular host systems, particularly mammalian systems and include, for example, retroviral vectors, other lentivirus vectors such as those based on the human immunodeficiency virus (HIV), adeno-associated virus vectors, herpesvirus vectors, vaccinia virus vectors, and the like (see Miller and Rosman, *BioTechniques* 7:980-990, 1992;

Anderson et al., *Nature* 392:25-30 Suppl., 1998; Verma and Somia, *Nature* 389:239-242, 1997; Wilson, *New Engl. J. Med.* 334:1185-1187 (1996), each of which is incorporated herein by reference).

A translational regulatory element of the invention, which can be contained in a vector, can be introduced into a cell by any of a variety of methods known in the art (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the translational regulatory element is to be introduced, as well as whether the cell is isolated in culture, or is in a tissue or organ in culture or in situ, and, as disclosed herein, the selection system can be based on a reporter polypeptide that is expressed, at least in part, due to the translational regulatory element of the invention. Introduction of a translational regulatory element of the invention into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference).

The present invention further relates to a recombinant nucleic acid molecule, which contains a translational regulatory element of the invention operatively linked to an expressible polynucleotide. The expressible polynucleotide can comprise a cistron, and the translational regulatory element have translational enhancing activity or IRES activity or both. The expressible polynucleotide also can comprises, in operative linkage in a 5' (upstream) to 3' (downstream) orientation, a fist cistron, a spacer nucleotide sequence, and a second cistron, and the translational regulatory element can have IRES activity, and be operatively linked to the second cistron. The synthetic translational regulatory element in a recombinant nucleic acid molecule of the invention can include two or more operatively linked oligonucleotides having translational regulatory activity, for example, ten copies of SEQ ID NO: 2, each of which can be separated by a spacer nucleotide sequence.

The polypeptide encoded by a recombinant nucleic acid molecule of the invention can be any polypeptide, including, for example, an enzyme such as β-galactosidase, β-glucuronidase, luciferase, alkaline phosphatase, glutathione S-transferase, chloramphenicol acetyltransferase, guanine xanthine phosphoribosyltransferase, and neomycin phosphotransferase; a viral or bacterial polypeptide or an epitope expressed by a virus, bacterium or other pathogenic organism; or a growth factor, a hormone and a receptor for a growth factor or a hormone. The recombinant nucleic acid molecule also can encodes two or more polypeptides, for example, a first polypeptide that encodes a reporter polypeptide, which can be a selectable marker, and a second polypeptide encoding a polypeptide of interest, for example a therapeutic polypeptide.

The term "oligonucleotide", "polynucleotide" or "nucleotide sequence" is used broadly herein to mean a sequence of two or more deoxyribonucleotides or ribonucleotides that are linked together by a phosphodiester bond. As such, the terms include RNA and DNA, which can be a gene or a portion thereof, a cDNA, a synthetic polydeoxyribonucleic acid sequence or polyribonucleic acid sequence, or the like, and can be single stranded or double stranded, as well as a DNA/RNA hybrid. Furthermore, the terms "oligonucleotide", "polynucleotide" and "nucleotide sequence" include naturally occurring nucleic acid molecules, which can be isolated from a cell, as well as synthetic molecules, which can be prepared, for example, by methods of chemical synthesis or by enzymatic methods such as by the polymerase chain reaction (PCR).

For convenience of discussion, the term "oligonucleotide" generally is used to refer to a nucleotide sequence that is has translational regulatory activity, particularly a nucleotide sequence of a translational regulatory element of the invention. In comparison, the term "polynucleotide" or "nucleotide sequence" generally refers to a sequence that encodes a peptide or polypeptide, acts as or encodes a desired regulatory element, provides a spacer sequence or cloning site, or the like. It should be recognized, however, that such a use only is for convenience and is not intended to suggest any particular length or other physical, chemical, or biological characteristic of the nucleic acid molecule.

Synthetic methods for preparing a nucleotide sequence include, for example, the phosphotriester and phosphodiester methods (see Narang et al., *Meth. Enzymol.* 68:90, (1979); U.S. Pat. Nos. 4,356,270, 4,458,066, 4,416,988, 4,293,652; and Brown et al, *Meth. Enzymol.* 68:109, (1979), each of which is incorporated herein by reference). In various embodiments, an oligonucleotide of the invention or a polynucleotide useful in a method of the invention can contain nucleoside or nucleotide analogs, or a backbone bond other than a phosphodiester bond. The nucleotides comprising an oligonucleotide (polynucleotide) generally are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234 (1994); Jellinek et al., *Biochemistry* 34:11363-11372 (1995); Pagratis et al., *Nature Biotechnol.* 15:68-73 (1997), each of which is incorporated herein by reference).

The covalent bond linking the nucleotides of an oligonucleotide or polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986 (1994); Ecker and Crooke, *BioTechnology* 13:351360 (1995), each of which is incorporated herein by reference). The incorporation of non-naturally occurring nucleotide analogs or bonds linking the nucleotides or analogs can be particularly useful where the nucleotide sequence is to be exposed to an environment that can contain a nucleolytic activity, including, for example, a tissue culture medium or upon administration to a living subject, since the modified nucleotide sequences can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally are chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

A recombinant nucleic acid molecule, or a vector, of the invention can contain additional sequences that confer a desired characteristic on the polynucleotide. In particular, the recombinant nucleic acid molecule or vector can contain an operatively linked transcriptional regulatory element, including a transcriptional promoter or enhancer, which can be a constitutively expressed regulatory element, which maintains expression of a polynucleotide at a relatively constant level of activity (basal level), or can be an inducible regulatory elements. Constitutively expressed regulatory elements can be expressed in any cell type, or can be tissue specific, which are expressed only in particular cell types, phase specific, which are expressed only during particular developmental or growth stages of a plant cell, or the like. A regulatory element such as a tissue specific or phase specific regulatory element or an inducible regulatory element useful in constructing a recombinant polynucleotide or in a practicing a method of the invention can be a regulatory element that generally, in nature, is found in a plant genome. However, the regulatory element also can be from an organism other than a plant, including, for example, from a plant virus, an animal virus, or a cell from an animal or other multicellular organism.

As disclosed herein, translational regulatory elements can be selected based on their ability to confer tissue specific translation, or translation in response to an inducing agent. As used herein, the term "tissue specific," when used in reference to a translational regulatory element, means a nucleotide sequence that effects translation of an operatively linked expressible polynucleotide in only one or a few cell types. As used herein, the term "inducible," when used in response to a translational regulatory element, means a nucleotide sequence that, when present in a cell exposed to an inducing agent, effects an increased level of translation of an operatively linked expressible polynucleotide as compared to the level of translation, if any, in the absence of an inducing agent.

The term "inducing agent" is used to refer to a chemical, biological or physical agent that effects translation from an inducible translational regulatory element. In response to exposure to an inducing agent, translation from the element generally is initiated de novo or is increased above a basal or constitutive level of expression. Such induction can be identified using the methods disclosed herein, including detecting an increased level of a reporter polypeptide encoded by the expressible polynucleotide that is operatively linked to the translational regulatory element. An inducing agent can be, for example, a stress condition to which a cell is exposed, for example, a heat or cold shock, a toxic agent such as a heavy metal ion, or a lack of a nutrient, hormone, growth factor, or the like; or can be exposure to a molecule that affects the growth or differentiation state of a cell such as a hormone or a growth factor. By examining the translational regulatory activity of a translational regulatory element of the invention or a combination of such elements in cells exposed to such conditions, or cells of a particular cell type, translational regulatory elements that are inducible or tissue specific can be identified. As such, a recombinant nucleic acid molecule of the invention can contain a tissue specific or inducible translational regulatory element.

An expressible polynucleotide can be any polynucleotide that is operatively linked to a translational regulatory element of the invention and encodes a polypeptide. As used herein, the term "operatively linked" means that a regulatory element, which can be a transcriptional or translational regulatory element, including a translational regulatory element of the invention, is positioned with respect to a transcribable or translatable nucleotide sequence such that the regulatory element can effect its regulatory activity. A transcriptional enhancer, for example, can be located at any distance, including adjacent to or up to thousands of nucleotides away from, and upstream or downstream from the promoter and nucleotide sequence to be transcribed, and still exert a detectable effect on the level of expression of an encoded reporter molecule. In comparison, a translational regulatory element generally is contained within about 1 to 500 nucleotides, particularly within about 1 to 100 nucleotides of a translation start site. In addition, the term "operatively linked" is used with respect to a first and second polypeptide (or peptide) to refer to encoding sequences that are linked in frame such that a fusion polypeptide can be produced. Similarly, the term is used to refer to two or more cistrons of an expressible polynucleotide that are transcribed as a single RNA molecule, which can contain, for example, an IRES element of the invention in an intercistronic position.

As used herein, the term "heterologous" is used in a comparative sense with respect to a nucleotide sequence to indicate either that the nucleotide sequence is not an endogenous nucleotide sequence in a cell into which it is to be introduced, or that the nucleotide sequence is part of a construct such that it is in a form other than it normally would be found in a cell. For example, a heterologous nucleotide sequence can be a polynucleotide that encodes a mammalian viral polypeptide, where the heterologous nucleotide sequence is to be introduced into a plant cell; i.e., the nucleotide sequence is heterologous with respect to the plant cell. A heterologous nucleotide sequence also can be, for example, a portion of a plant gene sequence that is operably linked to a plant CRRE, provided that the construct is not normally found in a plant cell, for example, a plant CRRE operably linked to a heterologous nucleotide sequence consisting of a hypothetical plant gene exon 3, wherein the plant gene can be a circadian-regulated gene comprising the plant CRRE to which the exon is operably linked. Thus, a heterologous nucleotide sequence in a recombinant polynucleotide of the invention can be any nucleotide sequence that is not normally part of the plant circadian-regulated gene from which the oligonucleotide comprising the CRRE-component of the recombinant polynucleotide is obtained; or, if it is a part of the plant circadian-regulated gene from which the CRRE is obtained, it is an orientation other than it would normally be in the gene, for example, is an antisense sequence, or comprises at least a partially discontinuous sequence as compared to the genomic structure.

The present invention also relates to a kit, which contains a translational regulatory element of the invention. In particular, a kit of the invention can contain a plurality of synthetic transcriptional regulatory elements, particularly a plurality of different translational regulatory element The translational regulatory elements of the plurality can be used individually for a specific purpose depending on the characteristics of the element, for example, translational enhancing activity, IRES activity, or translational inhibitory activity, or tissue specific expression, inducible expression, or other characteristic. In addition, the translational regulatory elements of the plurality can be used in combination to provide, for example, a high level of translational enhancing or IRES activity.

The translational regulatory elements in a kit of the invention can contain one or more flanking sequence, which, independently, can be at a 5' end or a 3' end or both 5' and 3' ends.

Such flanking sequences can be, for example, restriction endonuclease recognition sites or recombinase recognition sites such as a lox or att sequence, and can be single stranded overhangs. As such, the flanking sequence can be used to facilitate operatively linking two or more translational regulatory elements in the plurality to each other or for linking the element to any other polynucleotide.

The present invention also relates to a method of producing a genetically modified cell that exhibits altered expression of a polypeptide. The method can be performed, for example, by introducing a translational regulatory element of the invention into a cell, whereby the synthetic translational regulatory element operatively linked to a nucleotide sequence encoding a polypeptide. As disclosed herein, the translational regulatory element can be operatively linked to the nucleotide sequence, which can be an expressible polynucleotide, prior to introducing the translational regulatory element into the cell. For example, the translational regulatory element can have translational enhancing activity or IRES activity such that the encoded polypeptide is expressed in the cell, preferably in a desired level. The polypeptide can be any polypeptide, including, for example, a reporter polypeptide, a toxin, or a therapeutic agent.

As disclosed herein, the nucleotide sequence to which the translational regulatory element is operatively linked also can be a sequence of an endogenous gene in the cell genome. Where it is desired, for example, to decrease the expression of an endogenous polypeptide in a cell, for example, expression of an activated Ras protein, the translational regulatory element is selected based on its having translational inhibitory activity. The translational regulatory element can be targeted to a particular locus, for example, upstream of the start codon of a mutant Ras gene using a method such as homologous recombination. In addition, a translational regulatory element having translational inhibitory activity also can be introduced into a eukaryotic cell such that it can randomly integrate into the cell genome, thus providing a novel means to obtain a "knock out" phenotype in a cell.

The production of a genetically modified cell expressing a heterologous polypeptide, for example, is facilitated by including the nucleotide sequence of interest as one cistron of a polycistronic expressible polynucleotide, to which one or more translational regulatory elements of the invention, including one or more IRES elements is operatively linked. One or more other cistrons in the expressible polynucleotide can encode, for example, a reporter molecule such that cells containing the construct can be identified, selected and isolated. One or more other cistrons in the construct also can encode a second polypeptide that effects, for example, the level of transcription of the expressible polynucleotide in the genetically modified cell, or the activity of the expressed heterologous polypeptide in the cell.

Accordingly, the present invention also relates to a genetically modified eukaryotic cell produced by a method of the invention, as well as to a transgenic non-human eukaryotic organism containing or derived from such a genetically modified cell, a cell or tissue obtained from the transgenic non-human eukaryotic organism, and a cDNA or genomic DNA library prepared from the transgenic non-human eukaryotic organism or from a cell or tissue obtained from said transgenic non-human eukaryotic organism. Such a genetically modified cell or transgenic organism can be useful, for example, to produce a polypeptide of interest, or as a model system for a pathologic condition, for example, a condition characterized in part by overexpression or accumulation of a particular polypeptide.

The present invention further provides a method of altering translational activity in a eukaryotic cell, the method comprising introducing into the cell a synthetic translational regulatory element As disclosed herein, introduction of a translational regulatory element of the invention having translational enhancing activity can reduce the level of translation in a cell. While no mechanism for this action is proposed herein or, in fact, relevant to practicing a method of the invention, one possibility is that the element can bind to and sequester trans-acting translational regulatory factors such as eukaryotic initiation factors or the like, similar to effects seen with transcriptional regulatory elements when introduced into cells. Thus, by introducing a translational regulatory element of the invention having translational enhancing activity or IRES activity into a eukaryotic cell, the translational activity in the eukaryotic cell can be reduced or inhibited. Conversely, by introducing a translational regulatory element having translational inhibitory activity into a eukaryotic cell, translational activity in the cell is increased due, for example, to the sequestering of a trans-acting factor that otherwise binds to an endogenous translational inhibitory sequence in the cell to inhibit translation.

The present invention also provides a means to conveniently and efficiently select specific cells and cell populations. Identification of such cells is effected by introducing a construct containing a translational regulatory element, for example, an IRES element operatively linked to a nucleotide sequence encoding a reporter molecule such as a fluorescent protein or selectable marker. Where an IRES element is used, the IRES element can drive expression of a monocistronic reporter cassette or can drive expression of a second or other cistrons in a polycistronic cassette, one or more of which encode a reporter polypeptide and one or more others of which can encode any polypeptide or polypeptides of interest. Generally, in a polycistronic reporter, an IRES element is contained in an intercistronic position, particularly upstream of the cistron to be regulated by the IRES. Thus, desired cells can be selected based on expression of the reporter polypeptide driven by the translational regulatory element, and, if desired, the cell can be one that also expresses a heterologous polypeptide of interest, which can be co-expressed from the same construct as the reporter polypeptide.

Particularly usefull co-expressed reporter polypeptides can include cell surface polypeptides, which act as markers that permit immunocytometric or affinity chromatographic selection and isolation of the cells expressing the protein of interest; enzymes or other polypeptides that confer antibiotic resistance, which allow the use of a growth selection method to identify, select and isolate cells co-expressing the protein of interest; other enzymes that confer a unique reporting capability to a cell, for example, alkaline phosphatase, horseradish peroxidase or any other enzyme generally used for as a histologic or diagnostic reporter molecule. Such polypeptides, including a reporter polypeptide and co-expressed protein of interest can be expressed under in vivo or in vitro conditions and, similarly, the cells expressing the polypeptide can be identified, selected, or isolated under in vivo or in vitro conditions.

The present invention also provides methods for improving protein yields by a cell, which can be a cell in culture or a cell in an organism, through enhanced protein stability, enhanced cell stability and viability, and the like. Stability of expressed protein products can be improved using, for example, IRES mediated co-expression of proteins or peptides such as chaperone proteins, heat shock proteins, proteins such as superoxide dismutase and catalase, which decrease the levels of oxidizing agents in a cell, protease inhibitors, phosphatase inhibitors, and the like, which can enhance the stability of the protein of interest or a cell expressing the protein of interest, thereby enhancing the yield of the protein obtainable from the cell. For example, co-expression of protease inhibitors with a protein of interest can protect the protein from cellular proteases, thus prolonging the time the protein is present in a cell and increasing the yield obtainable from the cell. Similarly, enzyme inhibitors or modulators such as caspase inhibitors can maintain cellular integrity during expression of the protein of interest by prolonging the life of the cell. Antibiotics peptides such as magainins, defensins, cryptdins and the like also can be co-expressed with the protein of interest, thereby protecting the cell from microbial contamination, thus increasing the likelihood that the cells can be maintained in a healthy and productive state. Furthermore, by using concatemers of the disclosed translational regulatory elements, including concatemers of the same or different elements, very high levels of translation can be obtained and translation in particular cell types or at particular stages of the cell cycle can be obtained. Such methods are particularly valuable to the bioprocessing industry, which is involved in large scale manufacture of proteins for medical and industrial use.

Improved protein yields also can be obtained by using an IRES element for co-expressing a transcription factor specific for a promoter element contained in the construct comprising the IRES element, or for co-expressing translational regulatory factors such as translation eukaryotic initiation factors that are specific for the IRES or other translational regulatory elements contained in the construct. Such methods provide a means for enhancing cellular signaling in the environment of the cell producing the target protein. IRES mediated co-expression of agents that affect the cellular environment of the cell expressing a target protein can be particularly useful for in vivo diagnostic and therapeutic applications, as well as for in vitro bioproduction methods and as research tools. For example, the co-expressed agents can include proteins or peptides from the classes of neuromodulators, peptide/protein hormones, growth factors, adhesion proteins, cell media peptides, and the like.

The present invention also provides methods for producing complex proteins or protein systems. For example, IRES-mediated co-expression of the subunits of a multi-component protein has been reported (see, for example, U.S. Pat. No. 6,060,273). However, unique applications using the presently disclosed translational regulatory elements, including IRES elements, allow the co-expression of enzymes or pro-enzymes with specific substrates, prosthetic groups, allosteric modulators, processing enzymes, chaperones, and the like.

The following examples are intended to illustrate but not limit the invention.

EXAMPLE 1

Identification of a Modular IRES Element That Enhances Translational Activity

This example describes the identification and characterization of a nine nucleotide IRES element from the 5' untranslated region (5' UTR) of the mRNA encoding the Gtx homeodomain protein.

A. Identification of a Nine Nucle tide IRES Element in the Gtx 5' UTR

Dicistronic constructs were based on the pGL3-R2 (RP) and pGL3-R2 h (RPh) dicistronic reporter vectors (Chappell et al., *Proc. Natl. Acad. Sci. USA* 97:1536-1541, 2000, each of which is incorporated herein by reference; see, also, Stoneley et al., supra, 1998). These vectors encode a dicistronic mRNA, with the *Renilla* (sea pansy) luciferase gene upstream of the *Photinus* (firefly) luciferase gene. An SV40 promoter and enhancer drive expression. The RPh vector contains a 60 bp inverted repeat located 5' (upstream) of the first cistron. The 5' UTR of the Gtx mRNA (SEQ ID NO: 1; Komuro et al., supra, 1993) was synthesized as two overlapping oligonucleotides, amplified by PCR with Pfu DNA polymerase (Stratagene, La Jolla Calif.), and inserted into the intercistronic region as an Eco RI to Nco I fragment immediately upstream of the *Photinus* luciferase initiation codon in both the RP and RPh vectors. Other inserts were similarly cloned into the intercistronic region using the Eco RI and Nco I restriction sites, or using the Spe I and Eco RI restriction sites. The sequences of all constructs were verified. Plasmids containing the chloramphenicol acetyl transferase (CAT) gene instead of the *Photinus* luciferase gene were derived by deleting the luciferase gene and replacing it with the CAT gene using the Nco I and Bam HI restriction sites (RCh). The CAT gene was from the pCAT3 control vector (Promega; Madison Wis.).

Cell lines were obtained from ATCC and maintained according to their instructions. Dicistronic reporter constructs were transfected into cells using FuGENE 6 reagent (Roche; Indianapolis Ind.), according to the manufacturer's instructions. Transfection efficiencies were normalized by cotransfection with the pCMVβ vector (Clontech; Palo Alto Calif.). Cells were harvested after 24 hr and luciferase activity was determined using the dual reporter assay system (Promega). β-galactosidase activity was assayed using the Fluoreporter lacZ kit (Molecular Probes; Eugene Oreg.) and fluorescence was measured using the Millipore Cytofluor 2450 system. CAT enzyme activity was measured using n-butyryl CoA according to technical bulletin #84 (Promega).

Northern blot analysis was performed as described by Mauro and Edelman (supra, 1997) using RNA prepared by the guanidinium thiocyanate method from the neuronal cell line Neuro 2a (N2a; Chomczyjnski and Sacchi, *Anal. Biochem.* 162:156-159, 1987, which is incorporated by reference). Poly(A)$^+$ RNA was selected using Oligotex oligo(dT) beads (Qiagen; Chatsworth Calif.). Hybridizations were performed using Rapid hyb buffer (Amersham; Piscataway N.J.) with a probe containing the entire *Photinus* luciferase coding sequence. This probe was obtained by digesting the dicistronic construct at the Nco I and Sal I restriction sites. Hybridizations were performed at. 65° C.; wash stringency was 65° C. in 0.1× saline sodium citrate (SSC).

The 5' UTR of the Gtx mRNA (SEQ ID NO: 1) is 196 nucleotides in length (Komuro et al., supra, 1993; see, also, GenBank Accession No. L08074, ATG is at nucleotides 197 to 199) and contains several complementary sequence matches to 18S rRNA, one of which was the focus of a previous study (Hu et al., supra, 1999). In order to determine whether a sequence of 5' UTR can interact directly with complementary sequences in the 18S rRNA, the Gtx 5' UTR was inserted into the intercistronic region of the dicistronic mRNA (Gtx$_{1-196}$/RP), which contains the *Renilla* luciferase coding sequence as the first cistron and the *Photinus* luciferase coding sequence as the second cistron (Stoneley et al., supra, 1998). The presence of the 196 nucleotide Gtx 5' UTR enhanced expression of the downstream cistron about 7.2-fold over background in the rat neuronal N2a cell line and about 8.8-fold in the rat glioma C6 cell line. The IRES activity was approximately 47% of that of the encephalomyocarditis virus (EMCV) IRES in N2a cells and 84% of that of EMCV in C6 cells when tested in the same vector system (EMCV/RP). Translation of the β-globin mRNA is cap-dependent (Keiper and Rhoads, *Nucl. Acids Res.* 25:395-402, 1997). As such, insertion of the 5' UTR of the β-globin mRNA in the intercistronic region served as a control (no IRES activity; β-globin/RP).

In order to confirm that enhanced expression of the second cistron was not dependent on translation of the first cistron, translation of the first cistron was inhibited by introducing an inverted repeat, which has potential to form a stable hairpin structure, in the 5' UTR ($Gtx_{1-196}$/RPh). When normalized to the activity of the RP vector, the presence of the hairpin structure resulted in increased IRES activity up to 31-fold over background. Northern blot analysis using poly(A)+ RNA isolated from N2a cells transfected with the $Gtx_{1-196}$/RP vector and probed with a *Photinus* luciferase fragment showed that the cells expressed only a single detectable mRNA of the correct expected size. These results demonstrate that enhanced expression of the downstream *Photinus* luciferase gene was not due to the generation of a functional monocistronic mRNAs due, for example, to an unusual splicing event or RNA fragmentation.

In order to determine whether the Gtx 5' UTR contains shorter segments with IRES activity, the 5' UTR was sequentially deleted from the 5' and 3' ends, and was fragmented into 5 non-overlapping segments of approximately 40 nucleotides (see FIG. 1), each of which was tested for IRES activity. To minimize the contribution of the first cistron, the RPh vector was used for these constructs. All of the deleted and fragmented sequences examined had IRES activity, with the exception of constructs $Gtx_{120-196}$/RPh and $Gtx_{167-196}$/RPh. Deletion of nucleotides 167 to 196 of SEQ ID NO: 1 increased IRES activity to a level greater than that of the entire 5' UTR ($Gtx_{1-166}$/RPh and $Gtx_{120-166}$/RPh). These results indicate that either the 167 to 196 region of SEQ ID NO: 1 inhibits IRES activity, or the IRES activity exhibited by nucleotides 1 to 166 of SEQ ID NO: 1 is dependent on its location relative to the initiation codon.

The nucleotide sequence 133 to 141 (CCGGCGGGT; SEQ ID NO: 2), which is contained within the $Gtx_{120-166}$/RPh construct, is 100% complementary to nucleotides 1332 to 1124 of 18S rRNA, and has been shown to crosslink to its complement within intact 40S subunits (Hu et al., supra, 1999). The 9 nucleotide Gtx sequence (SEQ ID NO: 2) was directly tested for IRES activity. The spacing of the 9 nucleotide Gtx sequence relative to the initiation codon was maintained as in the $Gtx_{120-166}$/RPh construct by using a polynucleotide sequence identical to the whole β-globin 5' UTR (SEQ ID NO: 3), which lacks detectable IRES activity. IRES activity associated with this construct (see SEQ ID NO: 4) was about 3.4-fold over the background. These results demonstrate that a core 9 nucleotide sequence of the Gtx 5' UTR (SEQ ID NO: 2) has IRES activity. As such, this sequence is referred to as the Gtx IRES module (SEQ ID NO: 2).

B. Operatively Linked IRES Modules Enhance Translation Synergistically

Dicistronic constructs were generated containing 1 (SEQ ID NO: 5), 5 (SEQ ID NO: 6), or 10 (SEQ ID NO: 7) copies of the Gtx IRES module (SEQ ID NO: 2). The IRES modules were positioned beginning 25 nucleotides upstream of the initiation codon using β-globin 5' UTR sequences (see SEQ ID NOS: 5 to 7). Constructs with 5 or 10 copies of the IRES module were arbitrarily spaced 9 nucleotides from each other using a repeated segment of the β-globin 5' UTR (designated SI; see, for example, SEQ ID NO: 6). In N2a cells, IRES activity of the $Gtx_{133-144}$/RPh construct, which contained a single copy of the IRES module (SEQ ID NO: 5), was 2.5-fold over background; IRES activity of the $(Gtx_{133-144})_5$ $(SI)_5β$/RPh construct (5 copies; SEQ ID NO: 6) was 164-fold over background; and IRES activity of the $(Gtx_{133-144})_{10}$ $(SI)_5 9β$/RPh construct (10 copies; SEQ ID NO: 7) was 570-fold over background (IRES activities were normalized to activity of the parent RPh vector). In comparison, when normalized to the activity of the RP vector, IRES activity of the $(Gtx_{133-144})_{10}(SI)_9β$/RPh) construct was about 6,000-fold over background.

The ratio of *Photinus* luciferase activity to *Renilla* luciferase activity (P:R ratio) reflects the absolute increase in *Photinus* luciferase activity for all constructs except those that contain 5 or 10 copies of the $Gtx_{133-144}$ sequence with the SI spacer, in which the expression of both cistrons increased. The level of *Renilla* luciferase expression obtained with the $(Gtx_{133-144})_{10}(SI)_9β$/RPh construct was approximately 20-fold higher than that of construct RPh Northern blot analysis of mRNAs from N2a cells indicated that the mRNA levels were not significantly different Thus, it is unlikely that increased mRNA levels were responsible for the increased expression of the *Renilla* gene. A similar enhancement of both cistrons was observed when the tobacco necrosis virus enhancer was placed in the 3' UTR of a dicistronic mRNA (Meulewaeter et al., *RNA* 4:1347-1356, 1998).

Two other spacer sequences and a number of controls were examined to distinguish between the effects of the 9 nucleotide IRES module (SEQ ID NO: 2) and the spacer sequence. One spacer sequence included a different 9 nucleotide segment of the β-globin 5' UTR (designated SII; see SEQ ID NOS: 8 and 9) and the other included a poly($A$)$_9$ sequence (designated SIII; see SEQ ID NOS: 10 and 11). IRES activity increased up to 243-fold over background for constructs containing the SII spacer and up to 31-fold for constructs containing the SIII spacer. In all cases, increasing the number of copies of the IRES module resulted in increased IRES activity, although the level of activity was affected differently by the different spacer sequences. The different activities due to the spacer sequences may be due to an effect on the higher order structure of the mRNA, which may alter the presentation of the IRES modules to the translation machinery. Alternatively, some spacer sequences may introduce nucleotides that contribute to the IRES module, or that may themselves synergize with the IRES modules. However, control experiments using three different combinations of the spacer sequences alone—(SII/SIII)5 and (SII/SII), alternating in position as they do in the experimental constructs—revealed that the spacer sequences did not have any detectable IRES activity (but see Example 1C, below).

To confirm that the IRES activity observed with the $(Gtx_{133-144})_{10}(SI)_9β$/RPh construct was independent of the reporter gene, the *Photinus* luciferase gene was replaced with the CAT gene to produce the $(Gtx_{133-144})_{10}(SI)_9β$/RCh construct. Following transfection into N2a cells, CAT activity was determined by thin layer chromatography and liquid scintillation counting. CAT activity in lysates of cells transfected with this synthetic IRES construct was approximately 103-fold greater than that obtained for a construct containing the ECMV IRES linked to the CAT reporter gene (EMCV/RCh); the activity of a control construct (RCh) was indistinguishable from background. As for the RPh vector, the $(Gtx_{133-144})_{10}(SI)_9β$ synthetic IRES also increased *Renilla* expression significantly (about 6.1-fold) compared to the control RCh construct. The overall ratio of CAT expression to *Renilla* luciferase activity for the synthetic IRES $(Gtx_{133-144})_{10}(SI)_9β$/RCh was about 10.5-fold greater than that of the EMCV IRES. This is a high level of IRES activity, but is about 6-fold lower than that obtained with constructs containing the *Photinus* luciferase gene as the second cistron. Thus, the reporter cistron may have an influence on IRES activity, as was observed with the EMCV IRES (Kaminski and Jackson, *RNA* 4:626-638, 1998).

The activity of some viral IRESes can vary, depending on cell type (Borman et al., supra, 1997). Accordingly, the activity of the synthetic $(Gtx_{133-144})_{10}(SI)_9\beta/RCh$ IRES was examined in 11 different cell lines, including rat C6 glial cells, mouse N2a neuroblastoma cells, human SK-N-SH (SK) neuroblastoma cells, rat B104-1-1 (B104) neuroblastoma cells, mouse N1H-3T3 fibroblasts, human HeLa cervical carcinoma cells, mouse P19 embryonal carcinoma cells, rat NRK normal kidney cells, human K562 chronic myelogenous leukemia cells, mouse AtT-20 pituitary tumor cells, and mouse C2C12 muscle myoblast cells, and compared to that of the EMCV IRES. In all of the cell lines tested, the synthetic IRES was about 3.3-fold (NRK cells) to 63-fold (N2a cells) more active than that of the EMCV IRES.

To investigate the potential effects of distance between IRES modules, a series of constructs was generated containing 1 (SEQ ID NO: 12) or 2 (SEQ ID NOS: 13 to 15) copies of the Gtx IRES module (SEQ ID NO: 2). Spacing in constructs containing 2 copies of the Gtx IRES module varied from 9 to 54 nucleotides (see SEQ ID NOS: 13 to 15) using multiple copies of the SI spacer sequence, such that all of constructs were identical in size. The IRES activity obtained with 1 copy of the IRES module increased 2.8-fold when a second copy was introduced 9 nucleotides upstream of the first module. This activity decreased to about 2.1-fold and 1.3-fold as the distance between the IRES modules was increased to 27 and 54 nucleotides, respectively. Further experiments revealed that IRES activity continued to increase as the number of multimers was increased to 35, and that multimers of up to 50 Gtx modules (SEQ ID NO: 2), which was the most examined, had IRES activity, though somewhat less than that obtained using 35 copies. These results demonstrate that at least two and at least up to 50 of the Gtx IRES modules (SEQ ID NO: 2) can be operatively linked, and that the IRES activity of the combined modules can be varied by varying the distance between the IRES modules.

C. IRES Activity of Mutant Gtx Modules

Figure 2:
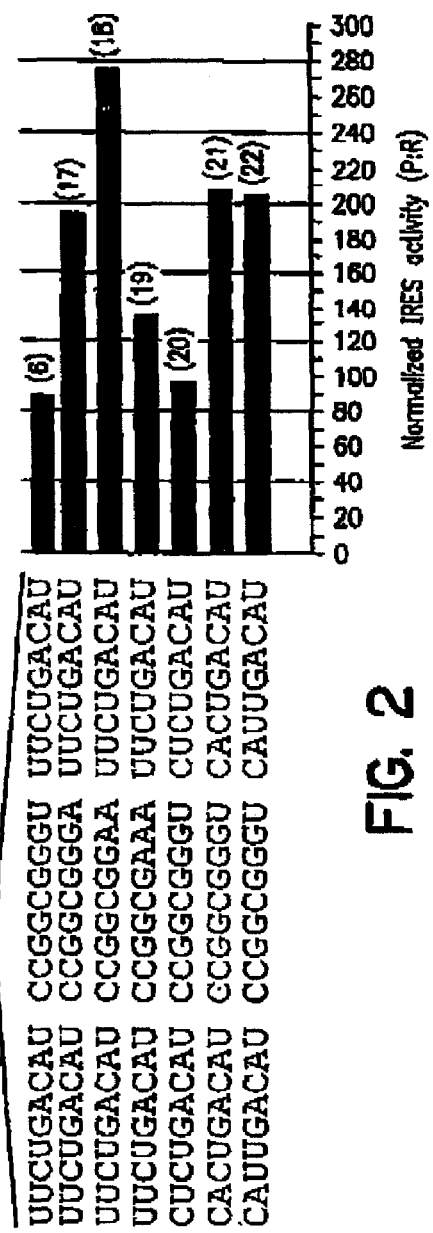
FIG. 2 shows a portion of the ribonucleotide sequences of various Gtx IRES module (SEQ ID NO: 2) constructs. SEQ ID NOS: of encoding deoxyribonucleotide sequences are indicated in parentheses. Nucleotide sequences as shown correspond, for example, to nucleotides 1 to 27 of SEQ ID NO:. 6 (5 copies of wild-type Gtx IRES), SEQ ID NOS: 17-19, containing 1, 2 or 3 substitutions at the 3' end of each Gtx IRES module in the repeated unit, and SEQ ID NOS: 20-22, containing 1, 2 or 3 substitutions at the 5' end of the spacer sequence in each repeated unit Relative IRES activity as a ratio of Renilla luciferase activity to Photinus luciferase activity (R:P) is shown, normalized to R:P activity of the RPh vector, alone.

Constructs containing 5 copies of the Gtx IRES module (SEQ ID NO: 2), each separated by the 9 nucleotide SI β-globin leader sequence, or 5 copies of a mutated version of the Gtx IRES module were cloned into the RPh vector, transfected into N2a cells, and examined for luciferase activity. Portions of these constructs are shown in FIG. 2 (compare SEQ ID NO: 6, which contains the wild type Gtx IRES module (SEQ ID NO: 2), with SEQ ID NOS: 17 to 19, which contain substitutions in the module; see, also, SEQ ID NOS: 20 to 22, which contain substitutions in the spacer sequence).

Substitution of adenosine residues at the 3' end of SEQ ID NO: 2 increased the IRES activity of the oligonucleotide (compare SEQ ID NO: 6 with SEQ ID NOS: 17 and 19). Changes in the composition of the spacer nucleotides adjacent to the Gtx IRES module either had no effect or also increased IRES activity (compare SEQ ID NO: 6 with SEQ ID NOS: 20 to 22). These results indicate that, when present in a particular context, the Gtx IRES module (SEQ ID NO: 2) provides a defined level of IRES activity, and that additional sequences based on the Gtx IRES module, as well as the context of the module with respect to flanking sequences can provide different levels of IRES activity.

EXAMPLE 2

Identification and Characterization of IRES Elements From Dendrictically Localized RNA Molecules This example demonstrates that RNA molecules that localize in dendrites contain 5' UTR nucleotide sequences that act as internal ribosome binding sites (IRESes)

A. Vector and Cell Lines

The 5' untranslated regions (5' UTRs) from the alpha subunit of Cam Kinase II (CamK IIa; SEQ ID NO: 23), dendrin (SEQ ID NO: 24), the activity-regulated cytoskeletal protein (ARC; SEQ ID NO: 25), microtubule-associated protein 2 (MAP2; SEQ ID NO: 26) and neurogranin (RC3; SEQ ID NO: 27) were obtained by RT-PCR amplification of rat adult hippocampal cDNA. Amplified 5' UTRs corresponded to the transcriptional start sites of the mRNAs and ended immediately 5' to the AUG translation start site. Primers were engineered with restriction endonuclease recognition sites for Eco RI and Nco I, to allow for directional cloning into the dicistronic vectors, RP and RPh, each of which encodes *Renilla* luciferase in the first cistron and *Photinus* luciferase in the second cistron (see Example 1A). All 5' UTRs were verified by sequence analysis.

The monocistronic luciferase vector, PM, was generated by substituting the *Photinus* luciferase gene from the RP construct for the EYFP (enhanced yellow fluorescent protein) open reading frame in the pEYFP-N1 vector, which contains a CMV promoter (Clontech) using the Eco RI and Xba I sites. As an internal control for transfection efficiency, the region of the chloramphenicol acetyl transferase (CAT) reporter gene construct of the pCAT3 control vector, which contains the SV40 promoter, CAT reporter gene and polyadenylation sequences (Promega), was also cloned into the monocistronic vector. The inverted repeat encoding the hairpin structure at the 5' end of RPh was amplified by PCR and inserted into the 5' region of the multiple cloning site in PM to yield the monocistronic hairpin construct PMh.

Monocistronic luciferase constructs were generated from the EYFP-N1 (Clontech) vector by replacing the gene encoding enhanced yellow fluorescent protein (EYFP) with the *Photinus* luciferase gene from the RP constructs using the Eco RI and Xba I restriction sites. The chloramphenicol acetyl transferase (CAT) gene was used as a control for transfection efficiency. A blunt ended Bam HI/Bgl II fragment containing the SV40 promoter, the CAT reporter gene, and polyadenylation sequences from the pCAT3 control vector (Promega) was cloned into the Ase I restriction site of these constructs after filling in the 3' recessed ends using the Klenow fragment of DNA polymerase I.

An EYFP construct (EYFP/NLS) was used to test the ability of the RC3 3' UTR to target mRNA to dendrites. This construct contains a nuclear localization signal (NLS) and a nuclear matrix binding site (NMBS) attached to the EYFP coding sequence to limit diffusion of EYFP from the cell body to the dendrites.

For in situ analysis of IRES activity, a dicistronic fluorophore vector was constructed that encodes enhanced cyan fluorescent protein (ECFP) as the first cistron and EYFP as the second cistron. Both fluorescent cistrons were modified to contain the mouse ornithine decarboxylase (ODC) destabilizing motif, which shortened the half-lives of these proteins to approximately 4 hr. This motif was obtained from the EGFP-N1 vector (Clontech) as a Bsr GI/Not I fragment. The mRNA expressed from this construct was targeted to dendrites using the 3' UTR from the RC3 gene.

Rat neural tumor B 104 cells, mouse neuroblastoma N2a cells, rat glial tumor C6 cells, mouse NIH 3T3 (3T3) fibroblasts, and mouse LMTK fibroblast cell lines were used for these studies. Cells were prepared and transiently transfected as previously described (Chappell et al., supra, 2000). Primary cultures of dissociated hippocampal neurons were cultured on poly-L-lysine coated chamber slides (Sporns and Jenkinson, *Neuroscience* 90:1057-1073, 1997, which is incorporated herein by reference). Culture media were exchanged twice weekly until neurons had reached maturation (about 21 to 25 days in vitro). Hippocampal neurons were transfected using calcium phosphate (Promega).

B. Reporter Gene Assays

Cells were prepared 12 to 14 hr prior to transfection by plating approximately 70,000 to 80,000 cells per well in a Falcon 6-well culture cluster. Cells were grown in DMEM with 10% FBS supplemented with 1% penicillin, streptomycin and glutamine. Dicistronic luciferase vectors (0.5 µg) were co-transfected with 0.2 µg of β-galactosidase reporter vector (CMVβ, Promega) per well using FuGENE 6 transfection reagent according to manufacturer's instructions (Boehringer; Germany). Transfected cells were grown for 22 to 24 hr, then rinsed briefly with PBS and lysed using 250 µd lysis buffer (Promega). Extracts (20 µl) were assayed for *Renilla* and *Photinus* luciferase activity using the dual luciferase assay kit (Promega). β-galactosidase was measured simultaneously using the fluorescent reporter β-gal assay kit (Molecular Probes; Eugene Oreg.). All constructs were transfected at least three times and individual transfections were performed in triplicate.

Monocistronic vector transfections were performed as above, but were not cotransfected with pCMVβ vector. B104 cells were transfected with monocistronic DNA constructs, then lysed and assayed for *Photinus* luciferase and CAT enzyme activity using single luciferase assay reagents (Promega) and a CAT enzyme assay kit (Promega) according to the manufacturer's instructions. Quantification of CAT activity was performed using a liquid scintillation counter. In experiments using the 4E-BP1 mutant (see below), either a plasmid expressing the dominant negative form of the eIF4E binding protein 4E-BP1, or an empty expression vector was co-transfected in parallel with the monocistronic constructs (Gingras et al., *Genes Devel.* 13:1422-1437, 1999, which is incorporated herein by reference).

C. Northern Blot Analysis

Total RNA from transfected cell lines was extracted using TRIZOL reagent (Gibco BRL; Gaithersburg Md.) and was size separated on a 1.3% agarose/formaldehyde gel. RNA was transferred to nylon membrane using capillary transfer, baked for 1 hr at 80° C., and prehybridized in 50% formamide, 5×SSC, 50 mM NAHPO$_4$, 1% SDS, 5% dextran sulfate, and 200 µg/ml polyadenylate for 2 hr at 70° C.

cDNA encoding the full-length *Photinus* luciferase reporter enzyme was directionally subcloned from the pGL3 (Promega) vector into the PBS SK II (+) vector (Stratagene; La Jolla Calif.) using Hind m and Xba I restriction sites. The resulting plasmid was linearized with Hind III and used as a template for synthesis by in vitro transcription of $^{32}$P-radiolabeled and digoxygenin (DIG)-labeled cRNA probes for northern blot analysis and in situ hybridization (Bizon et al., *J. Comp. Neurol.* 408:283-298, 1999; Pinkstaff et al., *Brain Res. Mol. Brain Res.* 55:265-276, 1998, each of which is incorporated herein by reference).

For fluorescent microscopic analysis, transfected neurons were fixed using 4% paraformaldehyde in phosphate buffered solution, placed under cover slips using Slow-Fade reagent (Molecular Probes), and visualized and quantified as described previously (Vanderklish et al., *Proc. Natl. Acad. Sci. USA* 97:2253-2258, 2000, which is incorporated herein by reference). Images were captured from each fluorescent filter channel for equal time periods and optimized so that the emission from both fluorophores was within a linear range. At least 20 images were quantified for each construct. Experimental data were analyzed for statistical significance using one-way analysis of variance (ANOVA) followed by an individual analysis of experimental versus control data points using a two-tailed Student's t-test. Results were considered significant at p<0.05.

D. Identification of Translational Regulatory Activity in the 5' UTRs of Dendritically Localized mRNAs To determine the effect on translation of the full length leader sequences of CamK IIA (SEQ ID NO: 23) dendrin (SEQ ID NO: 24), ARC (SEQ ID NO: 25), MAP2 (SEQ ID NO: 26), and RC3 (SEQ ID NO: 27), the sequences were inserted into the 5' UTR of a monocistronic reporter mRNA (PM), which encodes the *Photinus* luciferase protein, and examined for luciferase activity. The translation of β-globin mRNA is cap-dependent and the 5' UTR of the β-globin mRNA was included in these studies as a control. Monocistronic constructs were transfected into B104 cells. RNA blot analyses of total RNA from transfected B104 cells showed similar intensity of the autoradiographic bands between monocistronic constructs, indicating that the leader sequences do not affect the transcription or the stability of the monocistronic mRNAs.

The *Photinus* luciferase activity of each construct was determined, and the results were normalized for transfection efficiency using CAT activity, which was co-expressed from the PM plasmids. The β-globin 5' UTR had little effect on monocistronic translation. However, mRNA containing the MAP2 (SEQ ID NO: 26), ARC (SEQ ID NO: 25), or CamK IIa (SEQ ID NO: 23) 5' UTR showed enhanced levels of translation compared to the base vector by up to 2.5-fold. In contrast, monocistronic mRNA containing the dendrin 5' UTR (SEQ ID NO: 24) generated luciferase activity that was approximately 20% less than control values. These results indicate that the 5' UTRs (SEQ ID NOS: 23 to 26) can alter the overall levels of translation of monocistronic mRNAs, and do not alter the stability of the monocistronic mRNAs, which could result in corresponding alterations in luciferase activity.

To determine whether the cap-independent translation occurred by internal initiation, the 5' UTRs from CamK IIA (SEQ ID NO: 23) dendrin (SEQ ID NO: 24), ARC (SEQ ID NO: 25), and MAP2 (SEQ ID NO: 26) were cloned into the intercistronic region of the dicistronic luciferase vector, RP. Constructs were transfected into the neural cell lines (N2a cells, B104 cells, and C6 cells) and assayed for *Renilla* and *Photinus* luciferase activity.

Little or no translation of the second cistron (*Photinus* luciferase) occurs in the base vector (RP) and, consequently, only the first cistron (*Renilla* luciferase) was translated. However, if a sequence that can initiate translation is inserted between the two cistrons, then both the *Renilla* and *Photinus* luciferase cistrons will be translated. The ability of sequences within the intercistronic region to initiate translation of the second cistron is characteristically defined as IRES activity. The results are calculated as a ratio of *Photinus* to *Renilla* luciferase activity and compared to the base vector RP.

Insertion of the 5' UTR of β-globin, translation of which is cap-dependent, resulted in luciferase activity that was comparable to that of the RP vector alone. In contrast, insertion of the EMCV IRES into the intercistronic region resulted in about a 6 to 7-fold increase in translational activity as compared to RP. Insertion of the 5' UTRs of the dendritically localized mRNAs (SEQ ID NOS: 23 to 26) into the intercistronic region also resulted in increased translational activity, particularly with the ARC 5' UTR (SEQ ID NO: 18), which exhibited about 13-fold greater activity than the RP vector alone, and about 2-fold greater than that observed with the EMCV IRES in C6 cells. The MAP2 (SEQ ID NO: 26), α-CamK II (SEQ ID NO: 23), and dendrin (SEQ ID NO: 24) 5' UTRs generated approximately ⅓ to ½ the translation activity of EMCV, except that the IRES activity generated by the MAP2 5' UTR (SEQ ID NO: 26) was nearly equivalent to the activity of the EMCV IRES in C6 cells.

The relative levels of IRES activity between the different 5' UTRs generally were similar in all three neural cell lines. However, transfection of C6 cells consistently demonstrated higher ratios than N2a cells or B104 cells for all constructs. These results demonstrate that the 5' UTRs shown as SEQ ID NOS: 23 to 26, which are from dendritically localized mRNAs, contain sequences sufficient for the internal initiation of translation.

E. Internal Initiation in Non-Neural Cell Lines

To determine whether the 5' UTRs could also function as IRESes in non-neural cell types, the dicistronic constructs were transfected into 3T3 (fibroblast) cells and LMTK (kidney) cells. Each of the dicistronic constructs containing the 5' UTRs from the dendritically localized CamK IIA (SEQ ID NO: 23) dendrin (SEQ ID NO: 24), ARC (SEQ ID NO: 25), and MAP2 (SEQ ID NO: 26) mRNAs were expressed significantly above control values, demonstrating that IRES activity was conferred by these sequences in both neural and non-neural cell lines. Furthermore, the relative IRES activity generated from the dicistronic mRNAs in non-neural cells was similar to that observed in neural cell lines, with the ARC 5' UTR (SEQ ID NO: 25) being greater than the EMCV IRES, and the MAP2 5' UTR (SEQ ID NO: 26) being consistently greater than CamK IIa (SEQ ID NO: 23) and dendrin (SEQ ID NO: 24). However, the IRES activity in non-neural cells for dendrin, ARC, and MAP2 5' UTRs was higher than that observed for any of the neural cell lines. These results demonstrate that the 5'UTRs of these dendritically localized mRNAs can internally initiate translation in neural and non-neural cell lines, and that the overall level of IRES activity varies among cell types.

F. Dicistrnic mRNAs are not Alternatively Spliced

To determine if translation of the second cistron was due to alternative splicing of the dicistronic mRNAs resulting in the generation of two monocistronic messages, a northern blot analysis of total RNA from N2a cells transfected with the CamK IIA (SEQ ID NO: 23) dendrin (SEQ ID NO: 24), ARC (SEQ ID NO: 25), and MAP2 (SEQ ID NO: 26) dicistronic constructs was performed. Equivalent amounts of total RNA were hybridized with a cRNA probe derived from the full-length *Photinus* luciferase open reading frame. Using this probe, any message that is spliced is detected as a lower molecular weight fragment. However, no apparent lower molecular weight fragments were present, and the hybridized cRNA probe detected bands of the correct size for all dicistronic messages. This result demonstrates that the dicistronic constructs are translated as a single RNA species.

G. Translation of the Second Cistron is not Due to Re-Initiation or Read-Through In addition to internal initiation, translation of the second cistron also can be due to re-initiation and read-through from the first cistron. To eliminate this possibility, the CamK IIA (SEQ ID NO: 23) dendrin (SEQ ID NO: 24), ARC (SEQ ID NO: 25), and MAP2 (SEQ ID NO: 26) 5' UTRs were cloned into the RPh vector, which contains an inverted repeat sequence at the 5' end of the first cistron. The inverted repeat forms a stable hairpin loop structure and inhibits cap-dependent translation of the first cistron, dramatically reducing the levels of *Renilla* luciferase activity.

The dicistronic constructs were transfected into B104 cells and assayed for luciferase activity. Luciferase activity ratios for each of the four 5' UTRs was significantly greater than background RPh ratios, demonstrating that the 5' UTRs direct internal initiation of translation of the second cistron even when translation of the first cistron is inhibited. The ratio of *Photinus* to *Renilla* for the 5' UTRs from the dendritically localized mRNAs was elevated as compared to that of sequences lacking the hairpin structure, indicating that inhibition of cap-dependent translation can enhance cap-independent translation initiated by the 5' UTRs (SEQ ID NOS: 23 to 26). In comparison, the 5' UTR of β-globin was not significantly different from RPh luciferase activity, and the EMCV IRES activity was maintained in the presence of the hairpin. These results indicate that translation of the second cistron of dicistronic mRNAs is due to internal initiation, and not read-through or re-initiation from the first cistron, thus confining that the 5' UTRs (SEQ ID NOS: 23 to 26) of the dendritically localized mRNA molecules examined act as IRES elements.

H. 5' UTRs Confer Cap-Dependent and Cap-Independent Translation

To examine whether the CamK IIA, dendrin, ARC, and MAP2 5' UTRs (SEQ ID NOS: 23 to 26, respectively) function through both cap-dependent and cap-independent mechanisms of translation in monocistronic mRNAs, a hairpin was constructed at the 5' end of the monocistronic vector PM. This base vector (PMh) was used to examine the ability of the 5' UTRs to direct internal initiation of translation without the influence of ribosomal cap binding and scanning. The PMh-based constructs were transfected into B104 cells and assayed for both *Photinus* and CAT enzymatic activity.

The construct containing the β-globin 5' UTR exhibited luciferase activity that was slightly below that of the base vector, demonstrating that, as shown previously, the β-globin 5' UTR does not initiate translation internally. All four UTRs from the dendritically localized mRNAs (SEQ ID NOS: 23 to 26) generated luciferase activity above that produced by the base vector. As seen with the other constructs, the ARC 5' UTR (SEQ ID NO: 25) generated the most robust activity. However, the relative levels of luciferase activity produced by these 5' UTRs differed from that seen in monocistronics without hairpins. In particular, the dendrin 5' UTR (SEQ ID NO: 24), which demonstrated the least amount of IRES activity compared to the other 5' UTRs and actually decreased the level of luciferase activity in monocistronic RNA, produced a 3-fold increase in IRES activity in the hairpin-containing monocistronic RNA. Also, the MAP2 5' UTR (SEQ ID NO: 26) was not as robust when placed downstream of the hairpin as it was in the monocistronic mRNA. These results indicate that all four of the 5' UTRs (SEQ ID NOS: 23 to 26) utilize internal initiation of translation to different extents in the monocistronic RNAs.

Several mechanisms can regulate cap-dependent eukaryotic translation, including the modulation of eIF4E binding to the cap structure. To address whether these 5' UTRs could initiate translation without eIF4E binding to the cap, monocistronic 5' UTR constructs were co-transfected with a plasmid expressing a dominant negative form of the 4E-binding protein, 4E-BP1. 4E binding proteins can inhibit cap-dependent translation by sequestering eIF4E, thereby preventing eIF4E from binding the cap structure, and the eIF4E/4E binding protein complex can be dissociated due to phosphorylation of 4E binding protein. Mutation of the phosphorylation sites results in a dominant negative form of the 4E-BP1.

Cotransfected B104 cells were grown for 24 hr and assayed for *Photinus* luciferase activity. Luciferase activity from cells cotransfected with the plasmid encoding the mutant 4E-BP1 plasmid was expressed as a percentage of the luciferase activity in cells cotransfected with a control expression plasmid. Expression of the 4E-BP1 mutant reduced the luciferase activity from the PM and the β-globin monocistronics to 45% and 43%, respectively, of the luciferase activity from cells containing the same 5' UTR (SEQ ID NOS: 23 to 26) constructs transfected with the control expression plasmid. All of the constructs containing the 5' UTRs from the dendritically-localized mRNAs (SEQ ID NOS: 23 to 26) had luciferase activities that were above those of PM and β-globin. This result indicates that translation of these mRNAs occurs by both cap-dependent and -independent mechanisms.

The luciferase activity produced by the ARC (SEQ ID NO: 25) and MAP2 (SEQ ID NO: 26) 5' UTRs was reduced by 38% and 32% of control, respectively, yet remained approximately 45 to 50% higher than PM and β-globin, indicating both cap-dependent and cap-independent contributions to the translation of monocistronic mRNA. However, the CamK IIa 5' UTR (SEQ ID NO: 23), which strongly enhanced the translation of a monocistronic mRNA, was only reduced by about 20% of control when cotransfected with the 4E-BP1 mutant. Interestingly, the dendrin 5' UTR (SEQ ID NO: 24), which had the least IRES activity in dicistronic mRNAs, demonstrated luciferase activity that was only 13% less than control in the presence of 4E-BP1 mutant, indicating that IRES-dependent translation may be a major contributor to its overall levels of translation. These results are consistent with the results obtained using the hairpin constructs, and demonstrate that translation of monocistronic mRNAs containing a 5' UTRs from the four dendritically localized mRNAs (SEQ ID NOS: 23 to 26) occurs by both cap-dependent and cap-independent mechanisms.

I. Characterization of RC3 Translational Regulatory Element

The RC3 5' UTR (SEQ ID NO: 27) was also analyzed in the dual luciferase dicistronic mRNA. Northern blot analysis of the RC3 5' UTR in the RP construct resulted in the appearance of two mRNAs. Removal of the chimeric intron from the RP vector resulted in the production of one mRNA of the correct size predicted for the dicistronic mRNA. The leader sequence of β-globin mRNA as well as the EMCV IRES were cloned into the intercistronic region of this modified intron-less construct (RPi) and were analyzed in transiently transfected B104 cells. The resulting β-globin and EMCV P:R ratios were similar to those generated by the dicistronic mRNAs containing the chimeric intron. The P:R ratios produced from dicistronic mRNAs containing the RC3 5' UTR (SEQ ID NO: 27) was approximately 18-fold higher than RPi and approximately 3-fold higher than that obtained with the EMCV IRES. The P:R ratio obtained with constructs containing a hairpin structure 5' of the first cistron were not significantly different from those obtained with the RP construct. These results indicate that the RC3 leader sequence (SEQ ID NO: 27) also contains an IRES.

The activity of RC3 IRES was examined in primary hippocampal neurons. To analyze protein synthesis in dendrites, a monocistronic fluorophore reporter construct was engineered to target the mRNAs to dendritic processes. Targeting sequences have been identified within the 3' UTRs of several dendritically localized mRNAs (Kiebler and DesGroseillers, *Neuron* 25:19-28, 2000, which is incorporated herein by reference). To determine if the RC3 3' UTR functioned similarly, it was included in the 3' UTR of a monocistronic mRNA encoding EYFP along with a nuclear localization sequence (EYFP/NLS). The inclusion of the RC3 3' UTR resulted in expression of a significant amount of the fluorescent protein in dendrites of transfected neurons; constructs lacking this 3' UTR expressed the fluorescent protein only in the nucleus. This result suggests that the RC3 3'UTR could target mRNA to the dendrites of transfected neurons.

In situ hybridization confirmed that reporter mRNAs containing the RC3 3' UTR were localized throughout the processes of transfected hippocampal neurons, whereas reporter mRNAs lacking this 3' UTR were confined to the cell body. In addition, co-localization studies using the MAP2 antibody, which specifically stains dendrites, showed that mRNAs containing the RC3 3' UTR occurred within dendrites. These results validated the use of the RC3 3' UTR in directing mRNAs to the dendritic compartment and also demonstrated that translation occurs in dendrites.

To examine whether IRES mediated translation can occur within dendrites, a dicistronic mRNA containing ECFP as the first cistron, EYFP as the second cistron, and the RC3 3' UTR was used. To limit diffusion from the site of synthesis and facilitate quantification of de novo local protein synthesis, both fluorescent proteins were engineered to contain the mouse ODC destabilizing motif, which shortened the half-lives of these proteins to approximately four hours. As an initial analysis of the dicistronic fluorophore mRNAs, the constructs were tested in transfected N2a cells; IRES activities using this construct were similar to those observed using the dual luciferase vector.

Hippocampal neurons were transfected with dicistronic ECFP/EYFP constructs containing the 5' leader sequences from β-globin and RC3 (SEQ ID NO: 27) mRNAs within the intercistronic region. Fluorescence measurements were taken from the cell body as well as from the dendrites. Fluorescent overlay images using a ECFP and EYPF filter were taken from the dendritic fields of two neurons transfected with dicistronic fluorophore constructs containing either the β-globin or RC3 leader sequence in the intercistronic region, respectively. Transfection of hippocampal neurons with the dicistronic construct containing the β-globin 5' UTR resulted in mainly cap-dependent ECFP expression (visualized as cyan). However, the mRNA containing the RC3 leader sequence (SEQ ID NO: 27) demonstrated both cap-dependent translation and IRES-dependent translation (visualized as yellow) generating turquoise. Fluorescence activity of both cistrons was quantified from images and calculated as a yellow:cyan ratio.

The results demonstrated that the RC3 leader functioned as an IRES in both the cell body and the dendrites. Distribution of the activity of the RC3 IRES was punctate in the dendrites, indicating that activity was increased near synapses. In addition, the relative activity of the RC3 IRES (SEQ ID NO: 27) was approximately 2-fold more active in the dendrites than in the cell body. A northern blot of these dicistronic fluorophore mRNAs contained a single hybridizing band of the correct molecular weight.

Since many synaptic modifications do not persist when translation is inhibited, translation has been suggested to have an essential role in mediating changes in the morphology and efficacy of individual synapses in response to synaptic activity. Moreover, it is thought that some synaptic changes result from translation at post-synaptic sites rather than from cell-wide changes in protein synthesis. Such local translation would enable different synapses to be modified independently within the same cell. Evidence to support the notion of local protein synthesis includes the observations that components of the translation machinery occur in dendrites, that protein synthesis can occur at these cellular processes, and that many dendritically localized mRNAs encode proteins that are integral to synaptic modifications, including structural proteins (ARC, MAP2), growth factors, ionotropic receptors, and kinases (CamK IIa; see Kuhl and Skehel, *Curr. Opin. Neurobiol.* 8:600-606, 1998). These observations suggest that translation in dendrites is used to rapidly and locally synthesize some of the proteins required to strengthen active synapses.

As disclosed herein, the leader sequences of five dendritically localized mRNAs (SEQ ID NOS: 23 to 27) contain IRES activity, which mediates cap-independent translation. In addition, translation mediated by the RC3 5' UTR (SEQ ID NO: 27) occurred by both cap-dependent and cap-independent mechanisms within dendrites of cultured hippocampal neurons. Furthermore, translation by the cap-independent mechanism was relatively more efficient in the dendrite than in the cell body.

These 5' UTR sequences having IRES activity can serve to ensure or regulate translation of specific messages under varying conditions and can be involved in effecting synaptic plasticity. The identification of an IRES in the 5' UTR of the mRNA encoding the alpha subunit of Cam Kinase II is consistent with results showing increased translation of this mRNA following treatment of developing synapses with NMDA receptor agonists, even though total protein synthesis was impaired (Scheetz et al., *Nat. Neurosci.* 3:211-216, 2000). It has also been reported that the 5' UTR of the mRNA encoding Pim kinase, a protein that has recently been implicated in the stabilization of LTP also contains an IRES (Johannes et al., *Proc. Natl. Acad. Sci. USA* 96:13118-13123, 1999).

Inasmuch as ribosomes and initiation factors are present at low concentrations in dendrites, IRESes can be used by dendritically localized mRNAs to increase their ability to recruit the translation machinery within this cellular compartment. Indeed, IRESes appear to be used by some mRNAs when cap-dependent translation is reduced or blocked. For instance, overall levels of translation are reduced during apoptosis and during various types of cellular stress such as ischemia (Sheikh and Fornace, *Oncogene* 18:6121-612, 1999) and in these situations, IRES-mediated translation continues (Holcik et al., *Nat. Cell. Biol.* 1: 190-192, 1999; Stein et al., *Mol. Cell. Biol.* 18:3112-3119, 1998; Stoneley et al., *Mol. Cell. Biol.* 20:1162-1169, 2000). In addition, it has been reported that synaptic activity leads to an increase in protein synthesis in or near the active synapses, an increase that could saturate the cap-dependent translation machinery in dendrites. Thus, internal initiation can provide a means to initiate translation of dendritically localized messages in response to synaptic stimuli.

EXAMPLE 3

Identification of Translational Regulatory Elements That are Active in Growing Yeast Cells This example demonstrates that translational regulatory elements are present in mRNAs encoded in yeast cells, and that isolated elements of the yeast mRNA sequences have translational regulatory activity in vegetatively growing yeast cells.

In higher eukaryotes, translation of some mRNAs occurs by internal initiation. It is not known, however, whether this mechanism is used to initiate the translation of any yeast mRNAs. As disclosed herein, naturally occurring nucleotide sequences that function as IRES elements within the 5' leader sequences of *Saccharomyces cerevisiae* YAP1 and p150 mRNAs were identified. When tested in the 5' UTRs of monocistronic reporter genes, both leader sequences enhanced translation efficiency in vegetatively growing yeast cells. Moreover, when tested in the intercistronic region of dicistronic mRNAs, both sequences exhibited IRES activity that functioned in living yeast cells. The activity of the p150 leader was much greater than that of the YAP1 leader. Further analyses of the p150 IRES revealed several non-overlapping segments that independently mediated internal initiation. These results demonstrate that the p150 IRES has a modular structure similar to IRES elements contained within some cellular mRNAs of higher eukaryotes. Both YAP1 and p150 leaders contained several complementary sequence matches to yeast 18S rRNA.

The plasmid pMyr (Stratagene) was used as backbone for both dicistronic and monocistronic constructs. An adaptor containing restriction sites Hind m, Pst I, Nhe I, Eco RI, Nco I, and Xba I was introduced into the pMyr vector immediately downstream of the GAL1 promoter, using Hind III and Xba I as cloning sites. The PstI and XbaI sites were used as cloning sites for a fragment from the RPh dicistronic reporter vector (see Example 1A). The resulting construct, pMyr-RP, encodes a dicistronic mRNA that encodes *Renilla* (sea pansy) and *Photinus* (firefly) luciferase proteins as the first (upstream) and second (downstream) cistrons, respectively. These cloning steps resulted in a 5' UTR that differs slightly from that in the RP mRNA described previously (Example 1A). The CYC1 terminator sequence contained within pMyr-1 vector provides signals for termination of transcription and polyadenylation.

The p150, YAP1, and CLN3 leader sequences were PCR amplified using yeast genomic DNA as a template. These leader sequences were cloned into the intercistronic region of the pMyr-RP vector using Eco RI and Nco I restriction sites that were introduced at the 5' and 3' ends of the leader sequences to generate constructs designated as pMyr-p150/RP, pMyr-YAP1/RP, and pMyr-CLN3/RP. A hairpin structure with a predicted stability of –50 kcal mol$^{-1}$ (Stoneley et al., supra, 1998) was introduced into the 5' UTR of the dicistronic constructs to generate pMyr-p150/RPh, pMyr-YAP1/RPh, and pMyr-CLN3/RPh. Deletions and fragments of the p150 leader were generated by PCR amplification of the p150 sequence, again using Eco RI and Nco I as cloning sites.

Monocistronic constructs containing the *Photinus* luciferase gene were generated in the modified pMyr vector. The *Photinus* luciferase gene was obtained from the pGL3 control vector (Promega) as an Nco I/Xba I fragment and cloned using these same sites to generate construct pMyr/P. The leader sequences from YAP1, p150, and CLN3 mRNAs, as well as the hairpin structure were cloned into the pMyr/P vector using the same restriction sites used for the dicistronic constructs. Constructs containing the CAT gene were cloned into the pGAD10 vector (Clontech). The pGAD10 vector was digested with Hind III and an adaptor containing restriction sites Hind III, Pst I, Nhe I, Eco RI, Nco I, and Xba I was introduced into this site, which is immediately downstream of the ADH promoter. The CAT gene was obtained from the pCAT3 control vector (Promega) and cloned into the modified pGAD10 vector using Nco I and Xba I restriction sites. The p150 leader sequence was introduced into this vector as an Eco RI/Nco I fragment to generate the construct designated p150/CAT. The hairpin structure described above was introduced 5' of this leader sequence to generate the construct designated p150/CATh.

The yeast strain EGY48 (MATα, his3, trp1, ura3, LexA$_{op(x6)}$-LEU2; Clontech) was used throughout the study. Yeast strains harboring the pMyr based plasmids were grown overnight in 4 ml synthetic defined medium (SD) with uracil and glucose. The following morning, cells were harvested, washed with 4 ml H$_2$O, and grown for 3 hr in 4 ml SD medium without uracil with the addition of 2% galactose and 1% raffinose. Cells harboring the pGAD10 constructs did not require induction and were cultured in 4 ml SD/Ura glucose medium overnight. Cells were lysed with 1× lysis buffer (diluted freshly from 5× stock; Promega) in tubes with glass beads. Tubes were vortexed twice for 30 sec and recovered in a microfuge spun at top speed for 3 min at 4° C. The supernatant was recovered and 20 μl of the lysate was used to assay luciferase activities using the dual reporter assay system (Promega). CAT activity was measured using N-butyl CoA according to technical bulletin no. 84 (Promega).

RNA was isolated from 4 ml cell culture samples. Cells were pelleted, washed with water, and resuspended in 400 μl of TES buffer (100 mM Tris-HCl, pH 7.5, 10 mM EDTA, 0.5% SDS). RNA was extracted using preheated phenol (65° C.); the mixture was vortexed for 1 min and incubated at 65° C. for one hr. Samples were put on ice for 5 min, then centrifuged at 15,000 rpm for 5 min and the top aqueous phase was collected, re-extracted with phenol once and chloroform once. RNA was precipitated with isopropanol, the precipitate was washed with 70% ethanol, dried and dissolved in water. RNA samples were separated by gel electrophoresis using 1% formaldehyde/agarose gels and transferred to Nytran Super-Charge nylon membrane (Schleicher & Schuell). The blots were probed with full-length fire-fly luciferase RNA anti-sense probe that was labeled with $^{32}P$.

A. Analysis of YAP1 5' UTR

The 164 nucleotide YAP1 leader sequence (SEQ ID NO: 28) was examined for translational regulatory activity in the 5' UTR of a firefly (*Photinus*) luciferase reporter mRNA (YAP1/P). Cells were transformed with constructs expressing the parent *Photinus* (-/P) mRNA, the YAP1/P mRNA, or the 364 nucleotide 5' leader of the CLN3/P mRNA as a spacer control. Transcription of these monocistronic mRNAs was under control of the GAL1 promoter; mRNA expression was induced with galactose, cells were lysed after 3 hr, and luciferase activities determined and normalized to *Photinus* luciferase mRNA levels. Translation efficiency of the YAP1/P mRNA was approximately 10-fold greater than that of either the control -/P or CLN3/P mRNAs. This result indicates that the YAP1 5' UTR has translational enhancing activity.

To determine whether the translation mediated by the YAP1 transcribed leader sequence has a cap-independent component, it was tested in a dicistronic mRNA for its ability to mediate internal initiation. The leader sequence of YAP1 mRNA was placed in the intercistronic region of a dual luciferase dicistronic mRNA and examined for IRES activity. In these mRNA transcripts, the upstream cistron encodes *Renilla* (sea pansy) luciferase and the downstream cistron encodes *Photinus* luciferase. Cells were transformed with constructs encoding the parent RP mRNA, or with constructs containing the YAP1 or CLN3 leaders in the intercistronic region of the RP mRNA. The YAP1 leader sequence enhanced the translation of the downstream Photinus luciferase cistron approximately S-fold relative to that of the RP mRNA. In contrast, the CLN3 leader had almost no effect on the expression of the second cistron relative to that of the RP mRNA.

Hairpin structures were inserted in the discistronic constructs upstream of the *Renilla* luciferase gene to block scanning and, thereby, reduce the translation of this reporter molecule. The hairpin structures blocked *Renilla* luciferase expression by greater than 90%. Nevertheless, the YAP1 leader permitted translation of the *Photinus* luciferase gene, even when translation of the *Renilla* luciferase gene was blocked. This result demonstrates that the YAP1 leader did not increase expression of the second cistron by reinitiation or leaky scanning.

To exclude the possibility that enhanced expression of the downstream cistron was from shorter, monocistronic mRNAs generated by mechanisms such as RNA fragmentation or an unusual splicing event, RNA was isolated from transformed cells and analyzed by northern blot analysis using a probe to the downstream *Photinus* luciferase gene. The results demonstrated that the dicistronic mRNAs were intact. Thus, translation of the second cistron was not due to initiation via shorter transcripts. Together, these results demonstrate that the YAP 1 5' UTR comprises a nucleotide sequence that has IRES activity and that has translational enhancing activity.

B. Analysis of p150 5' UTR

The yeast p150 5' UTR also was examined for translational regulatory activity. The 5' leader of the mRNA encoding the p150 protein was determined by primer extension analysis to contain 508 nucleotides (SEQ ID NO: 29 see, also, Goyer et al., *Mol. Cell. Biol.* 13:4860-4874, 1993, which is incorporated herein by reference). This sequence contains 11 open reading frames (ORFs) and does not appear to contain or be part of an intron (Costanzo et al., *Nucl. Acids Res.* 28:73-76, 2000, which is incorporated herein by reference), consistent with the observation that only 4% of yeast genes contain introns, 90% of which encode ribosomal proteins. The presence of the upstream ORFs in the p150 leader might be expected to inhibit translation by a scanning mechanism.

The p150 sequence was tested in the 5' UTR of a monocistronic reporter mRNA. Constructs containing this sequence enhanced the translation efficiency of the reporter gene up to 10-fold. However, the analysis was complicated by the appearance of a second band approximately 1 kb, which may be a partial degradation product of the luciferase mRNA; this RNA was too short to encode a functional *Photinus* luciferase protein. Accordingly, the p150 leader was tested in the 5' UTR of the CAT reporter gene to further evaluate whether it was functioning as a translational enhancer. The results obtained using the CAT reporter construct were similar to those obtained with the *Photinus* luciferase reporter gene; the p150 leader sequence enhanced the translation efficiency of the CAT reporter gene 9-fold.

To determine whether any translation mediated by the p150 5' leader was cap-independent, a hairpin structure was inserted at the 5' end of this construct. Although the hairpin structure inhibited translation of a control CAT mRNA by greater than 90%, translation mediated by the p150 leader sequence was not inhibited but, instead, was enhanced by approximately 3-fold. The CAT mRNA levels did not appear to be affected. These results demonstrate that the translation mediated by this leader sequence is cap-independent.

To confirm that translation was cap-independent, the p150 leader was tested in the intercistronic region of the dual luciferase RP dicistronic mRNA. In this location, the p150 leader functioned as a potent IRES, enhancing translation of the downstream *Photinus* luciferase cistron approximately 200-fold relative to that of the RP parent vector. This increase in *Photinus* luciferase activity in the p150/RP mRNA resulted in *Photinus* luciferase protein levels that were approximately twice those of *Renilla* protein levels.

Blocking the translation of the upstream *Renilla* luciferase gene with a hairpin structure resulted in an even greater enhancement of the *Photinus:Renilla* luciferase ratio, indicating that the translation facilitated by this sequence was not dependent on the translation of the upstream *Renilla* luciferase cistron. As with the findings with YAP1, the enhanced expression of the downstream cistron was not associated with RNA fragmentation or unusual splicing events.

The p150 leader sequence was sequentially deleted from the 5' end and fragmented into shorter segments, including fragments consisting of nucleotides 100 to 508, 160 to 508, 250 to 508, 375 to 508, 429 to 508, 481 to 508, 250 to 390, and 1 to 250 of SEQ ID NO: 29, each of which was tested for IRES activity. Most of the IRES activity was associated with nucleotides 160 to 508 of SEQ ID NO: 29. However, all of the fragments examined demonstrated some level of IRES activity. Furthermore, deletion of nucleotides 1 to 100 or nucleotides 100 to 160 of SEQ ID NO: 29 increased translation by internal initiation, indicating that this 160 nucleotide region contains translational inhibitory sequences, which can inhibit IRES activity. The leader sequence in construct p150(250-508) corresponds to that of a shorter leader sequence that occurs naturally (Goyer et al., supra, 1993). This shorter leader sequence has a level of IRES activity that is similar to that of the entire 508 nucleotide leader (SEQ ID NO: 29).

It was previously noted that many eukaryotic mRNAs contain short complementary sequence matches to 18S rRNA, raising the possibility that ribosome recruitment at some cellular IRESes might occur by base pairing between mRNA and 18S rRNA (Chappell et al., supra, 2000; Mauro and Edelman, supra, 1997; Hu et al., supra, 1999; Tranque et al., supra, 1998). Comparison of the YAP1 and p150 leader sequences to yeast 18S rRNA identified two (SEQ ID NOS: 30 and 32) and four (SE ID NOS: 34, 36, 38 and 40) complementary sequence matches, respectively, which contained stretches of up to 10 nucleotides of perfect complementarity (FIG. 3). In addition, two of the matches are part of more extensive complementary matches of up to 25 nucleotides with 84% complementarity. The complementary match at nucleotides 130 to 142 of the p150 IRES (SEQ ID NO: 34) is correlated with a 60 nucleotide segment of the p150 5' UTR that can inhibit IRES activity. Another complementary match of the p150 IRES at nucleotides 165 to 183 (SEQ ID NO: 36) is correlated with a 90 nucleotide segment of the IRES that contributes to internal initiation. Two other complementary matches of the p150 IRES at nucleotides 423 to 437 (SEQ ID NO: 38) and nucleotides 437 to 461 (SEQ ID NO: 40) are partially or fully contained within a 52 nucleotide segment with IRES activity.

It was previously suggested that the yeast translation machinery may be capable of mediating internal initiation (Iizuka et al., *Mol. Cell. Biol.* 14:7322-7330, 1994; Paz et al., *J. Biol. Chem.* 274:21741-21745, 1999, each of which is incorporated herein by reference). The present results demonstrate unequivocally that yeast IRES sequences contained within the YAP1 and p150 leader sequences are functional in vegetatively growing cells. In addition, numerous sequences sharing complementarity with yeast 18S rRNA were identified within both leader sequences (FIG. 3). Many other mRNAs and cellular IRESes contain similar features, and the complementary sequence matches to 18S rRNA can function as cis-acting sequences that affect translation (see, for example, Chappell et al., supra, 2000). In the case of the Gtx IRES module (SEQ ID NO: 2), this segment is 100% complementary to a sequence of 18S rRNA. Recruitment of ribosomes at this site appeared to involve base pairing to 18S rRNA within 40S ribosomal subunits. These results indicate that recruitment of ribosomes at some cellular IRES element, including the yeast YAP1 and p150 IRESes, can occur directly due to base pairing to rRNA, a mechanism consistent with the modular nature of these cellular IRES elements.

The leader sequence of the YAP1 mRNA contained an IRES element that contributed to the efficient translation of this mRNA. Sequence features of this leader previously have been shown to affect translation and mRNA stability (Vilela et al., *Nucl. Acids Res.* 26:1150-1159, 1998; Ruiz-Echevarria and Peltz, *Cell* 101:741-751, 2000, each of which is incorporated herein by reference). One of these features, a short upstream open reading frame (uORF) did not inhibit translation of the main ORF, even though it was recognized by a large fraction of the scanning ribosome. Inasmuch as uORFs generally inhibit the translation of downstream cistrons, these results indicated that reinitiation and leaky scanning were also involved in the efficient translation of the YAP1 mRNA.

The p150 IRES element was particularly active. Although most of the IRES activity was localized to nucleotides 160 to 508 (SEQ ID NO: 29), the IRES boundaries were not distinct. Moreover, several non-overlapping segments functioned independently, suggesting that this IRES has a modular composition. Using methods as described in Example 1, which identified the IRES module (SEQ ID NO: 2) present in the Gtx homeodomain protein, IRES modules in the p150 5' UTR similarly can be isolated.

The notion that short nucleotide sequences can recruit the translation machinery is not consistent with the proposal that higher order RNA conformations are uniformly important for the activity of some cellular IRESes. Indeed, the results obtained from deletion and fragment analyses of IRESes contained within other mammalian and insect cellular mRNAs indicates that many of these IRESes may also be modular (see, for example, Yang and Sarnow, *Nucl. Acids Res.* 25:2800-2807, 1997; Sella et al., *Mol. Cell Biol.* 19:5429-5440, 1999). The modular composition of cellular IRESes contrasts with those of viruses. For example, in picornaviruses, the IRESes comprise several hundred nucleotides and contain RNA conformations that appear to be highly conserved and that are important for activity.

It is not known how widely internal initiation is used by yeast or higher eukaryotic mRNAs. The identification of numerous insect and mammalian IRESes may reflect a more extensive use of this mechanism in higher eukaryotes, or it may reflect incidental bias that has resulted in the evaluation of many more mRNAs from insects and mammals than from yeast. Some mammalian IRESes do not function in living yeast. In the case of poliovirus, the inactivity of its IRES in *S. cerevisiae* reflects a specific blockage that occurs via a short inhibitory RNA. The inactivity of some mammalian IRESes in yeast may also reflect trans-acting factor requirements that are not provided by yeast cells or differences related to the ability of a sequence to bind a component of the translation machinery that is not identical to that in yeast. For example, p 150 is the yeast homologue of mammalian translation initiation factor eIF4G, but the two are not functionally interchangeable.

In higher eukaryotes, IRESes are used by some mRNAs during the G2/M phase of the cell cycle and under conditions that reduce cap-dependent translation, as seen, for example, during different types of stress. In yeast, internal initiation may also be used to facilitate the translation of essential genes under similar conditions, including during periods of nutritional deficiency. It may be significant that IRESes were identified within the YAP1 and p150 leader sequences given that overexpression of YAP1 confers general resistance to many compounds, and that expression of p150 when cap-dependent translation is reduced can allow translation of other mRNAs under adverse conditions.

The identification of yeast IRESes that function in vegetatively growing cells suggests that yeast and higher eukaryotes use similar mechanisms to initiate translation. The analysis of these mechanisms should be facilitated in yeast, since many strains of yeast having mutations in genes involved in translation are available. The ability to easily manipulate this organism genetically can facilitate the identification of specific factors involved in internal initiation and confirmation that base pairing between certain IRES sequences and 18S rRNA is important for recruitment of ribosomes at these sites. In addition to these scientific interests, the identification of yeast IRESes that function as translational enhancers in monocistronic mRNAs also provides numerous applications for bioengineering.

EXAMPLE 4

Identification and Characterization of Synetc Ires Elements

This example demonstrates that translational regulatory elements, including IRES elements, can be identified by screening libraries of random oligonucleotides.

A. Retroviral Vector

Retroviruses are extremely useful tools to deliver genes into eukaryotic cells both in culture and in whole animals. Currently, however, most retroviral vectors are not tailored for tissue specific or developmental stage specific delivery of genes. Thus, a benefit of screening a retroviral library for functional synthetic translational regulatory elements as disclosed herein is the potential to create novel retroviruses with exquisite target specificity. Such vectors can be extremely useful for generating cell lines or transgenic animals for diagnostic screening procedures and drug development. In addition, such vectors can be useful for gene therapy in humans.

A retrovirus is a single stranded RNA virus that infects a cell and integrates into the genome of a cell by copying itself into a double stranded DNA molecule by reverse transcription. The integrated retrovirus genome is referred to as a provirus. Retroviruses have a two stage life cycle, existing in both an RNA and a DNA form. The RNA form of the virus is packaged into an infectious particle that is coated with a glycoprotein that is recognized by receptors on the host cell. This interaction promotes a receptor mediated internalization event, resulting in exceptionally efficient delivery of the viral genome into the cell. After transport to the cell nucleus and uncoating, the RNA genome is reverse transcribed into a DNA form (a provirus). During the reverse transcription process, the provirus integrates into the host cell genome. Retroviruses do not integrate in a completely random fashion, but instead have a distinct preference for integration into regions of the genome that are transcriptionally competent. This characteristic reduces the likelihood that the provirus will be silenced by integration into a transcriptionally repressive domain.

In a recombinant retrovirus, the entire coding region of the virus is removed and replaced with a transgene. This replacement is done by standard molecular biological techniques using a proviral version of the virus that is propagated as a bacterial plasmid (a pro-retroviral vector). However, other sequences in the retrovirus genome are required for the functions of viral transcription and packaging, including genes encoding the viral gag and pol proteins, and the viral glycoprotein coat. While such sequences can be removed from the pro-retroviral plasmid, they must be provided in trans, for example, on other plasmids that are introduced into the host cell via cellular transfection in order to obtain a fully functional recombinant virus. Alternatively, these helper functions can be designed to be integrated into the cellular genome of the viral packaging cell line.

Retroviruses have two viral promoters called long terminal repeats (LTRs), one located at each end of the viral genome. The upstream LTR is responsible for promoting transcription of the DNA provirus into the RNA form. The downstream LTR is not used for transcription during the RNA phase of the life cycle. However, during reverse transcription of the RNA into the DNA provirus, the downstream LTR provides a template for the replication of the upstream LTR. Thus, native retroviruses contain identical sequences in their upstream and downstream LTRs.

Figure 4:
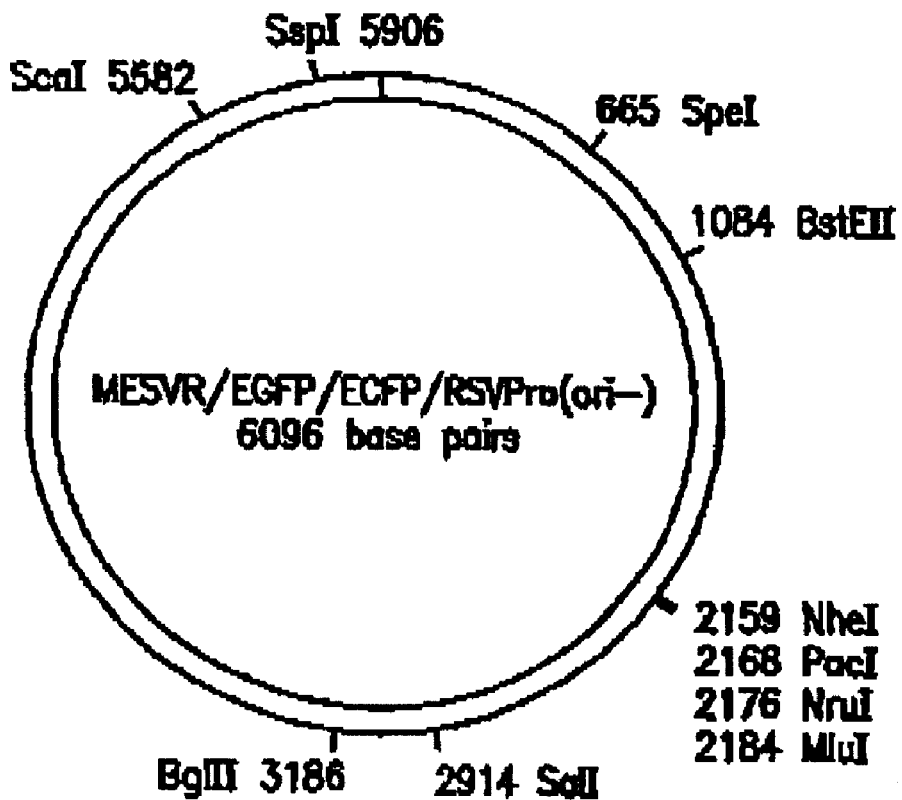
FIG. 4 is a map of the MESVR/EGFP/ECFP/RSVPro(ori) vector (SEQ ID NO: 16) showing the positions of unique restriction endonuclease recognition sites.

The recombinant retroviral vector designed for the IRES selection procedure was designated MESVR/EGFP/ECFP/RSVPro (SEQ ID NO: 16; see, also, FIG. 4). This vector was based on the MESV/IRESneo (Owens et al., *Cancer Res.*, 58:2020-2028 (1998); Mooslehner et al, *J. Virol.*, 64:3056-3058, 1990; Rohdewohld et al, *J. Virol*, 61:336-343, 1987, each of which is incorporated herein by reference). MESV is a C-type retrovirus that was modified to remove sequences that are necessary for independent replication. As such, the virus can only replicate with the assistance of helper genes that encode the proteins required for viral genome packaging and insertion into the host genome.

Features of the MESVR/EGFP/ECFP/RSVPro vector include that 1) a multiple cloning site was introduced into the downstream LTR for insertion of the exogenous sequences that can regulate transcriptional activity of a transgene encoded by the recombinant retrovirus, and the endogenous viral core promoter was replaced with a strong basal promoter to potentiate transcription promoting activity of inserted sequences; 2) a mutated EGFP encoding sequence followed by a multiple cloning site to allow insertion of elements to be tested sequences and a sequence encoding ECFP to allow assay of translational activity on a single cell basis was introduced; 3) enhancer elements in the upstream LTR were replaced with those from RSV to drive higher levels of RNA genome production in the packaging cells; and 4) an SV40 origin of replication was inserted in order to increase the copy number of the retroviral plasmids in the packaging cells. The EGFP and ECFP reporter genes are expressed as a single transcript, in which the mRNAs are linked by a spacer sequence, which can contain an oligonucleotide to be examined for IRES activity. Expression of both reporter genes is controlled by a strong RSV promoter to ensure efficient transcription of the RNA viral genome and, therefore, a high viral titer. The multiple cloning site between the EGFP and ECFP coding sequences facilitates the insertion of an oligonucleotide to be examined for translational activity.

The MESVR/EGFP/ECFP/RSVPro(ori) retroviral vector contains 6096 base pairs (SEQ ID NO: 16). Following insertion of the oligonucleotides to generate a library of proviruses, each containing a unique potential translational regulatory element in the intercistronic region of the dicistronic reporter cassette, the proviral vector library was transfected into mammalian cells together with helper plasmids required for viral production including a plasmid that encodes the group antigen (gag) and the integrase enzyme (pol) that is packaged with the RNA genome as well as a plasmid that encodes the vesicular stomatitis virus coat glycoprotein coat (VSV-G). The DNA provirus is transcribed to generate the RNA form, which is packaged into an infectious viral particle. The viral particle is coated with a glycoprotein that is recognized by receptors on the host cell leading to receptor-mediated internalization. After entry into the cell nucleus, the RNA genome is reverse transcribed into the DNA form which is stably integrated into the host cell genome.

The viral packaging protocol involved a triple transfection into COS1 cells of a library containing pro-retroviral vectors that harbor the putative promoter elements together with the two separate plasmids that encode the gag/pol and VSV-G proteins, respectively. Cellular transcription machinery is used to generate the viral RNA strands that are packaged into viral particles and subsequently bud from the cell membrane. These viral particles can infect a naive cell as described above. The viral library is fully representative of the original vector library because all viral RNAs were transcribed from the same strong promoter. In contrast, each integrated DNA version of the virus contains a different oligonucleotide sequence (or combination of sequences) in the intercistronic region, which can effect translation of the second reporter molecule and selection for which indicates IRES activity of the oligonucleotide.

Packaging of the proviral vector library was achieved by cotransfection of the proviral DNA into COS1 cells together with the packaging genes, which are contained on two separate helper plasmids, pCMV-GP(sal) and pMD.G. The pCMV-GP(sal) plasmid has a cytomegalovirus promoter (pCMV) driving the genes that encode the group antigen (gag) and reverse transcriptase enzyme (pol) from the Moloney murine leukemia virus (MMLV). The pMD.G plasmid encodes the vesicular stomatitis virus G glycoprotein (Naldini et al., *Science* 272(5259):263-267, 1996, which is incorporated herein by reference). These two plasmids were cotransfected into COS1 cells along with the library of recombinant retroviral vectors containing putative promoter elements in order to generate a library of retroviruses.

B. Selection f Synthetic Olig nucleotides Having IRES Activity

The disclosed synthetic IRES methodology provides a means for selecting functional IRES elements. The IRES selection method allows the parallel screening of millions of random oligonucleotide elements or combinations of elements for activity in mammalian cells. Selection of synthetic IRES elements in mammalian cells is facilitated if 1) each cell receives a single unique cassette to avoid selection of inactive elements that are fortuitously present in the same cell as an active element; 2) the synthetic IRES is shielded from the effects of genomic sequences that may activate or repress translation; 3) the delivery system is efficient so that a complex library can be readily screened; and 4) the selection process is stringent and is based on a reporter gene assay that is highly sensitive and faithfully reports the activity of the IRES elements.

A library of oligonucleotides was ligated immediately upstream of the second nucleotide sequence of a dicistronic reporter cassette comprising two reporter genes by insertion into a cloning site in the intercistronic spacer sequence. The exemplified reporter cassette (see below) contained nucleotide sequences encoding enhanced green fluorescent protein (EGFP) and enhanced cyan fluorescent protein (ECFP), which were arranged in a dicistronic construct that allows two separate gene products to be made from a single mRNA that is driven by a single promoter. After infection of cells with the retroviral IRES element library and integration into the genome, each IRES was scored for its translational activity by examining the activity of the ECFP reporter gene relative that of EGFP. After 2 to 3 days of infection, uninfected cells were selected by FACS to obtain cells expressing both EGFP and ECFP; the level of ECFP expression in each cell reflected the strength of an individual synthetic IRES element cassette, such that highly fluorescent cells are likely to contain highly active IRES elements. After multiple rounds of selection, the IRES sequences were amplified from the cellular genome by PCR and sequenced using an automated DNA sequencer to determine the identity of each of the synthetic IRES elements. The activity of each selected IRES element was confirmed by amplifying the entire IRES element, inserting the amplified element into a dicistronic luciferase reporter vector, and screening for the second luciferase reporter protein under translational control of the inserted IRES. This method allowed the testing of the regulatory cassette in a different reporter system, which was more amenable to quantitation of IRES activity levels.

Except as indicated, methods were performed essentially as described in Examples 1 to 3. A pool of random 18mers, flanked on either side by two different invariant sequences each 6 base pairs in length, was prepared and inserted into the Mlu I site in the intercistronic spacer of MESV/EGFP/ECFP/RSVPro (see FIG. 4). A library of recombinant retroviruses was made by transiently transfecting COS1 cells together with plasmids encoding the MLV gag/pol genes and the VSV-G glycoprotein gene. The library was introduced into B104 cells, then 48 hr later, the cells were subjected to FACS (see below) and cells expressing high levels of EGFP and ECFP were collected. The selected cells were replated, then sorted again for EGFP and ECFP expression. Genomic DNA was extracted from the twice-selected cells, and the 18mers were isolated by PCR using primers complementary to the sequences flanking the Mlu I cloning site in the vector.

IRES activity of the PCR amplified sequences was confirmed by cloning the fragments into the intercistronic region of the dicistronic reporter vector, RPh (Chappell et al., *Proc. Natl. Acad. Sci., USA* 97:1536-1541, 2000, which is incorporated herein by reference). Individual plasmid clones were transfected into B104 cells and the luciferase activities of the first cistron (*Renilla* luciferase) and the second cistron (*Photinus* luciferase) were assayed. For a given plasmid clone containing a particular 18mer sequence, an increase in the translation of the second cistron relative to the first cistron and normalized to the empty vector indicated that the 18mer functioned as an IRES element.

Oligonucleotides selected using this method and having IRES activity are shown as SEQ ID NOS: 42 to 46, where the first six nucleotides and last six nucleotides in each of the sequences are the invariant sequences flanking the randomly generated 18 nucleotides. These results demonstrate that synthetic IRES elements can be isolated by screening a library of random oligonucleotides using the disclosed methods.

C. Selecti n of Additional IRES Elements

To confirm the validity of the retroviral screening method, and to identify other short sequences with properties similar to those of the Gtx IRES module (SEQ ID NO: 2), B104 cells were infected with two retroviral libraries that contained random sequences of 9 or 18 nucleotides in the intercistronic region. Cells expressing both cistrons were sorted and sequences recovered from selected cells were examined for IRES activity using a dual luciferase dicistronic mRNA. Two novel IRES elements were identified, each of which contained a sequence with complementarity to 18S rRNA. When multiple copies of either element were linked together, IRES activities were dramatically enhanced. Moreover, the synthetic IRESes were differentially active in various cell types. The similarity of these properties to those of the Gtx IRES module (SEQ ID NO: 2) provides confirmatory evidence that short nucleotide sequences can function as translational regulatory elements.

Two retroviral libraries were generated. In the first library, an oligonucleotide containing 18 random nucleotides $(N)_{18}$ was cloned into the Mlu I site of the polylinker. The sequence of this oligonucleotide is: acgcgtgatcca$(N)_8$cgagcgacgcgt (SEQ ID NO: 47; see Edelman et al., *Proc. Natl. Acad. Sci., USA* 97:3038-3043, 2000, which is incorporated herein by reference). In the second library, an oligonucleotide containing two segments of 9 random nucleotides $(N)_9$ was cloned into the Pac I and Mlu I sites of the polylinker. The sequence of this oligonucleotide was ttaattaagaattcttctgacat(a)$_9$ttctgacat(a)$_9$ttctgacat(a)$_9$(N)$_9$(a)$_9$(N')$_9$(a)$_9$-gactcacaaccccagaaacagacatacgcgt (SEQ ID NO: 48), where N and N' are different random nucleotide sequences. The design of this oligonucleotide was based on the oligonucleotide $(S_{III}/S_{II})_5\beta$ (see Example 1). This oligonucleotide did not have IRES activity and was used as a spacer control. The first library consisted of about $2.5 \times 10^5$ bacterial clones and the second consisted of about $1.5 \times 10^5$ bacterial clones. As such; each library represented only a small fraction of the potential sequence complexity of the random oligonucleotides (about $6.9 \times 10^{10}$).

The retroviral libraries were packaged in COS1 cells. Subconfluent cells were triply transfected using the FuGENE 6 reagent (Roche Molecular Chemicals; Indianapolis Ind.) with plasmids encoding 1) the retroviral library, 2) MoMuLV gag and pol genes (pCMV-GP$_{(Sal)}$) and 3) the VSV-G glycoprotein (see Tranque et al., supra, 1998; Naldini et al., supra, 1996). After 48 hr, retroviral particles were recovered from culture supernatant, filtered through a 0.45 µm membrane, and then used to infect B104 rat neural tumor cells (Bottenstein and Sato, *Proc. Natl. Acad. Sci., USA* 76:514-517, 1979).

Approximately $2 \times 10^6$ COS1 cells were transfected, and approximately the same number of B104 cells were subsequently infected. After 72 hr, cells were harvested and sorted by FACS on a FACSVantage SE (Becton Dickinson; San Jose Calif.). EGFP was excited with an argon laser tuned to 488 nm and fluorescence was recorded through a 530 nm bandpass filter. ECFP was excited with a krypton/argon laser tuned to 457 nm, and fluorescence was measured through a 495 nm bandpass filter. As controls for the FACS, B104 cells were infected with the following reference viruses: the parent vector (MESV/EGFP/ECFP/RSVPro; SEQ ID NO: 16), a virus encoding EGFP, a virus encoding ECFP, and a virus that contains the IRES from the encephalomyocarditis virus (EMCV) in the intercistronic region of the parent vector.

Cells co-expressing both EGFP and ECFP were isolated and returned to culture for 14 days. These cells were then resorted, and high co-expressors were isolated and further expanded in culture for 5 to 7 days. Genomic DNA was prepared using a QiaAmp DNA miniprep kit (Qiagen). Intercistronic sequences were amplified by PCR using flanking primers, and cloned into the intercistronic region of RPh, which is a dicistronic vector that encodes *Renilla* luciferase protein as the first cistron and *Photinus* luciferase protein as the second cistron (Example 1; Chappell et al., supra, 2000). B 104 cells were transiently co-transfected with the dual luciferase vector and with a vector expressing β-galactosidase, and luciferase and β-galactosidase assays were performed (see Example 1). *Photinus* luciferase activity values were normalized for transfection efficiency by means of β-galactosidase activity, and were then normalized to the activity of the RPh parent vector (first library) or of RPh containing the $(S_{III}/S_{II})_5\beta$ oligonucleotide as a spacer control (second library).

Sequences of the oligonucleotide inserts were determined using an ABI system sequencer (PE Biosystems, Foster City, Calif.), and were compared using the Clustal X multiple sequence alignment program (Thompson et al., *Nucl. Acids Res.* 25:4876-4882, 1997), and with the BestFit program from the Genetics Computer Group software package (Devereux et al., *Nucl. Acids Res.* 12:387-395, 1984). Sequence matches were evaluated by comparing BestFit quality scores to those obtained when the selected sequences were randomly shuffled 10 times and compared to 18S rRNA. Secondary structure predictions were made using mfold version 3.0 (Zuker et al., in "RNA Biochemistry and Biotechnology" (ed. Clark; Kluwer academic publishers 1999), pages 11-43; Mathews et al., *J. Mol. Biol.* 288:911-940, 1999). Northern blot analysis was performed as described in Example 1 using a riboprobe encompassing the entire coding region of the *Photinus* luciferase gene.

The retroviral library containing the random 18 nucleotide inserts was examined. This library, derived from $2.5 \times 10^5$ retroviral plasmids was used to infect approximately $2 \times 10^6$ rat B104 neural tumor cells. After 72 hr, cells that co-expressed both EGFP and ECFP, corresponding to approximately 0.5% of the cells, were isolated by FACS. These cells were cultured for 14 days, sorted again by FACS, and high co-expressors, corresponding to approximately 4% of cells, were collected and grown. The twice sorted cells were compared to cells that had been infected with the virus that contained the EMCV IRES between the EGFP and ECFP genes. Both cell populations showed variable expression suggesting that IRES activity can vary among individual cells, perhaps reflecting cell cycle differences in the population.

Intercistronic sequences contained within the population of twice sorted cells were isolated by genomic PCR, and cloned into the intercistronic polylinker of the RPh vector (see Example 1). This dual luciferase vector has a stable hairpin-forming sequence in the transcribed leader region upstream of the *Renilla* open reading frame. The hairpin structure blocks scanning ribosomes and therefore suppresses translation of the first cistron. Fifty clones were picked at random and plasmid DNA was prepared, sequenced, and transiently transfected into B104 cells. Of the 45 clones that were successfully sequenced, 39 contained unique 18 nucleotide inserts. The sequences of the other 6 clones were each represented more than once, which may reflect the relatively low complexity of selected sequences in these twice sorted cells.

The sequenced clones were tested in transfected cells and most activities were weak or at a background level. However, one sequence, designated intercistronic sequence 1-23 (ICS1-23; SEQ ID NO: 49) demonstrated enhanced *Photinus* luciferase activity approximately 8-fold greater than the control constructs. This level of activity was similar to that observed for one copy of the Gtx IRES module (Example 1).

Figure 5:
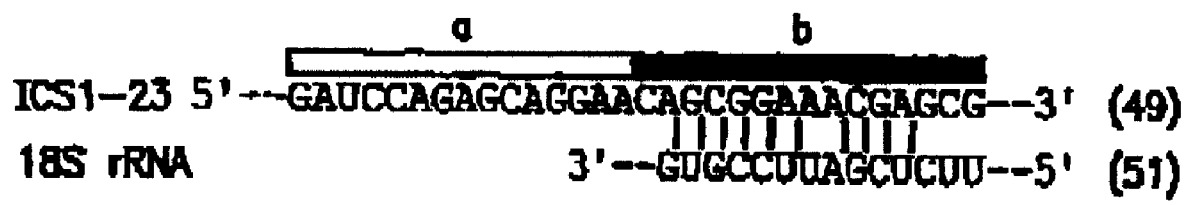
FIG. 5 shows a region of complementarity of 18S ribosomal RNA (SEQ ID NO:50) and a synthetic IRES element, ICS1-23 (SEQ ID NO: 49). "a" and "b" indicates portions of SEQ ID NO: 49 that were examined separately for IRES activity. SEQ ID NOS: are indicated in parentheses.

A sequence comparison between ICS1-23 (SEQ ID NO: 49) and 18S rRNA (SEQ ID NO: 51) revealed a complementary match between the 3' end of the IRES and 18S rRNA at nucleotides 1311-1324 (FIG. 5). This match has a BestFit quality score that is significantly greater than that obtained with 10 randomized variations of this sequence. To address whether the region of complementarity within ICS 1-23 was associated with the IRES activity, the 30 nucleotide ICS1-23 sequence, which includes the 18 nucleotide random sequence together with 12 nucleotides of flanking sequence, was divided into two segments of 15 nucleotides each, ICS1-23a, which lacked any complementarity to 18S rRNA (see FIG. 5, and ICS1-23b (SEQ ID NO: 50) contained the complementary match to 18S rRNA (SEQ ID NO: 51).

As disclosed in Example 1, multiple linked copies of the Gtx IRES module (SEQ ID NO: 2) were more active than the corresponding monomer. Accordingly, multimers of each segment of ICS1-23 were synthesized, with each repeated segment separated by nine adenosine nucleotides (poly(A)$_9$). Three linked copies of the ICS1-23a segment (see FIG. 5) did not enhance *Photinus* luciferase expression. In contrast, constructs containing three and five linked copies of ICS1-23b (SEQ ID NO: 51) enhanced *Photinus* luciferase activity as compared to ICS1-23. These results indicate that the sequence of ICS1-23 that shares complementarity with 18S rRNA has IRES activity. Northern blot analysis of RNA from cells expressing the five linked copies of ICS1-23b revealed a single hybridizing band corresponding in size to the full length dicistronic mRNA, thus confirming that ICS-23b did not enhance *Photinus* luciferase activity by other mechanisms such as alternative splicing or by functioning as a promoter.

The second retroviral library, which contained random 9 nucleotide segments separated by a poly(A)$_9$ spacer in the intercistronic region of the encoded dicistronic mRNA, was examined in order to identify smaller translational regulatory elements. Incorporation of the spacer sequence was based on the determination that the Gtx IRES module (SEQ ID NO: 2), when present in multiple copies separated by the poly(A)$_9$ spacer, exhibited greater IRES activity than a single copy of the module (see Example 1).

Approximately 2×10$^6$ B104 cells were transduced with the second retroviral library, which was derived from 1.5×10$^5$ retroviral plasmids. Approximately 0.3% of the cells were selected by FACS, and cultured and sorted a second time. Approximately 3% of the latter cells were high co-expressors. The oligonucleotide inserts were recovered by genomic PCR and shotgun cloned into the intercistronic region of the RPh. One hundred clones were picked at random and 84 were successfully sequenced, yielding 37 different sequences. Fifteen of the sequences were represented two or more times, indicating that the complexity of the sequences represented in these twice sorted cells was somewhat lower than that of the first library. When tested by transient transfection in B104 cells, most sequences enhanced *Photinus* luciferase activity weakly (about 2-fold or less above background), and none were as active as ICS1-23 (SEQ ID NO: 49).

Six of the sequences, which were isolated four or more times from the twice sorted cells, were examined further. Each of these sequences contained two 9 nucleotide segments, which were tested individually as five linked copies. One of these constructs, containing a 9 nucleotide segment designated ICS2-17.2 (TCCGGTCGT; SEQ ID NO: 52), showed enhanced *Photinus* luciferase activity. In contrast to the five linked copies of ICS2-17.1, the other 9 nucleotide segment contained within selected sequence ICS2-17 did not have IRES activity. RNA analysis confirmed that a single transcript was produced from the construct, and that the increase in *Photinus* luciferase activity was derived from an intact dicistronic mRNA. These results indicate that ICS2-17.2 (SEQ ID NO: 52) functions as an IRES.

Five linked copies of both ICS1-23b and ICS2-17.2 also were examined using the 5' UTR of a monocistronic reporter mRNA. In 7 cell lines tested, (ICS1-23b)$_5$ blocked translation by approximately 70% and (ICS2-17.2)$_5$ slightly enhanced translation. In both cases, mRNA levels appeared to be unaffected. This result indicates that ICS1-23b and ICS2-17.2 function as IRES elements in the dicistronic mRNAs, but not as transcriptional promoters or enhancers. As with ICS1-23b, sequence comparisons identified a complementary match between ICS2-17.2 and 18S rRNA with a BestFit quality score that is significantly greater than that obtained with 10 randomized variations of the this sequence.

The activity of the selected ICS1-23b (SEQ ID NO: 51) and ICS2-17.2 (SEQ ID NO: 52) IRES modules was examined in additional cell lines to determine whether they were active in cell types other than the B104 neuroblastoma cells. A construct of five linked copies of each module was active in each of the cells line tested, including rat glioma C6 cells, human neuroblastoma SK cells, mouse neuroblastoma N2a cells, mouse N1H-3T3 fibroblasts, human cervical carcinoma HeLa cells, normal rat kidney NRK cells, and mouse muscle myoblast C2C12 cells. The activities of these synthetic IRE-Ses varied as much as ten-fold between cell lines, and also varied with respect to each other. However, the pattern of activity of the ICS-23b (SEQ ID NO: 51) module in the different cell lines tested was similar to that observed for ten linked copies of the Gtx IRES module (SEQ ID NO: 2).

These results demonstrate that relatively small discrete nucleotide sequences can act as translational regulatory elements, including as IRES elements, which mediate cap-independent translation. Furthermore, the two IRES modules identified in this Example were selected from only a minute sampling of the total complexity of the random oligonucleotides. Thus, it is likely that screening a more complex library of random oligonucleotide will identity additional short nucleotide sequences having IRES or other translational regulatory activity.

It is remarkable that each of the short IRES element disclosed herein, including the Gtx IRES (SEQ ID NO: 2), the ICS1-23b IRES (SEQ ID NO: 51), and the ICS2-17.2 IRES (SEQ ID NO: 52) can promote internal initiation. Each of these three IRES modules contain a complementary match to different segments of 18S rRNA, suggesting that a direct interaction occurs between the IRES module and the 40S ribosomal subunit via base pairing to 18S rRNA. Alternatively, one or more of the IRES modules may recruit 40S ribosomal subunits by interacting with a protein component of the translational machinery, for example, a ribosomal protein, an initiation factor, or some other bridging protein. The ability to initiate translation internally by binding to an initiation factor has been reported, wherein an iron response element (IRE) and the bacteriophage λ transcriptional antiterminator box B element were both demonstrated to function as IRESes in the presence of fusion proteins between the appropriate binding protein for these RNA elements and eIF4G (DeGregorio et al., *EMBO J*. 18:4865-4874, 1999). However, the lack of appreciable sequence similarities between the IRES modules disclosed herein and cellular IRESes in general suggests that a wide variety of nucleotide sequences can function in internal translation initiation, and suggests that different sequences recruit pre-initiation complexes by different mechanisms.

The observation that synthetic IRESes comprising multimers of ICS1-23b, ICS2-17.2, or the Gtx IRES module show enhanced IRES activity as compared to the corresponding monomers suggest that multiple copies of the IRES module may increase the probability of recruiting 40S ribosomal subunits. A similar observation has been made for eIF4G tethered to the IRE-binding protein, where there was an approximately linear increase in translation when the number of IRE binding sites was increased from one site to three (DeGregorio et al., supra, 1999).

An arresting feature of cellular IRESes, including the disclosed IRES modules, is their variable potency in different cell types. As such, selection for IRESes in a variety of cell types can provide a means to identify additional elements having cell-specific and tissue-specific activities. If ribosomal recruitment requires direct interaction of IRESes with 18S rRNA, variations in efficiency may reflect differences in the accessibility of particular segments of 18S rRNA in different cell types. Alternatively, some IRES modules may require or may be blocked by binding proteins that are differentially expressed in various cell types. Such possibilities can be distinguished by determining which proteins or components of the translation machinery bind to particular IRES sequences in various differentiated cells. In view of the modular nature of cellular IRES, combinations of synthetic IRESes can be constructed and elements having desirable regulatory actions can be selected. Such a combinatorial approach can be used to construct synthetic IRESes having variable translational regulatory activity, for example, highly restricted or widespread translational activity.

D. Additional Synthetic IRES Elements

A library of synthetic oligonucleotides containing two random 9 nucleotide (Ran9) sequences also was examined for IRES activity. The Ran9 oligonucleotides were in a construct that contained, from the 5' to the 3' end, 62 nucleotides of the β-globin leader, a poly(A)9 sequence, the first Ran9 oligonucleotide, a poly(A)9 spacer, the second Ran9 oligonucleotide, a poly(A)9 sequence, and 44 nucleotides of the β-globin leader (see, for example, SEQ ID NO: 53), which includes specific nucleotides corresponding to the two Ran9 positions; see below).

Thirty-six of the constructs that exhibited IRES activity are shown as SEQ ID NOS: 53 to 88. In addition, the individual IRES modules from these constructs are shown as SEQ ID NOS: 89 to 160.

EXAMPLE 5

Identification of IRES Activity in 5' UTRs of Mammalian RNAs

IRES elements also were identified in the 5' transcribed leader sequences of the mRNAs that encode the rat amyloid precursor protein (APP; Rogers et al., *J. Biol. Chem.* 274: 6421-6431, 1999, which is incorporated herein by reference) and the beta-site APP cleaving enzyme (Bace; Yan et al., *Nature* 402:533-7, 1999, which is incorporated herein by reference). In addition, IRES activity was associated with the 5' UTR of the human FMR mRNA. These IRES elements were identified and characterized in the intercistronic region of a dual luciferase dicistronic mRNA, as disclosed above.

The 5' transcribed leader sequence of the mRNA encoding rat APP is shown as SEQ ID NO: 161. The 5' transcribed leader sequence of the mRNA encoding rat Bace is shown as SEQ ID NO: 162. The 5' untranslated region of the human FMR mRNA is shown as SEQ ID NO: 163. Using the methods as disclosed in Examples 1 and 6, translational regulatory elements of these 5' UTRs, including IRES modules, readily can be identified and isolated.

EXAMPLE 6

Identification of IRES Module in Mouse Rbm3 5'UTR

IRES activity also was detected in the 728 nucleotide 5' UTR of the mouse Rbm3 mRNA (SEQ ID NO: 164, which includes ATG initiator methionine). In addition, fragments of the Rbm3 5' LTR had IRES activity, including the following sequences: nucleotides 1 to 97, nucleotides 199 to 299, nucleotides 299 to 406, nucleotides 400 to 501, nucleotides 419 to 501, nucleotides 440 to 460, nucleotides 500 to 601, nucleotides 600 to 728, nucleotides 630 to 650, nucleotides 650 to 670 and nucleotides 690 to 710 of SEQ ID NO: 164.

Figure 6:
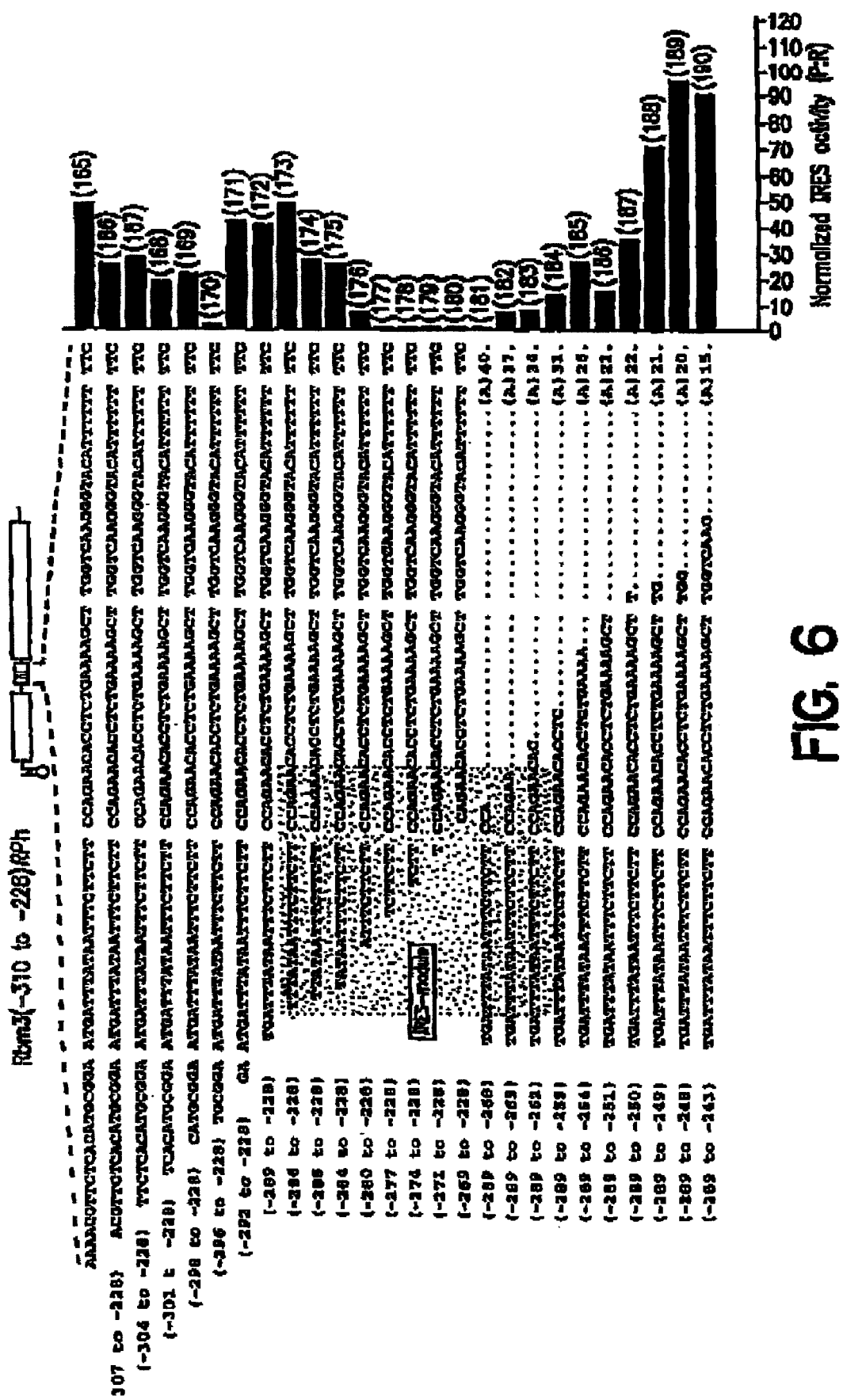
FIG. 6 shows deletion constructs of a nucleotide sequence (SEQ ID NO: 164) encoding the mouse Rbm3 5' UTR, and illustrates a portion of the RPh vector in which the sequences were examined for IRES activity. Nucleotide positions relative to the 5' UTR (SEQ ID NO: 164) are indicated in parentheses to the left, and SEQ ID NOS: are indicated in parentheses to the right of the figure. Adenosine residues were added to the 3' deleted sequences (SEQ ID NOS: 181-190) such that the relative distance to the natural Rbm3 AUG start codon was maintained (indicated in Figure as, for example, "(A)40"; see SEQ ID NO: 181). Normalized IRES activity of the various constructs is shown (see description of FIG. 4. above).

To further characterize the Rbm3 5' UTR, deletions were made from the 5' and 3' ends and examined using the dicistronic RPh vector (see Example 1). FIG. 6 shows the sequences of the various deletion constructs (SEQ ID NOS: 165 to 190; note that adenosine residues were added to 3' end of 3' deletion mutants to maintain relative distance to naturally occurring Rbm3 initiator AUG codon) and the IRES activity associated with each (shown as the R:P ratio, normalized to 1.0 for the activity of the parent RPh vector). The deletion studies indicated that IRES activity a core element comprising the sequence TTTATAATTTCTTCTTCCAGAA (SEQ ID NO: 191) conferred IRES activity. In addition, the sequence GAAAGCTTG (SEQ ID NO: 192), which is positioned beginning 8 nucleotides downstream of the core IRES element enhances the activity of the IRES module by about 10-fold, but does not have IRES activity on its own. These results demonstrate that a core IRES module is present in the Rbm3 5' UTR and, together with the results disclosed above, indicate that small IRES modules can be present in a variety of eukaryotic mRNA molecules.

The deletion studies of the Rbm3 5' UTR also indicated that nucleotide sequences in the 5' UTR may inhibit IRES activity. Analysis of the deletion mutants revealed an Rbm3 IRES inhibitory sequence, GGTACATTTTTTTC (SEQ ID NO: 193), which is positioned about 21 nucleotides downstream of the IRES module and inhibited internal initiation of translation facilitated by the nearby IRES module. In addition, a second inhibitory sequence, ATGCGGAATGATTTATAA (SEQ ID NO: 194), which partially overlaps the 5' end of the Rbm3 IRES module, contains a short open reading frame that inhibits internal initiation only when the Rbm3 initiation codon is mutated. This result indicates that a translational inhibitory element can be masked by an open reading frame.

EXAMPLE 7

IRES Modules Based on Ribosomal RNA Structure

This example demonstrates that synthetic oligonucleotides having IRES activity can be designed based on the structure of ribosomal RNA molecules.

It is not present clear how cellular IRESes function. As disclosed herein, however, cellular IRESes exist as modular structures composed of short, independent oligonucleotides, including oligonucleotide that are complementary to 18S rRNA. These results indicate that recruitment of ribosomal subunits by IRES modules is directed by base pairing of the IRES element to the rRNA within the ribosomal subunit.

The 9 nucleotide Gtx IRES module (SEQ ID NO: 2) is 100% complementary to an oligonucleotide sequence of 18S rRNA, and was tested as an IRES module based on this observation. In addition, the ability of the Gtx IRES module (SEQ ID NO: 2) to recruit 40S ribosomal subunits by base pairing to 18S rRNA was examined. Nitrocellulose filter-binding and electrophoretic mobility gel shift assays established a physical link between the 9 nucleotide Gtx IRES module (SEQ ID NO: 2) and dissociated ribosomal subunits, but not with other components of cell lysates. Transfection studies using dicistronic constructs that contained the Gtx IRES module (SEQ ID NO: 2) or mutations of this sequence (see FIG. 2) demonstrated that internal initiation was maximal with a mutant module sharing 7 nucleotides of complementarity with 18S rRNA, and that as the degree of complementarity was progressively increased or decreased, IRES activity was decreased and, ultimately, lost. When tested in the 5' or 3' UTR of a monocistronic mRNA, sequences that enhanced internal initiation also functioned as translational enhancers. However, only those sequences with increased complementarity to 18S rRNA inhibited both internal initiation and translation in monocistronic mRNAs. This inhibition appeared to involve stable interactions between the mRNA and 40S ribosomal subunits as determined by polysome analysis. These results indicate that internal initiation of translation can occur at short nucleotide sequences by base pairing to 18S rRNA.

Figure 7A:
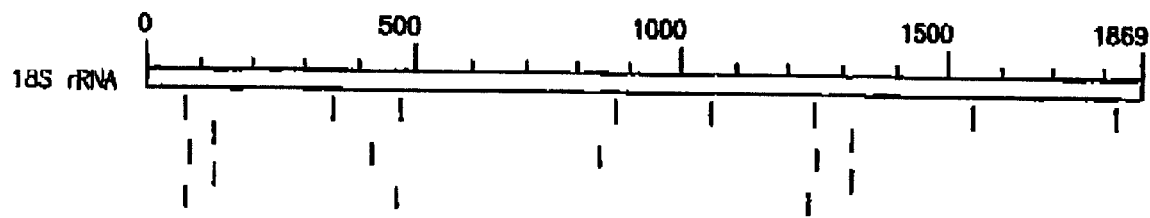
FIGS. 7A and 7B illustrate sites in which IRES modules of the invention share complementarity to mouse 18S ribosomal RNA (rRNA; SEQ ID NO: 196).
Figure 7B:
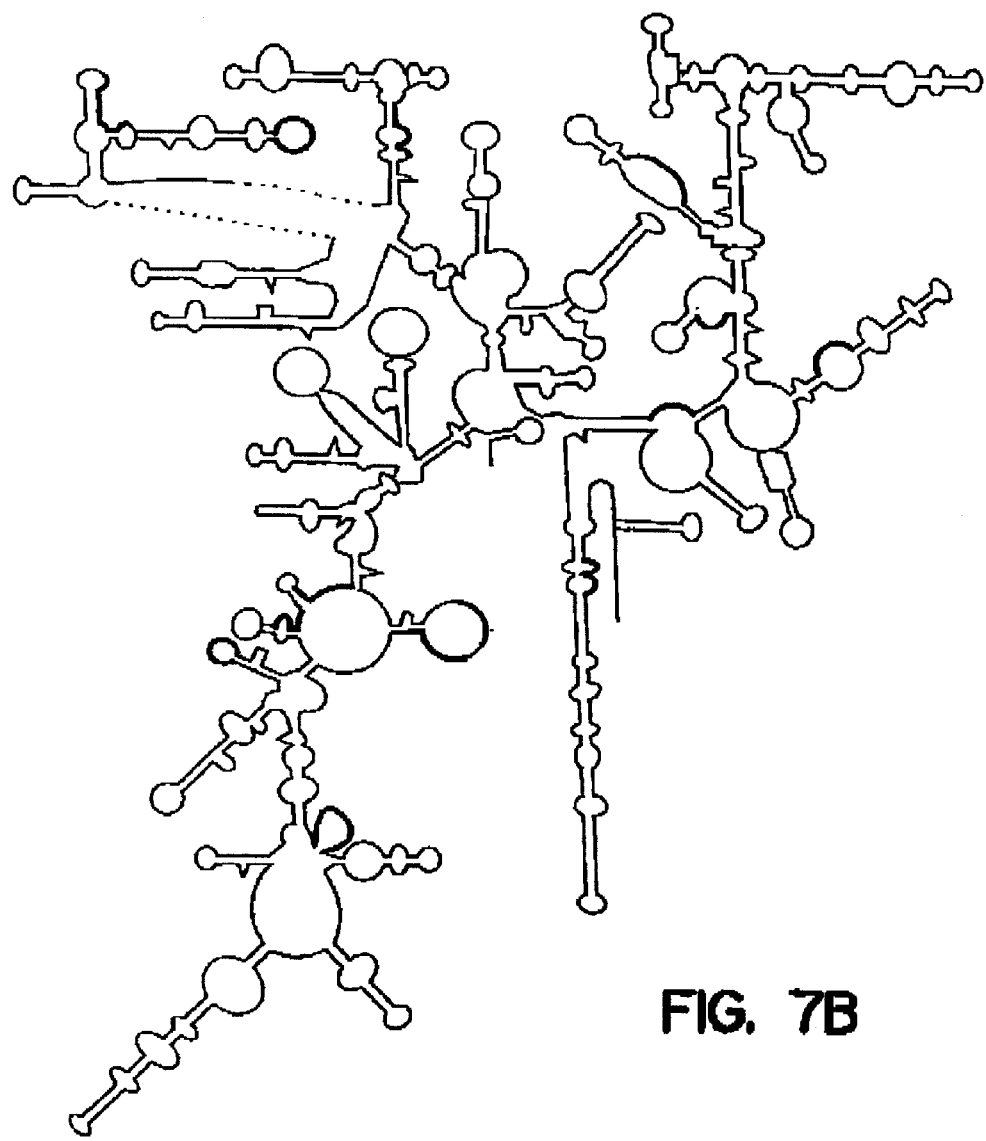

Sequence analysis of the IRES-modules recovered from the selection studies showed that most of the selected sequences contained complementary sequence matches of 8 to 9 nucleotides to different regions of the 18S rRNA (FIG. 7). Furthermore, many of the matches are to un-base paired regions of the rRNA (see FIG. 7B). Moreover, in some cases, several selected sequences with slightly different sequences, were complementary to the same region of the 18S rRNA (see, also, Owens et al., 2001, which is incorporated herein by reference). These results indicate that synthetic translational regulatory elements can be designed based on rRNA sequences such as those set forth in SEQ ID NOS: 195-197, particularly to un-base paired rRNA sequences, which can be predicted using methods as disclosed herein, such that the synthetic translational regulatory elements are complementary to a selected rRNA target sequence.

Although the invention has been described with reference to the above examples, it will be understood that modifications and variations are encompassed within the spirit and scope of the invention. Accordingly, the invention is limited only by the following claims.

---

What is claimed is:

1. A synthetic translational regulatory element, comprising at least two oligonucleotides, each encoded by a nucleotide sequence consisting of SEQ ID NO: 52, wherein the oligonucleotides have translational enhancing activity or internal ribosome entry site (IRES) activity, and wherein the synthetic translational regulatory element has translational regulatory activity in a eukaryotic cell.

2. The synthetic translational regulatory element of claim 1, wherein the at least two oligonucleotides are operatively linked to each other.

3. The synthetic translational regulatory element of claim 2, which has IRES activity.

4. The synthetic translational regulatory element of claim 1, which has translational enhancing activity.

5. A vector, comprising the synthetic translational regulatory element of claim 1.

6. An insolated host cell containing the synthetic translational regulatory element of claim 1.

7. A kit, comprising the synthetic translational regulatory element of claim 1.

8. A recombinant nucleic acid molecule, comprising the synthetic translational regulatory element of claim 1 operatively linked to an expressible polynucleotide.

9. The synthetic translational regulatory element of claim 2, comprising five copies of said oligonucleotides, which are operatively linked to each other.

10. The synthetic translational regulatory element of claim 2, comprising ten copies of said oligonucleotides, which are operatively linked to each other.

11. The synthetic translational regulatory element of claim 2, comprising 50 copies of said oligonucleotides, which are operatively linked to each other.

12. The synthetic translational regulatory element of claim 2, wherein each of said at least two oligonucleotides is separated from each other by a spacer nucleotide sequence, wherein said spacer nucleotide sequence consists of about 1 to 100 ribonucleotides.

13. The vector of claim 5, which is an expression vector.

14. The expression vector of claim 13, which comprises a translation initiation site, wherein the translational regulatory element has translational enhancing activity.

15. The expression vector of claim 14, further comprising a translation start codon operatively linked to the translation initiation site.

16. The expression vector of claim 14, further comprising an expressible polynucleotide, wherein the translational regulatory element is operatively linked to the expressible polynucleotide, and wherein the translational regulatory element has translational enhancing activity or TRES activity.

17. The expression vector of claim 16, wherein the expressible polynucleotide comprises at least one cistron.

18. The expression vector of claim 17, wherein the expressible polynucleotide is polycistronic.

19. The kit of claim 7, comprising a plurality of synthetic translational regulatory elements, which are the same or different sequence from each other.

20. The kit of claim 19, wherein each of the synthetic translational regulatory elements in the plurality independently comprises a flanking sequence at a 5' end or a 3' end or both 5' and 3' ends, and wherein the flanking sequences provide a means to operatively link two or more synthetic translational regulatory elements in the plurality to each other.

21. The recombinant nucleic acid molecule of claim 8, wherein the expressible polynucleotide comprises a cistron, and wherein the synthetic translational regulatory element has translational enhancing activity or IRES activity.

22. The recombinant nucleic acid molecule of claim 8, wherein the expressible polynucleotide comprises, in operative linkage in a 5' to 3' orientation, a first cistron, a spacer nucleotide sequence, and a second cistron, wherein the synthetic translational regulatory element has IRES activity, and wherein the synthetic translational regulatory element is operatively linked to the second cistron.

23. The recombinant nucleic acid molecule of claim 8, wherein the expressible polynucleotide encodes at least one polypeptide.

24. The recombinant nucleic acid molecule of claim 23, wherein the at least one polypeptide is an enzyme.

25. The recombinant nucleic acid molecule of claim 23, wherein the at least one polypeptide is selected from a viral polypeptide and a bacterial polypeptide.

26. The recombinant nucleic acid molecule of claim 23, wherein the at least one polypeptide comprises an epitope expressed by a pathogenic organism.

27. The recombinant nucleic acid molecule of claim 23, wherein the at least one polypeptide is selected from a growth factor, a hormone and a receptor for a growth factor or a hormone.

28. The recombinant nucleic acid molecule of claim 23, wherein the expressible polynucleotide encodes two polypeptides.

29. The recombinant nucleic acid molecule of claim 24, wherein the enzyme is selected from β-galactosidase, β-glucuronidase, luciferase, alkaline phosphatase, glutathione S-transferase, cliloramphenicol acetyltransferase, guanine xanthine phosphoribosyltransferase, and neomycin phosphotransferase.

30. An isolated genetically modified eukaryotic cell that exhibits altered expression of a polypeptide, the cell produced by introducing into a cell a synthetic translational regulatory element comprising at least two oligonucleotides, each encoded by a nucleotide sequence consisting of SEQ ID NO: 52, wherein the oligonucleotides have translational enhancing activity or internal ribo some entry site (IRES) activity, wherein the synthetic translational regulatory element has translational regulatory activity in a eukaryotic cell, and wherein the synthetic translational regulatory element is integrated in the cell genome, whereby the synthetic translational regulatory element is operatively linked to a nucleotide sequence encoding a polypeptide, thereby producing a genetically modified cell that exhibits altered expression of a polypeptide.

31. An isolated cell obtained by isolating a cell identified by introducing into the cell a recombinant nucleic acid molecule comprising a synthetic translational regulatory element operatively linked to an expressible polynucleotide, wherein the synthetic translational regulatory element comprises at least two oligonucleotides, each encoded by a nucleotide sequence consisting of SEQ ID NO: 52, wherein the oligonucleotides have translational enhancing activity or IRES activity, wherein the synthetic translational regulatory element has translational regulatory activity in a eukaryotic cell, wherein the expressible polynucleotide comprises at least one cistron, which encodes a first reporter polypeptide, and wherein expression of the reporter polypeptide in the cell provides a means to identify the cell.

* * * * *